(12) United States Patent
Liu et al.

(10) Patent No.: US 10,919,904 B2
(45) Date of Patent: Feb. 16, 2021

(54) NORTHERN-SOUTHERN ROUTE TO SYNTHESIS OF BACTERIOCHLORINS

(71) Applicant: North Carolina State University, Raleigh, NC (US)

(72) Inventors: Yizhou Liu, Raleigh, NC (US); Jonathan S. Lindsey, Raleigh, NC (US); Srinivasa Rao Allu, Philadelphia, PA (US); Hikaru Fujita, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/323,607

(22) PCT Filed: Aug. 17, 2017

(86) PCT No.: PCT/US2017/047266
§ 371 (c)(1),
(2) Date: Feb. 6, 2019

(87) PCT Pub. No.: WO2018/035281
PCT Pub. Date: Feb. 22, 2018

(65) Prior Publication Data
US 2019/0256521 A1 Aug. 22, 2019

Related U.S. Application Data

(60) Provisional application No. 62/376,078, filed on Aug. 17, 2016.

(51) Int. Cl.
| | | |
|---|---|---|
| *C07D 487/22* | (2006.01) | |
| *A61P 35/00* | (2006.01) | |
| *A61K 9/00* | (2006.01) | |
| *A61K 31/409* | (2006.01) | |
| *G01N 15/14* | (2006.01) | |
| *G01N 33/483* | (2006.01) | |
| *A61K 41/00* | (2020.01) | |

(52) U.S. Cl.
CPC .......... *C07D 487/22* (2013.01); *A61K 9/0019* (2013.01); *A61K 31/409* (2013.01); *A61K 41/0071* (2013.01); *A61P 35/00* (2018.01); *G01N 15/14* (2013.01); *G01N 33/483* (2013.01); *G01N 15/1459* (2013.01)

(58) Field of Classification Search
CPC .................................................. C07D 487/22
See application file for complete search history.

(56) References Cited

U.S. PATENT DOCUMENTS

| | | |
|---|---|---|
| 3,710,795 A | 1/1973 | Higuchi et al. |
| 3,817,837 A | 6/1974 | Rubenstein et al. |
| 3,927,193 A | 12/1975 | Hansen et al. |
| RE28,819 E | 5/1976 | Thompson |
| 4,044,126 A | 8/1977 | Cook et al. |
| 4,179,337 A | 12/1979 | Davis et al. |
| 4,328,245 A | 5/1982 | Yu et al. |
| 4,331,647 A | 5/1982 | Goldenberg |
| 4,348,376 A | 9/1982 | Goldenberg |
| 4,358,603 A | 11/1982 | Yu |
| 4,361,544 A | 11/1982 | Goldenberg |
| 4,364,923 A | 12/1982 | Cook et al. |
| 4,374,925 A | 2/1983 | Litman et al. |
| 4,409,239 A | 10/1983 | Yu |
| 4,410,545 A | 10/1983 | Yu et al. |
| 4,414,209 A | 11/1983 | Cook et al. |
| 4,444,744 A | 4/1984 | Goldenberg |
| 4,468,457 A | 8/1984 | Goldenberg |
| 4,474,893 A | 10/1984 | Reading |
| 4,479,895 A | 10/1984 | Auditore-Hargreaves |
| 4,522,811 A | 6/1985 | Eppstein et al. |
| 4,624,846 A | 11/1986 | Goldenberg |
| 4,818,709 A | 4/1989 | Primus et al. |
| 4,946,778 A | 8/1990 | Ladner et al. |
| 5,033,252 A | 7/1991 | Carter |
| 5,052,558 A | 10/1991 | Carter |
| 5,059,415 A | 10/1991 | Neuwelt |
| 5,323,907 A | 6/1994 | Kalvelage |
| 5,441,827 A | 8/1995 | Gratzel et al. |
| 5,681,811 A | 10/1997 | Ekwuribe |
| 5,709,874 A | 1/1998 | Hanson et al. |
| 5,759,542 A | 6/1998 | Gurewich |
| 5,840,674 A | 11/1998 | Yatvin et al. |
| 5,860,957 A | 1/1999 | Jacobsen et al. |
| 5,900,252 A | 5/1999 | Calanchi et al. |

(Continued)

FOREIGN PATENT DOCUMENTS

| | | |
|---|---|---|
| EP | 0243929 | 11/1987 |
| JP | 1158995 | 3/1999 |

(Continued)

OTHER PUBLICATIONS

Diev. Journal of Organic Chemistry, 2012, 77, 143-159 (Year: 2012).*

Yamaguchi. Journal of Chemical Physics, 2005, 122, 184702-1 to 184702-9 (Year: 2005).*

Anderson et al. "Pyrrole Chemistry: The Preparation and Some Reactions of Brominated Pyrrole Derivatives" Canadian Journal of Chemistry, 43:409-414 (1965).

Bruckner et al. "β,β~'-dihydroxylation of meso-tetraphenylchlorins and metallochlorins" Tetrahedron Letters, 36(52):9425-9428 (1995).

(Continued)

*Primary Examiner* — Noble E Jarrell

(74) *Attorney, Agent, or Firm* — Myers Bigel, P.A.

(57) ABSTRACT

Described herein are chlorins, bacteriochlorins, methods and intermediates for the synthesis of bacteriochlorins, and methods of using such bacteriochlorins for, among other things, diagnostic and therapeutic purposes such as luminescent compounds in flow cytometry, and as active agents in photodynamic therapy (PDT).

18 Claims, No Drawings

(56) References Cited

U.S. PATENT DOCUMENTS

| | | | |
|---|---|---|---|
| 5,915,925 | A | 6/1999 | North, Jr. |
| 5,948,433 | A | 9/1999 | Burton et al. |
| 5,952,366 | A | 9/1999 | Pandey et al. |
| 5,972,366 | A | 10/1999 | Haynes et al. |
| 5,983,134 | A | 11/1999 | Ostrow |
| 5,985,307 | A | 11/1999 | Hanson et al. |
| 5,985,317 | A | 11/1999 | Venkateshwaran et al. |
| 6,004,534 | A | 12/1999 | Langer et al. |
| 6,010,715 | A | 1/2000 | Wick et al. |
| 6,024,975 | A | 2/2000 | D'Angelo et al. |
| 6,039,975 | A | 3/2000 | Shah et al. |
| 6,048,736 | A | 4/2000 | Kosak |
| 6,060,082 | A | 5/2000 | Chen et al. |
| 6,071,495 | A | 6/2000 | Unger et al. |
| 6,120,751 | A | 9/2000 | Unger |
| 6,131,570 | A | 10/2000 | Schuster et al. |
| 6,139,865 | A | 10/2000 | Friend et al. |
| 6,167,301 | A | 12/2000 | Flower et al. |
| 6,208,553 | B1 | 3/2001 | Gryko et al. |
| 6,212,093 | B1 | 4/2001 | Lindsey |
| 6,248,590 | B1 | 6/2001 | Malachowski |
| 6,253,872 | B1 | 7/2001 | Neumann |
| 6,256,533 | B1 | 7/2001 | Yuzhakov et al. |
| 6,261,595 | B1 | 7/2001 | Stanley et al. |
| 6,267,983 | B1 | 7/2001 | Fujii et al. |
| 6,271,359 | B1 | 8/2001 | Norris et al. |
| 6,273,904 | B1 | 8/2001 | Chen et al. |
| 6,274,552 | B1 | 8/2001 | Tamarkin et al. |
| 6,316,652 | B1 | 11/2001 | Steliou |
| 6,324,091 | B1 | 11/2001 | Gryko et al. |
| 6,381,169 | B1 | 4/2002 | Bocian et al. |
| 6,407,330 | B1 | 6/2002 | Lindsey et al. |
| 6,420,648 | B1 | 7/2002 | Lindsey |
| 6,451,942 | B1 | 9/2002 | Li et al. |
| 6,524,570 | B1 | 2/2003 | Glue et al. |
| 6,589,792 | B1 | 7/2003 | Malachowski |
| 6,656,906 | B1 | 12/2003 | Barney et al. |
| 6,657,884 | B2 | 12/2003 | Bocian et al. |
| 6,706,963 | B2 | 3/2004 | Gaudiana et al. |
| 6,716,811 | B1 | 4/2004 | Cwirla et al. |
| 6,720,306 | B2 | 4/2004 | Greenwald et al. |
| 6,728,129 | B2 | 4/2004 | Lindsey et al. |
| 6,858,158 | B2 | 2/2005 | Chittibabu et al. |
| 6,890,487 | B1 | 5/2005 | Sklar et al. |
| 6,900,382 | B2 | 5/2005 | Chittibabu et al. |
| 6,913,713 | B2 | 7/2005 | Chittibabu et al. |
| 6,924,427 | B2 | 8/2005 | Eckert et al. |
| 6,933,436 | B2 | 8/2005 | Shaheen et al. |
| 7,501,507 | B2 | 3/2009 | Balakumar et al. |
| 8,530,459 | B2 | 9/2013 | Borbas et al. |
| 8,664,260 | B2 | 3/2014 | Kim et al. |
| 2004/0044197 | A1 | 3/2004 | Pandey et al. |
| 2005/0096465 | A1 | 5/2005 | Lindsey et al. |

FOREIGN PATENT DOCUMENTS

| | | |
|---|---|---|
| WO | 1990015059 | 12/1990 |
| WO | 2000073308 | 12/2000 |
| WO | 2006089122 | 8/2006 |
| WO | 2007064842 | 6/2007 |
| WO | 2012166792 | 12/2012 |
| WO | 2013062670 | 5/2013 |

OTHER PUBLICATIONS

Chen et al. "Synthesis of Bacteriochlorins and Their Potential Utility in Photodynamic Therapy (PDT)" Current Organic Chemistry, 8:1105-1134 (2004).

Chew et al. "Chlorophyll Biosynthesis in Bacteria: The Origins of Structural and Functional Diversity" Annual Review of Microbiology, 61:113-129 (2007).

Deng et al. "An Efficient Convergent Synthesis of Novel Anisotropic Adsorbates Based on Nanometer-Sized and Tripod-Shaped Oligophenylenes End-Capped with Triallylsilyl Groups" The Journal of Organic Chemistry, 67(15):5279-5283 (2002).

Dorough et al. "An Attempted Preparation of a Simple Tetrahydroporphine" Journal of the American Chemical Society, 74(23):6106-6108 (1952).

Fan et al. "Regioselective 15-Bromination and Functionalization of a Stable Synthetic Bacteriochlorin" The Journal of Organic Chemistry, 72:5350-5357 (2007).

Fox et al. "Fluorescence and Redox Activity of Probes Anchored through an Aminotrithiol to Polycrystalline Gold" Langmuir, 14(4):816-820 (1998).

Galoppini et al. "Long-Distance Electron Transfer Across Molecule-Nanocrystalline Semiconductor Interfaces" Journal of the American Chemical Society, 123(18):4342-4343 (2001).

Galoppini et al. "Long-Range Electron Transfer across Molecule-Nanocrystalline Semiconductor Interfaces Using Tripodal Sensitizers" Journal of the American Chemical Society, 124(26):7801-7811 (2002).

Hector et al. "Investigation of vinyl phosphonic acid/hydroxylated alpha-Al2O3(0001) reaction enthalpies" Surface Science, 494:1-20 (2001).

Hodge et al. "The halogenation of methyl pyrrole-2-carboxylate and of some related pyrroles" Journal of the Chemical Society, pp. 459-470 (1965).

Hu et al. "Ferrocenyl Derivatives with One, Two, or Three Sulfur-Containing Arms for Self-Assembled Monolayer Formation" The Journal of Organic Chemistry, 65(8):2277-2281 (2000).

International Preliminary Report on Patentability corresponding to International Patent Application No. PCT/US2017/047266 (8 pages) (dated Feb. 28, 2019).

Jacobi et al. "Studies on Corrin Synthesis. A Solution to the Introduction of Meso Substituents" The Journal of Organic Chemistry, 64(6):1778-1779 (1999).

Jacobi et al. "A New Synthesis of Chlorins" Organic Letters, 3(6):831-834 (2001).

Kim et al. "De Novo Synthesis of Stable Tetrahydroporphyrinic Macrocycles: Bacteriochlorins and a Tetradehydrocorrin" The Journal of Organic Chemistry, 70:5475-5486 (2005).

Krayer et al. "Expanded Scope of Synthetic Bacteriochlorins via Improved Acid Catalysis Conditions and Diverse Dihydrodipyrrin-Acetals" The Journal of Organic Chemistry, 75(4):1016-1039 (2010).

Lindsey, Jonathan S. "De Novo Synthesis of Gem-Dialkyl Chlorophyll Analogues for Probing and Emulating Our Green World" Chemical Reviews, 115(13):6534-6620 (2015).

Minehan et al. "Revised Structure of Tolyporphin A" Angewandte Chemie International Edition, 38(7):926-928 (1999).

Minehan et al. "Total Synthesis of the Proposed Structure of (+)-Tolyporphin A O,O-Diacetate" Angewandte Chemie International Edition, 38(7):923-925 (1999).

Nikitin et al. "Synthesis of tripodal [2]rotaxanes: high concentration principle" Chemical Communications, 2:282-283 (2003).

O'Neal et al. "Studies in Chlorin Chemistry. 3. A Practical Synthesis of C,D-Ring Symmetric Chlorins of Potential Utility in Photodynamic Therapy" The Journal of Organic Chemistry, 71(9):3472-3480 (2006).

Paajanen et al. "Proton Relaxation Enhancement of Albumin, Immunoglobulin G, and Fibrinogen Labeled with Gd-DTPA" Magnetic Resonance in Medicine, 13(1):38-43 (1990).

Pykett, Ian L. "NMR Imaging in Medicine" Scientific American, 246(5):78-91 (1982).

Reddy et al. "Synthetic bacteriochlorins with integral spiro-piperidine motifs" New Journal of Chemistry, 37(4):1157-1173 (2013).

Runge et al. "Paramagnetic Agents for Contrast-Enhanced NMR Imaging: A Review" American Journal of Roentgenology, 141(6):1209-1215 (1983).

Siiman et al. "Tris(3-mercaptopropyl-N-glycylmainomethane as a new linker to bridge antibody with metal particles for biological cell separations" Bioconjugate Chemistry, 11(4):549-556 (2000).

Taniguchi et al. "Synthesis of Meso-Substituted Chlorins via Tetrahydrobilene-a Intermediates" The Journal of Organic Chemistry, 66(22):7342-7354 (2001).

(56) References Cited

OTHER PUBLICATIONS

Trost et al. "New Class of Nucleophiles for Palladium-Catalyzed Asymmetric Allylic Alkylation. Total Synthesis of Agelastatin A" Journal of the American Chemical Society, 128(18):6054-6055 (2006).
Umemura et al. "Recent advances in sonodynamic approach to cancer therapy" Ultrasonics Sonochemistry, 3(3): S187-S191 (1996).
Whitesell et al. "Directionally Aligned Helical Peptides on Surfaces" Science, 261:73-76 (1993).
Whitlock et al. "Diimide Reduction of Porphyrins" Journal of the American Chemical Society, 91(26):7485-7489 (1969).
Yao et al. "Facile Convergent Route to Molecular Caltrops" The Journal of Organic Chemistry, 64(6):1968-1971 (1999).
Yoshida et al. "Hybridoma Produces Protective Antibodies Directed against the Sporozoite Stage of Malaria Parasite" Science, 207(4426):71-73 (1980).
Yu et al. "Excited-State Energy-Transfer Dynamics in Self-Assembled Triads Composed of Two Porphyrins and an Intervening Bis(dipyrrinato)metal Complex" Inorganic Chemistry, 42(21):6629-6647 (2003).
Yumita et al. "The Combination Treatment of Ultrasound and Antitumor Drugs on Yoshida Sarcoma" Japanese Journal of Hyperthermic Oncology, 3(2):175-182 (1987).
Yumita et al. "Sonodynamically induced antitumor effect of gallium-porphyrin complex by focused ultrasound on experimental kidney tumor" Cancer Letters, 112:79-86 (1997).
Bonnett et al. "Opp-Dibenzoporphyrins from Benzopyrromethene Derivatives" Journal of the Chemical Society, 9:1129-1130 (1994).
Bonnett et al. "Approaches to the stepwise synthesis of benzoporphyrins and phthalocyanines. Part 1. Synthesis of opp-dibenzoporphyrins (dibenzo[g,q]porphyrins)" Journal of the Chemical Society, Perkin Transactions 1, 20:2461-2466 (1996).
Borbas et al. "Swallowtail Bacteriochlorins. Lipophilic Absorbers for the Near-Infrared" Organic Letters, 10(10):1931-1934 (2008).
Boudif et al. "Vic-Diacrylic ester porphyrins as starting materials for monobenzoporphyrin and -dibenzoporphyrin synthesis" Canadian Journal of Chemistry, 76:1215-1219 (1998).
Chen et al. "Synthesis and Physicochemical Properties of Metallobacteriochlorins" Inorganic Chemistry, 51:9443-9464 (2012).
De Assis et al. "NIR bacteriochlorin chromophores accessed by Heck and Sonogashira cross-coupling reactions on a tetrabromobacteriochlorin derivative" Organic & Biomolecular Chemistry, 14:1402-1412 (2016).
Deshpande et al. "Opp-Dibenzoporphyrins as a Light-Harvester for Dye-Sensitized Solar Cells" Chemistry—An Asian Journal, 7:2662-2669 (2012).
Fukuda et al. "Synthesis and Spectroscopic and Electrochemical Studies of Novel Benzo- or 2,3-Naphtho-Fused Tetraazachlorins, Bacteriochlorins, and Isobacteriochlorins" Chemistry—A European Journal, 10:117-133 (2004).
International Search Report and the Written Opinion of the International Searching Authority corresponding to International Patent Application No. PCT/US2017/047266 (11 pages) (dated Dec. 28, 2017).
Krayer et al. "Synthesis and Photophysical Characterization of Stable Indium Bacteriochlorins" Inorganic Chemistry, 50:4607-4618 (2011).
Lee et al. "Sulfolenoporphyrins: synthons for refunctionalization of porphyrins" Tetrahedron Letters, 46:2009-2013 (2005).
Silva et al. "Chemical Transformations of Mono- and Bis(buta-1,3-dien-1-yl)porphyrins: A New Synthetic Approach to Mono- and Dibenzoporphyrins" European Journal of Organic Chemistry, 4:704-712 (2008).
Taniguchi et al. "Accessing the near-infrared spectral region with stable, synthetic, wavelength-tunable bacteriochlorins" New Journal of Chemistry, 32:947-958 (2008).

\* cited by examiner

NORTHERN-SOUTHERN ROUTE TO SYNTHESIS OF BACTERIOCHLORINS

RELATED APPLICATION INFORMATION

This application claims the benefit of U.S. Provisional Patent Application Ser. No. 62/376,078, filed Aug. 17, 2016, the disclosure of which is incorporated herein by reference in its entirety.

STATEMENT OF GOVERNMENT SUPPORT

This invention was made with United States government support under grant numbers DE-SC0001035 and DE-FG02-05ER15661 awarded by the Department of Energy and grant number EB020470 awarded by the National Institutes of Health. The United States government has certain rights in the invention.

FIELD OF THE INVENTION

The present invention concerns chlorins, bacteriochlorins, methods and intermediates for the synthesis of bacteriochlorins, and methods of using such bacteriochlorins for, among other things, diagnostic and therapeutic purposes such as luminescent compounds in flow cytometry, and as active agents in photodynamic therapy (PDT).

BACKGROUND OF THE INVENTION

Bacteriochlorophylls (bacteriochlorophyll a is shown in Chart 1) are the core pigments in the natural light-harvesting processes and electron-transfer reactions of anoxygenic phototrophic bacteria.[1,2] Bacteriochlorophylls feature a strong ($\varepsilon \sim 10^5$ M$^{-1}$ cm$^{-1}$) long-wavelength absorption band located in the near-infrared region (NIR),[1] normally around 700-900 nm, which enables capture of energy distinct from that of other macrocycles. The spectroscopic property of a bacteriochlorophyll is directly related to the tetrapyrrole macrocycle, termed a bacteriochlorin, which is a large heteroaromatic ring wherein two reduced pyrrole rings are located at opposite sides.

Chart 1. Natural bacteriochlorophylls and synthetic bacteriochlorins.

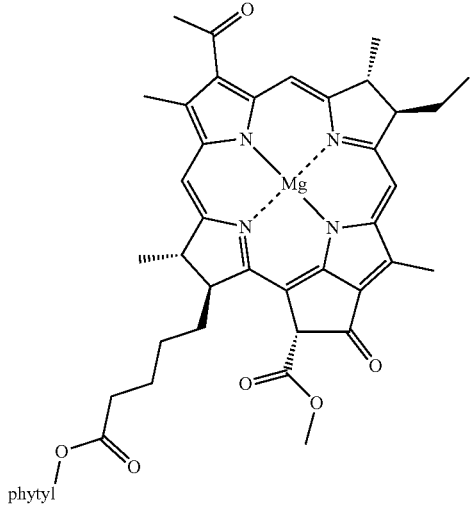

Bacteriochlorophyll a

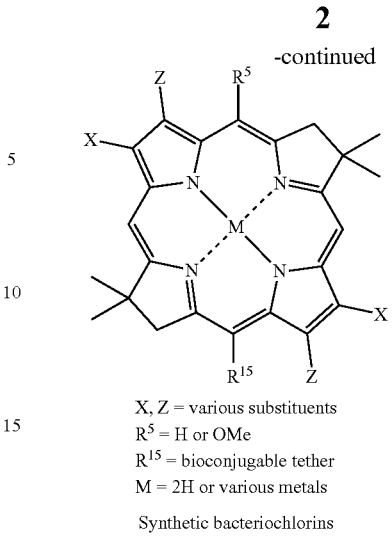

X, Z = various substituents
R$^5$ = H or OMe
R$^{15}$ = bioconjugable tether
M = 2H or various metals Synthetic bacteriochlorins Most synthetic work was focused on routes based on the biosynthesis[3] or modifications of existing natural bacteriochlorophylls and derivatization of other tetrapyrroles.[4] There are, however, a few reported de novo syntheses of stable bacteriochlorins. Overall, methodologies to construct bacteriochlorin macrocycles have been generally limited, and indeed, the total synthesis of bacteriochlorophylls has never been carried out despite success for synthetic analogues.[5]

SUMMARY OF THE INVENTION

A first aspect of the present invention is a method of making a compound of Formula I:

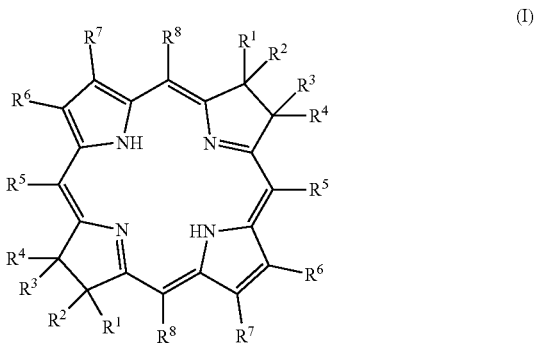

(I)

or a metal conjugate thereof, wherein:

each R$^1$, R$^2$, R$^3$, R$^4$, R$^5$, R$^6$, R$^7$ and R$^8$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or R$^1$ and R$^2$ together are =O or spiroalkyl;
or R$^3$ and R$^4$ together are =O or spiroalkyl;

or where R⁶ and R⁷, or R⁷ and R⁸, together represent a fused aromatic or heteroaromatic ring systems;

said method comprising condensing a pair of compounds of Formula II:

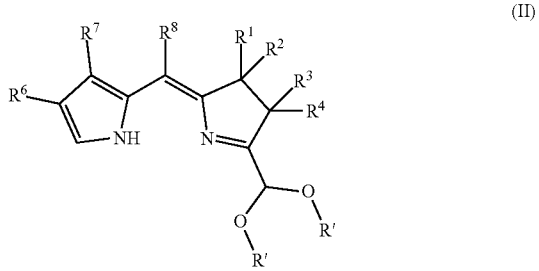

(II)

in an organic solvent in the presence of an acid, where each R' independently represents C1-C4 alkyl, or both R' together represent C2-C4 alkylene; to produce a compound of Formula I wherein R⁵ is H or alkoxy;

when R⁵ is H, optionally brominating, and then optionally further substituting said compound at the R⁵ position; and then optionally metalating said compound to produce a metal conjugate of said compound of Formula I.

Compounds of the present invention (sometimes referred to as "active compounds" herein) include compounds of Formula I, and pharmaceutically acceptable salts, prodrugs and conjugates (such as metal conjugates) thereof.

A further aspect of the present invention is, in a method of detecting particles such as cells by flow cytometry, where the particles are labelled with a detectable luminescent compound, the improvement comprising utilizing a bacteriochlorin as described herein as the luminescent compound.

A further aspect of the invention is a method for treating a target in a subject in need thereof, comprising: (i) administering to the subject the active compound as described herein or a pharmaceutically acceptable conjugate thereof that preferentially associates with the target, and (ii) irradiating the target with light of a wavelength and intensity sufficient to treat the target. Suitable subjects include but are not limited to subjects afflicted with opportunistic infections, with burns (particularly burns that have become infected), sepsis, with ulcers, periodontal disease, atherosclerosis, cosmetic and dermatologic conditions, acne, infectious diseases, tissues that require sealing such as in wounds or surgical incisions, and subjects afflicted with neoplastic disease or cancer.

A further aspect of the invention is a photodynamic therapy method for treating hyperproliferative tissue in a subject in need thereof, comprising: (i) administering to the subject an active compound as described herein or a pharmaceutically acceptable conjugate thereof that preferentially associates with the hyperproliferative tissue, and (ii) irradiating the target with light of a wavelength and intensity sufficient to activate the compound, and thereby treat the hyperproliferative tissue.

A further aspect of the invention is a method for detecting the presence of a hyperproliferative tissue in a subject, comprising: (i) administering to the subject an active compound as described herein or a pharmaceutically acceptable conjugate thereof that preferentially associates with the hyperproliferative tissue; and then (ii) visualizing the compound within the patient.

A further aspect of the present invention is a kit to treat hyperproliferative disorders, comprising the active compound described herein or a pharmaceutically acceptable conjugate thereof and instructions teaching a method of photodynamic therapy.

A further aspect of the present invention is a kit to label specific tissues for diagnosis comprising the active compound described herein or a pharmaceutically acceptable conjugate thereof and instructions teaching a method of imaging (e.g., magnetic resonance imaging).

The foregoing and other objects and aspects of the invention are explained in greater detail in the drawings herein and the specification set forth below.

DETAILED DESCRIPTION OF EXAMPLE EMBODIMENTS

"Halo" as used herein refers to any suitable halogen, including —F, —Cl, —Br, and —I.

"Mercapto" as used herein refers to an —SH group.

"Azido" as used herein refers to an —N₃ group.

"Cyano" as used herein refers to a —CN group.

"Hydroxyl" as used herein refers to an —OH group.

"Nitro" as used herein refers to an —NO₂ group.

"Alkyl" as used herein alone or as part of another group, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" as used herein, is a subset of alkyl, in some embodiments preferred, and refers to a straight or branched chain hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "akyl" or "loweralkyl" is intended to include both substituted and unsubstituted alkyl or loweralkyl unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy (thereby creating a polyalkoxy such as polyethylene glycol), alkenyloxy, alkynyloxy, haloalkoxy, cycloalkoxy, cycloalkylalkyloxy, aryloxy, arylalkyloxy, heterocyclooxy, heterocycloalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, carboxy, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3.

"Alkenyl" as used herein alone or as part of another group, refers to a straight or branched chain hydrocarbon containing from 1 to 10 carbon atoms (or in loweralkenyl 1 to 4 carbon atoms) which include 1 to 4 double bonds in the normal chain. Representative examples of alkenyl include, but are not limited to, vinyl, 2-propenyl, 3-butenyl, 2-butenyl, 4-pentenyl, 3-pentenyl, 2-hexenyl, 3-hexenyl, 2,4-heptadiene, and the like. The term "alkenyl" or "loweralkenyl" is intended to include both substituted and unsubstituted alkenyl or loweralkenyl unless otherwise indicated and these groups may be substituted with groups as described in connection with alkyl and loweralkyl above.

"Alkynyl" as used herein alone or as part of another group, refers to a straight or branched chain hydrocarbon containing from 1 to 10 carbon atoms (or in loweralkynyl 1 to 4 carbon atoms) which include 1 triple bond in the normal chain. Representative examples of alkynyl include, but are not limited to, 2-propynyl, 3-butynyl, 2-butynyl, 4-pentynyl, 3-pentynyl, and the like. The term "alkynyl" or "loweralkynyl" is intended to include both substituted and unsubstituted alkynyl or loweralknynyl unless otherwise indicated and these groups may be substituted with the same groups as set forth in connection with alkyl and loweralkyl above.

"Alkoxy" as used herein alone or as part of another group, refers to an alkyl or loweralkyl group, as defined herein (and thus including substituted versions such as polyalkoxy), appended to the parent molecular moiety through an oxy group, —O—. Representative examples of alkoxy include, but are not limited to, methoxy, ethoxy, propoxy, 2-propoxy, butoxy, tert-butoxy, pentyloxy, hexyloxy and the like.

"Acyl" as used herein alone or as part of another group refers to a —C(O)R radical, where R is any suitable substituent such as aryl, alkyl, alkenyl, alkynyl, cycloalkyl or other suitable substituent as described herein.

"Haloalkyl" as used herein alone or as part of another group, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Alkylthio" as used herein alone or as part of another group, refers to an alkyl group, as defined herein, appended to the parent molecular moiety through a thio moiety, as defined herein. Representative examples of alkylthio include, but are not limited, methylthio, ethylthio, tert-butylthio, hexylthio, and the like.

"Aryl" as used herein alone or as part of another group, refers to a monocyclic carbocyclic ring system or a bicyclic carbocyclic fused ring system having one or more aromatic rings. Representative examples of aryl include, azulenyl, indanyl, indenyl, naphthyl, phenyl, tetrahydronaphthyl, and the like. The term "aryl" is intended to include both substituted and unsubstituted aryl unless otherwise indicated and these groups may be substituted with the same groups as set forth in connection with alkyl and loweralkyl above.

"Arylalkyl" as used herein alone or as part of another group, refers to an aryl group, as defined herein, appended to the parent molecular moiety through an alkyl group, as defined herein. Representative examples of arylalkyl include, but are not limited to, benzyl, 2-phenylethyl, 3-phenylpropyl, 2-naphth-2-ylethyl, and the like.

"Amino" as used herein means the radical —$NH_2$.

"Alkylamino" as used herein alone or as part of another group means the radical —NHR, where R is an alkyl group.

"Arylalkylamino" as used herein alone or as part of another group means the radical —NHR, where R is an arylalkyl group.

"Disubstituted-amino" as used herein alone or as part of another group means the radical —$NR_aR_b$, where $R_a$ and $R_b$ are independently selected from the groups alkyl, haloalkyl, alkenyl, alkynyl, cycloalkyl, cycloalkylalkyl, aryl, arylalkyl, heterocyclo, and heterocycloalkyl.

"Acylamino" as used herein alone or as part of another group means the radical —$NR_aR_b$, where $R_a$ is an acyl group as defined herein and $R_b$ is selected from the groups hydrogen, alkyl, haloalkyl, alkenyl, alkynyl, cycloalkyl, cycloalkylalkyl, aryl, arylalkyl, heterocyclo, and heterocycloalkyl.

"Acyloxy" as used herein alone or as part of another group means the radical —OR, where R is an acyl group as defined herein.

"Ester" as used herein alone or as part of another group refers to a —C(O)OR radical, where R is any suitable substituent such as alkyl, cycloalkyl, alkenyl, alkynyl or aryl.

"Formyl" as used herein refers to a —C(O)H group.

"Carboxylic acid" as used herein refers to a —C(O)OH group.

"Sulfoxyl" as used herein refers to a compound of the formula —S(O)R, where R is any suitable substituent such as alkyl, cycloalkyl, alkenyl, alkynyl or aryl.

"Sulfonyl as used herein refers to a compound of the formula —S(O)(O)R, where R is any suitable substituent such as alkyl, cycloalkyl, alkenyl, alkynyl or aryl.

"Sulfonate" as used herein refers to a compound of the formula —S(O)(O)OR, where R is any suitable substituent such as alkyl, cycloalkyl, alkenyl, alkynyl or aryl.

"Sulfonic acid as used herein refers to a compound of the formula —S(O)(O)OH.

"Amide" as used herein alone or as part of another group refers to a —C(O)$NR_aR_b$ radical, where $R_a$ and $R_b$ are any suitable substituent such as alkyl, cycloalkyl, alkenyl, alkynyl or aryl.

"Sulfonamide" as used herein alone or as part of another group refers to a —S(O)$_2NR_aR_b$ radical, where $R_a$ and $R_b$ are any suitable substituent such as H, alkyl, cycloalkyl, alkenyl, alkynyl or aryl.

"Urea" as used herein alone or as part of another group refers to an —N($R_c$)C(O)$NR_aR_b$ radical, where $R_a$, $R_b$ and $R_c$ are any suitable substituent such as H, alkyl, cycloalkyl, alkenyl, alkynyl or aryl.

"Alkoxyacylamino" as used herein alone or as part of another group refers to an —N($R_a$)C(O)$OR_b$ radical, where $R_a$, $R_b$ are any suitable substituent such as H, alkyl, cycloalkyl, alkenyl, alkynyl or aryl.

"Aminoacyloxy" as used herein alone or as part of another group refers to an —OC(O)$NR_aR_b$ radical, where $R_a$ and $R_b$ are any suitable substituent such as H, alkyl, cycloalkyl, alkenyl, alkynyl or aryl.

"Cycloalkyl" as used herein alone or as part of another group, refers to a saturated or partially unsaturated cyclic hydrocarbon group containing from 3, 4 or 5 to 6, 7 or 8 carbons (which carbons may be replaced in a heterocyclic group as discussed below). Representative examples of cycloalkyl include, cyclopropyl, cyclobutyl, cyclopentyl, cyclohexyl, cycloheptyl, and cyclooctyl. These rings may be optionally substituted with additional substituents as described herein such as halo or loweralkyl. The term "cycloalkyl" is generic and intended to include heterocyclic groups as discussed below unless specified otherwise.

"Heterocyclic group" or "heterocyclo" as used herein alone or as part of another group, refers to an aliphatic (e.g., fully or partially saturated heterocyclo) or aromatic (e.g., heteroaryl) monocyclic- or a bicyclic-ring system. Monocyclic ring systems are exemplified by any 5 or 6 membered ring containing 1, 2, 3, or 4 heteroatoms independently selected from oxygen, nitrogen and sulfur. The 5 membered ring has from 0-2 double bonds and the 6 membered ring has from 0-3 double bonds. Representative examples of monocyclic ring systems include, but are not limited to, azetidine, azepine, aziridine, diazepine, 1,3-dioxolane, dioxane, dithiane, furan, imidazole, imidazoline, imidazolidine, isothiazole, isothiazoline, isothiazolidine, isoxazole, isoxazoline, isoxazolidine, morpholine, oxadiazole, oxadiazoline, oxadiazolidine, oxazole, oxazoline, oxazolidine, piperazine, piperidine, pyran, pyrazine, pyrazole, pyrazoline, pyrazolidine, pyridine, pyrimidine, pyridazine, pyrrole, pyrroline, pyrrolidine, tetrahydrofuran, tetrahydrothiophene, tetrazine, tetrazole, thiadiazole, thiadiazoline, thiadiazolidine, thiazole, thiazoline, thiazolidine, thiophene, thiomorpholine, thiomorpholine sulfone, thiopyran, triazine, triazole, trithiane, and the like. Bicyclic ring systems are exemplified by any of the above monocyclic ring systems fused to an aryl group as defined herein, a cycloalkyl group as defined herein, or another monocyclic ring system as defined herein. Representative examples of bicyclic ring systems include but are not limited to, for example, benzimidazole, benzothiazole, benzothiadiazole, benzothiophene, benzoxadiazole, benzoxazole, benzofuran, benzopyran, benzothiopyran, benzodioxine, 1,3-benzodioxole, cinnoline, indazole, indole, indoline, indolizine, naphthyridine, isobenzofuran, isobenzothiophene, isoindole, isoindoline, isoquinoline, phthalazine, purine, pyranopyridine, quinoline, quinolizine, quinoxaline, quinazoline, tetrahydroisoquinoline, tetrahydroquinoline, thiopyranopyridine, and the like. These rings include quaternized derivatives thereof and may be optionally substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1, 2 or 3. Preferred heterocyclo groups include pyridyl and imidazolyl groups, these terms including the the quaternized derivatives thereof, including but not limited to quaternary pyridyl and imidazolyl groups, examples of which include but are not limited to:

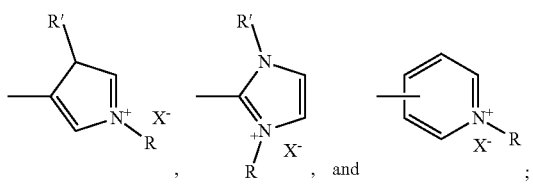

where R and R' are each a suitable substituent as described in connection with "alkyl" above, and particularly alkyl (such as methyl, ethyl or propyl), arylalkyl (such as benzyl), optionally substituted with hydroxy (—OH), phosphonic acid (—PO$_3$H$_2$) or sulfonic acid (—SO$_3$H), and X⁻ is a counterion.

"Spiroalkyl" as used herein alone or as part of another group, refers to a straight or branched chain hydrocarbon, saturated or unsaturated, containing from 3 to 8 carbon atoms. Representative examples include, but are not limited to, —CH$_2$CH$_2$CH$_2$—, —CH$_2$CH$_2$CH$_2$CH$_2$—, —CH$_2$CH$_2$CH$_2$CH$_2$CH$_2$—, —CH$_2$CH$_2$CHCHCH$_2$—, —CH$_2$CH$_2$CH$_2$CH$_2$CH$_2$CH$_2$—, etc. The term "spiroalkyl" is intended to include both substituted and unsubstituted "spiroalkyl" unless otherwise indicated and these groups may be substituted with groups selected from halo, alkyl, haloalkyl, alkenyl, alkynyl, cycloalkyl, cycloalkylalkyl, aryl, arylalkyl, heterocyclo, heterocycloalkyl, hydroxyl, alkoxy, alkenyloxy, alkynyloxy, haloalkoxy, cycloalkoxy, cycloalkylalkyloxy, aryloxy, arylalkyloxy, heterocyclooxy, heterocyclolalkyloxy, mercapto, alkyl-S(O)$_m$, haloalkyl-S(O)$_m$, alkenyl-S(O)$_m$, alkynyl-S(O)$_m$, cycloalkyl-S(O)$_m$, cycloalkylalkyl-S(O)$_m$, aryl-S(O)$_m$, arylalkyl-S(O)$_m$, heterocyclo-S(O)$_m$, heterocycloalkyl-S(O)$_m$, amino, alkylamino, alkenylamino, alkynylamino, haloalkylamino, cycloalkylamino, cycloalkylalkylamino, arylamino, arylalkylamino, heterocycloamino, heterocycloalkylamino, disubstituted-amino, acylamino, acyloxy, ester, amide, sulfonamide, urea, alkoxyacylamino, aminoacyloxy, nitro or cyano where m=0, 1 or 2.

"Treatment" as used herein means any manner in which one or more of the symptoms of a disease or disorder are ameliorated or otherwise beneficially altered. Treatment also encompasses any pharmaceutical use of the compositions herein, such as use for treating hyperproliferating tissue or neovascularization mediated diseases or disorders, or diseases or disorders in which hyperproliferating tissue or neovascularization is implicated. As used herein, amelioration of the symptoms of a particular disorder by administration of a particular compound or pharmaceutical composition refers to any lessening, whether permanent or temporary, lasting or transient that can be attributed to or associated with administration of the composition.

"Prodrug" as used herein is a compound that, upon in vivo administration, is metabolized by one or more steps or processes or otherwise converted to the biologically, pharmaceutically or therapeutically active form of the compound.

"Antibody" as used herein refers generally to immunoglobulins or fragments thereof that specifically bind to antigens to form immune complexes. The antibody may be whole immunoglobulin of any class, e.g., IgG, IgM, IgA, IgD, IgE, chimeric or hybrid antibodies with dual or multiple antigen or epitope specificities. It can be a polyclonal antibody, preferably an affinity-purified antibody from a human or an appropriate animal, e.g., a primate, goat, rabbit, mouse or the like. Monoclonal antibodies are also suitable for use in the present invention, and are preferred because of their high specificities. They are readily prepared by what are now considered conventional procedures of immunization of mammals with immunogenic antigen preparation, fusion of immune lymph or spleen cells with an immortal myeloma cell line, and isolation of specific hybridoma clones. More unconventional methods of preparing monoclonal antibodies are not excluded, such as interspecies fusions and genetic engineering manipulations of hypervariable regions, since it is primarily the antigen specificity of the antibodies that affects their utility. Newer techniques for production of monoclonals can also be used, e.g., human monoclonals, interspecies monoclonals, chimeric (e.g., human/mouse) monoclonals, genetically engineered antibodies and the like.

"Infecting agent" as used herein denotes invading microbes or parasites. As used herein, "microbe" denotes virus, bacteria, *rickettsia, mycoplasma*, protozoa, fungi and like microorganisms, and "parasite" denotes infectious, generally microscopic or very small multicellular invertebrates, or ova or juvenile forms thereof, which are susceptible to antibody-induced clearance or lytic or phagocytic destruction, e.g., malarial parasites, spirochetes and the like.

"Tumor" as used herein denotes a neoplasm, and includes both benign and malignant tumors. This term particularly includes malignant tumors which can be either solid (such as a breast, liver, or prostate carcinoma) or non-solid (such as a leukemia). Tumors can also be further divided into subtypes, such as adenocarcinomas (e.g. of the breast, prostate or lung).

"Target" as used herein denotes the object that is intended to be detected, diagnosed, impaired or destroyed by the methods provided herein, and includes target cells, target tissues, and target compositions. "Target tissues" and "target cells" as used herein are those tissues that are intended to be impaired or destroyed by this treatment method. Photosensitizing compounds bind to or collect in these target tissues or target cells; then when sufficient radiation is applied, these tissues or cells are impaired or destroyed. Target cells are cells in target tissue, and the target tissue includes, but is not limited to, vascular endothelial tissue, abnormal vascular walls of tumors, solid tumors such as (but not limited to) tumors of the head and neck, tumors of the eye, tumors of the gastrointestinal tract, tumors of the liver, tumors of the breast, tumors of the prostate, tumors of the lung, nonsolid tumors and malignant cells of the hematopoietic and lymphoid tissue, neovascular tissue, other lesions in the vascular system, bone marrow, and tissue or cells related to autoimmune disease. Also included among target cells are cells undergoing substantially more rapid division as compared to non-target cells.

"Non-target tissues" as used herein are all the tissues of the subject which are not intended to be impaired or destroyed by the treatment method. These non-target tissues include but are not limited to healthy blood cells, and other normal tissue, not otherwise identified to be targeted.

"Target compositions" as used herein are those compositions that are intended to be impaired or destroyed by this treatment method, and may include one or more pathogenic agents, including but not limited to bacteria, viruses, fungi, protozoa, and toxins as well as cells and tissues infected or infiltrated therewith. The term "target compositions" also includes, but is not limited to, infectious organic particles such as prions, toxins, peptides, polymers, and other compounds that may be selectively and specifically identified as an organic target that is intended to be impaired or destroyed by this treatment method.

"Hyperproliferative tissue" as used herein means tissue that grows out of control and includes neoplastic tissue, tumors and unbridled vessel growth such as blood vessel growth found in age-related macular degeneration and often occurring after glaucoma surgeries.

"Hyperproliferative disorders" as used herein denotes those conditions disorders sharing as an underlying pathology excessive cell proliferation caused by unregulated or abnormal cell growth, and include uncontrolled angiogenesis. Examples of such hyperproliferative disorders include, but are not limited to, cancers or carcinomas, acute and membrano-proliferative glomerulonephritis, myelomas, psoriasis, atherosclerosis, psoriatic arthritis, rheumatoid arthritis, diabetic retinopathies, macular degeneration, corneal neovascularization, choroidal hemangioma, recurrence of pterygii, and scarring from excimer laser surgery and glaucoma filtering surgery.

"Therapeutically effective dose" as used herein is a dose sufficient to prevent advancement, or to cause regression of the disease, or which is capable of relieving symptoms caused by the disease.

"Irradiating" and "irradiation" as used herein includes exposing a subject to all wavelengths of light. Preferably, the irradiating wavelength is selected to match the wavelength(s) which excite the photosensitive compound. Preferably, the radiation wavelength matches the excitation wavelength of the photosensitive compound and has low absorption by the non-target tissues of the subject, including blood proteins.

Irradiation is further defined herein by its coherence (laser) or non-coherence (non-laser), as well as intensity, duration, and timing with respect to dosing using the photosensitizing compound. The intensity or fluence rate must be sufficient for the light to reach the target tissue. The duration or total fluence dose must be sufficient to photoactivate enough photosensitizing compound to act on the target tissue. Timing with respect to dosing with the photosensitizing compound is important, because 1) the administered photosensitizing compound requires some time to home in on target tissue and 2) the blood level of many photosensitizing compounds decreases with time. The radiation energy is provided by an energy source, such as a laser or cold cathode light source, that is external to the subject, or that is implanted in the subject, or that is introduced into a subject, such as by a catheter, optical fiber or by ingesting the light source in capsule or pill form (e.g., as disclosed in. U.S. Pat. No. 6,273,904 (2001)).

While one preferred embodiment of the present invention is drawn to the use of light energy for administering photodynamic therapy (PDT) to destroy tumors, other forms of energy are within the scope of this invention, as will be understood by those of ordinary skill in the art. Such forms of energy include, but are not limited to: thermal, sonic, ultrasonic, chemical, light, microwave, ionizing (such as x-ray and gamma ray), mechanical, and electrical. For example, sonodynamically induced or activated agents include, but are not limited to: gallium-porphyrin complex (see Yumita et al., Cancer Letters 112: 79-86 (1997)), other porphyrin complexes, such as protoporphyrin and hematoporphyrin (see Umemura et al., Ultrasonics Sonochemistry 3: S187-S191 (1996)); other cancer drugs, such as daunorubicin and adriamycin, used in the presence of ultrasound therapy (see Yumita et al., Japan J. Hyperthermic Oncology 3(2):175-182 (1987)).

"Coupling agent" as used herein, refers to a reagent capable of coupling a photosensitizer to a targeting agent "Targeting group" refers to a compound that homes in on or preferentially associates or binds to a particular tissue, receptor, infecting agent or other area of the body of the subject to be treated, such as a target tissue or target composition, such as described above. Examples of a targeting group or agent include but are not limited to an antibody, a ligand, one member of a ligand-receptor binding pair, nucleic acids, proteins and peptides, and liposomal suspensions, including tissue-targeted liposomes.

"Specific binding pair" and "ligand-receptor binding pair" as used herein refers to two different molecules, where one of the molecules has an area on the surface or in a cavity which specifically attracts or binds to a particular spatial or polar organization of the other molecule, causing both molecules to have an affinity for each other. The members of the specific binding pair are referred to as ligand and receptor (anti-ligand). The terms ligand and receptor are intended to encompass the entire ligand or receptor or portions thereof sufficient for binding to occur between the ligand and the receptor. Examples of ligand-receptor binding pairs include, but are not limited to, hormones and hormone receptors, for example epidermal growth factor and epidermal growth factor receptor, tumor necrosis factor-.alpha. and tumor necrosis factor-receptor, and interferon and interferon receptor; avidin and biotin or antibiotin; antibody and antigen pairs; enzymes and substrates, drug and drug receptor; cell-surface antigen and lectin; two complementary nucleic acid strands; nucleic acid strands and complementary oligonucleotides; interleukin and interleukin receptor; and stimulating factors and their receptors, such as granulocyte-macrophage colony stimulating factor (GMCSF) and GMCSF receptor and macrophage colony stimulating factor (MCSF) and MCSF receptor.

"Linkers" are aromatic or aliphatic groups (which may be substituted or unsubstituted and may optionally contain heteroatoms such as N, O, or S) that are utilized to couple a bioconjugatable group, cross-coupling group, surface attachment group, hydrophilic group or the like to the parent molecule. Examples include but are not limited to aryl, alkyl, heteroaryl, heteroalkyl (e.g., oligoethylene glycol), peptide, and polysaccharide linkers, etc.

"Biological materials" as used herein refers to both tissues (such as biopsy tissues) and cells, as well as biological fluids such as blood, urine, plasma, cerebrospinal fluid, mucus, sputum, etc.

Subjects to be treated by the methods of the present invention for diagnostic or therapeutic purposes include both human subjects and animal subjects (particularly mammalian subjects such as dogs, cats, horses, monkeys, chimpanzees, etc.) for veterinary purposes.

The disclosures of all United States Patent references cited herein are to be incorporated by reference herein as if fully set forth.

1. Compounds and Methods of Making.

As noted above, the present invention provides compounds, and methods of making compounds, of Formula I:

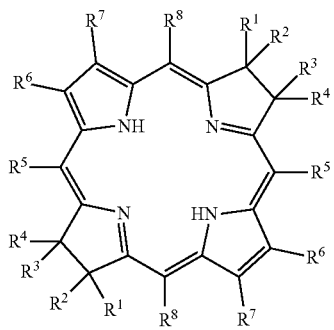

(I)

or a metal conjugate thereof, wherein:

each $R^1$, $R^2$, $R^3$, $R^4$, $R^5$, $R^6$, $R^7$ and $R^8$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or $R^1$ and $R^2$ together are =O or spiroalkyl;

or $R^3$ and $R^4$ together are =O or spiroalkyl;

or where $R^6$ and $R^7$, or $R^7$ and $R^8$, together represent a fused aromatic or heteroaromatic ring systems.

The method comprises: condensing a pair of compounds of Formula II:

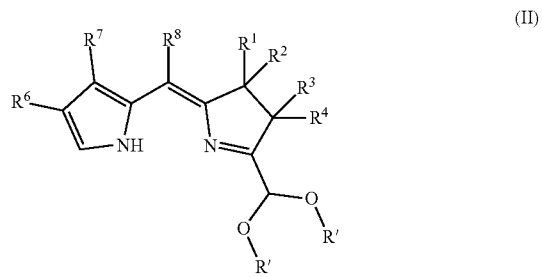

(II)

in an organic solvent in the presence of an acid, where each R' independently represents C1-C4 alkyl, or both R' together represent C2-C4 alkylene; to produce a compound of Formula I wherein $R^5$ is H or alkoxy;

when $R^5$ is H, optionally brominating, and then optionally further substituting said compound at the $R^5$ position; and then optionally metalating said compound to produce a metal conjugate of said compound of Formula I.

In some embodiments, the compound of Formula I has the structure of Formula IA or Formula IB:

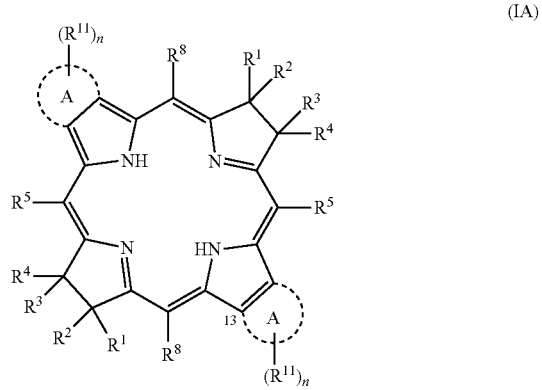

(IA)

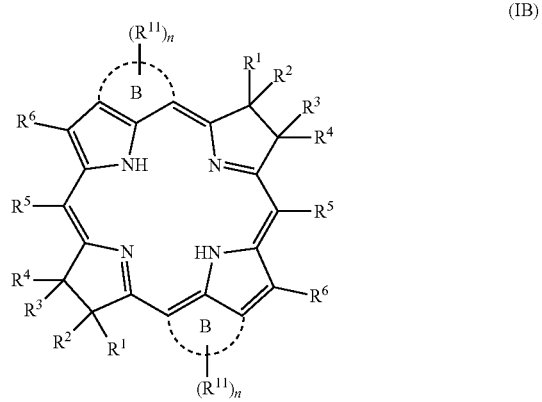

(IB)

or a metal conjugate thereof, wherein:

rings A and B represent a fused aromatic or heteroaromatic ring system (e.g., naphthalene, anthracene, phenanthrene, chrysene, pyrene, corannulene, coronene, hexahelicene, indole, isoindole, indolizine, quinoline, isoquinolene, purine, carbazole, dibenzofuran, 2H-chromene, xanthene, rylene (or "poly(peri-naphthalene)," e.g., perylene, terrylene, quarterrylene, etc.), each of which may be unsubstituted or substituted from 1, 2 or 3 to 4, 5 or 6 or more independently selected substituents from the same group as given above);

n is from 1 or 2 to 4, 6 or 8; and each $R^1$, $R^2$, $R^3$, $R^4$, $R^5$, $R^6$, $R^7R^8$ and $R^{11}$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or $R^1$ and $R^2$ together are =O or spiroalkyl;

or $R^3$ and $R^4$ together are =O or spiroalkyl.

In some embodiments, the compound of Formula II has the structure:

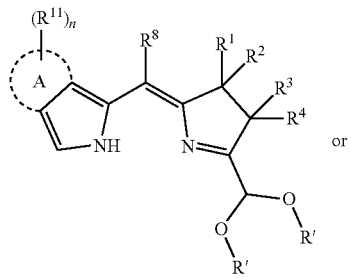

(IIA)

or

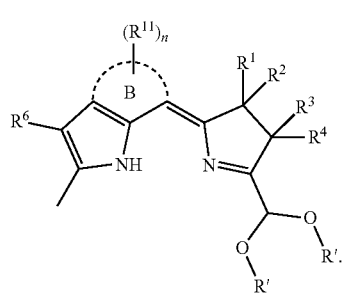

(IIB)

In some embodiments, the compound of Formula I has a structure selected from the group consisting of:

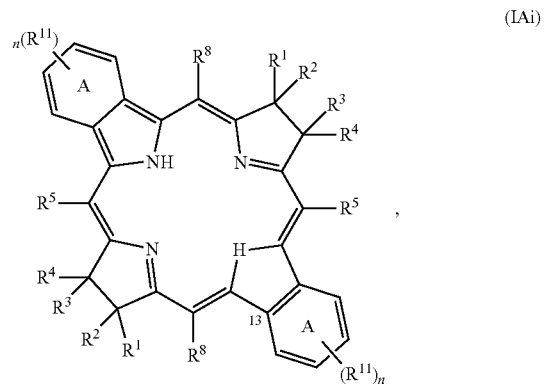

(IAi)

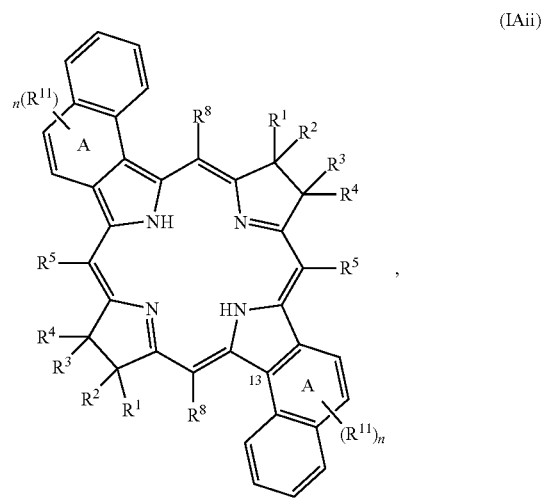

(IAii)

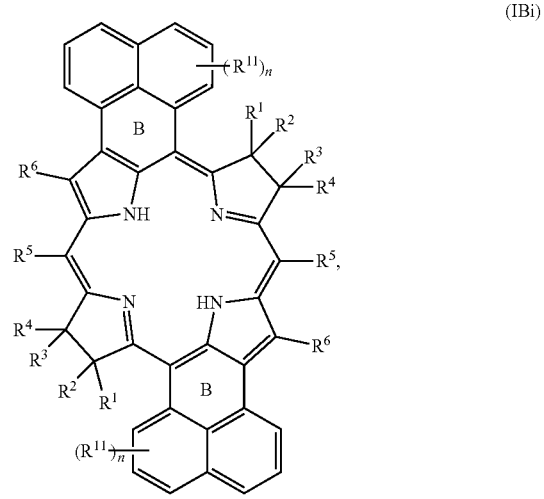

(IBi)

(IBii)
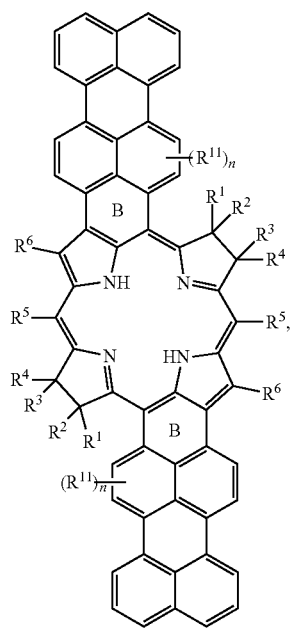
(IBiii)
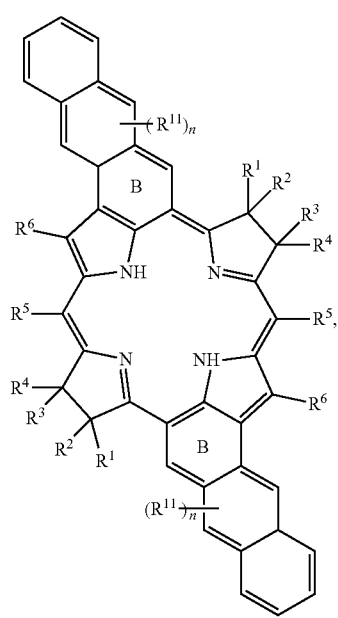
(IBiv)
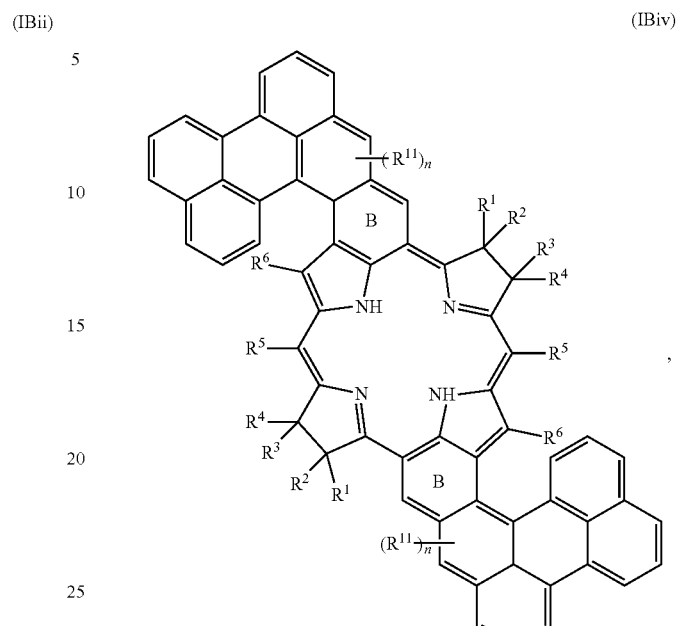
(IBv)
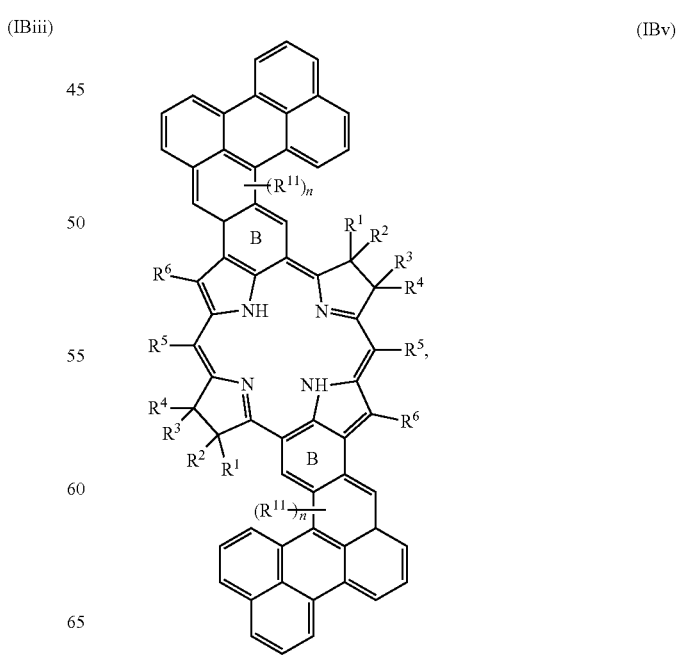

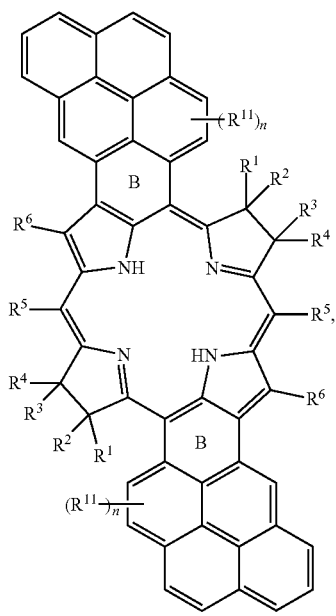
(IBvi)
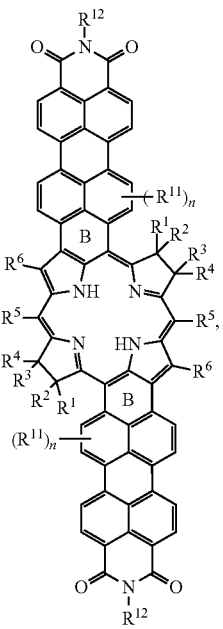
(IBviii)
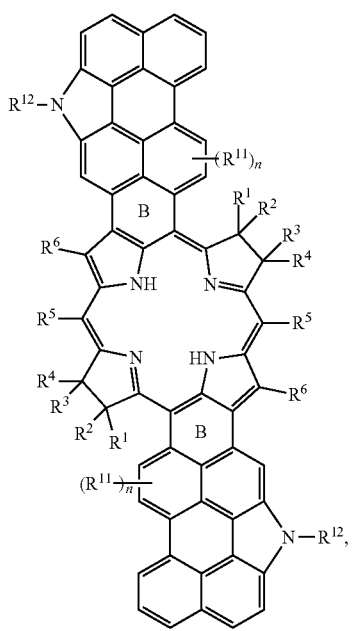
(IBvii)
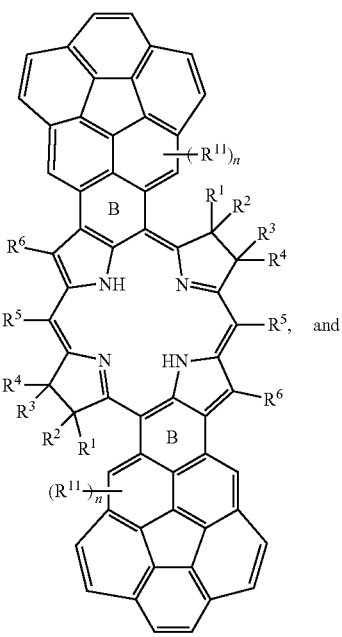
(IBix)
and

-continued (IBx)

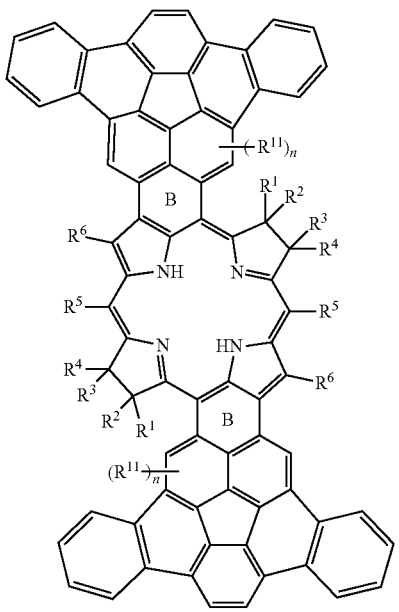

where:

n is from 1 or 2 to 4, 6 or 8;

each which may be substituted on any member ring of the corresponding ring system (A or B), is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups; and each $R^{12}$ of Formula IBvii or IBviii is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups.

In some embodiments of the foregoing, the compound of Formula II has a structure selected from the group consisting of:

(IIAi)

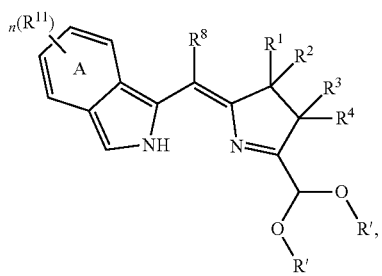

(IIAii)

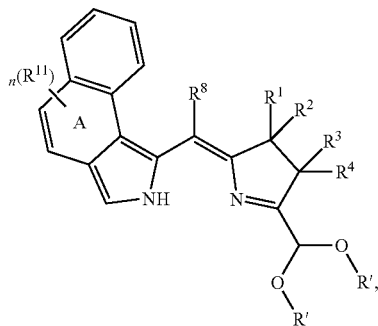

(IIBi)

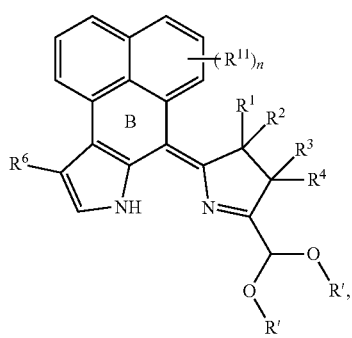

(IIBii)

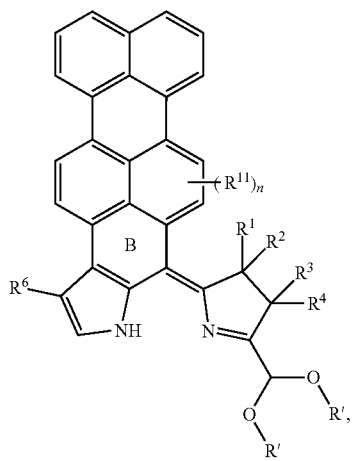

-continued
(IIBiii)
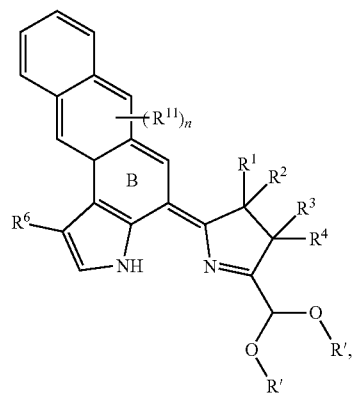
(IIBiv)
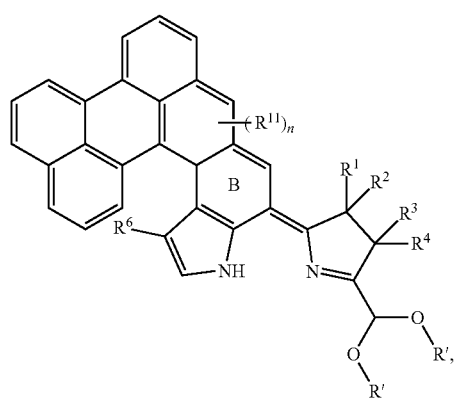
(IIBv)
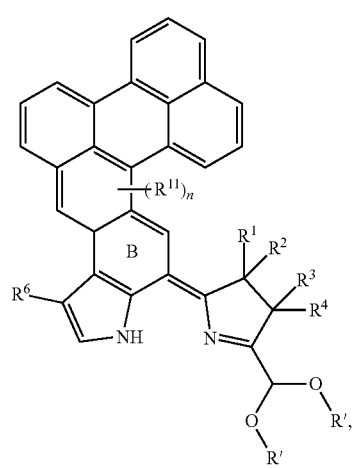
(IIBvi)
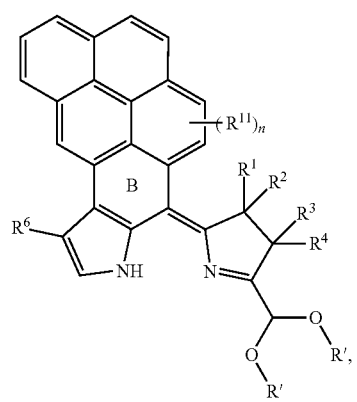
(IIBvii)
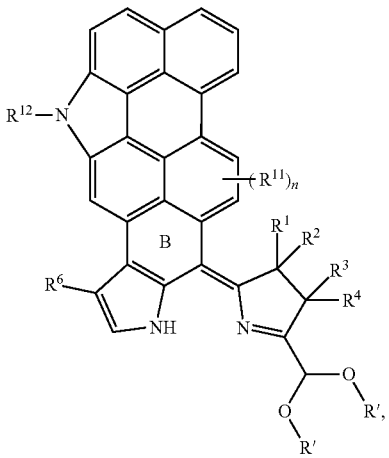
(IIBviii)
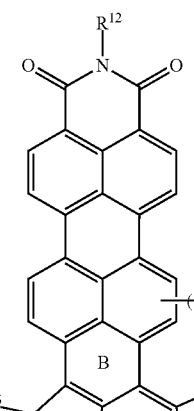
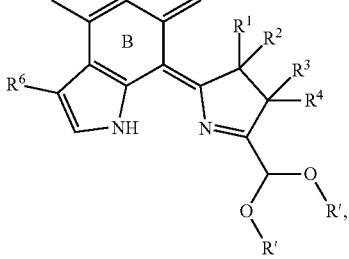
(IBix)
and

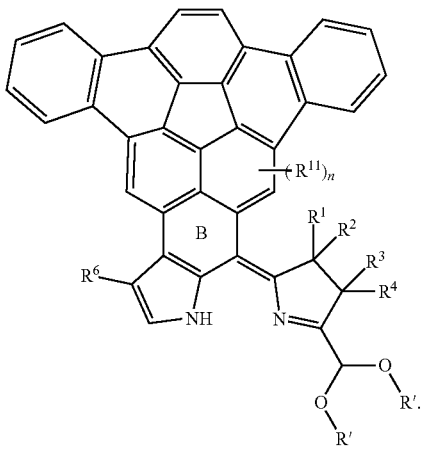

(IBx)

In some embodiments, the compound is a conjugate with a metal such as the Pd, Pt, Mg, Zn, Al, Ga, In, Sn, Cu, Ni, or Au.

In some embodiments of the foregoing, at least one of $R^1$ through $R^{12}$ comprises a linking group.

In some embodiments of the foregoing, at least one of $R^1$ to $R^{12}$ comprises a hydrophilic group.

In some embodiments of the foregoing, at least one of $R^1$ to $R^{12}$ comprises a targeting group (e.g., a protein, peptide, antibody, nucleic acid, etc.).

In some embodiments of the foregoing: each $R^1$ comprises a hydrophilic group, and each $R^2$, $R^3$, and/or $R^4$ comprises a linking group or targeting group; or each $R^2$ comprises a hydrophilic group, and each $R^1$, $R^3$, and/or $R^4$ comprises a linking group or targeting group; or each $R^3$ comprises a hydrophilic group, and each $R^1$, $R^2$, and/or $R^4$ comprises a linking group or targeting group; or each $R^4$ comprises a hydrophilic group, and each $R^1$, $R^2$, and/or $R^3$ comprises a linking group or targeting group.

In some embodiments of the foregoing: each $R^1$ comprises a linking group or targeting group, and each $R^2$, $R^3$, and/or $R^4$ comprises a hydrophilic group; or each $R^2$ comprises a linking group or targeting group, and each $R^1$, $R^3$, and/or $R^4$ comprises a hydrophilic group; or each $R^3$ comprises a linking group or targeting group, and each $R^1$, $R^2$, and/or $R^4$ comprises a hydrophilic group; or each $R^4$ comprises a linking group or targeting group, and each $R^1$, $R^2$, and/or $R^3$ comprises a hydrophilic group.

Compounds of Formula I can be made by treating the compounds of Formula II with an acid in an organic solvent. The acid is not critical, with examples including but not limited to $BF_3$ etherate, $SnCl_4$, $InCl_3$, trifluoroacetic acid, and toluenesulfonic acid. The organic solvent is not critical with examples including but not limited to acetonitrile, methylene chloride, chloroform, tetrahydrofuran, chlorobenzene, ethanol, and combinations thereof. The reaction may be carried out at any suitable temperature, such as 0 to 100° C., and conveniently at room temperature, for any suitable time period, such as for a few minutes, 1 to 4 hours, or a day. The reaction mixture is preferably nonaqueous but need not be anhydrous, and may conveniently be carried out exposed to air.

In our previous "Eastern-Western" synthesis of bacteriochlorins (see, e.g., U.S. Pat. No. 8,664,260), the substituents at $R^8$ came from the dihydrodipyrrin-acetal; we previously had difficulty installing groups in this manner due to steric hindrance of the adjacent $R^{1,2}$ alkyl groups. In the present invention, the alkyl groups are at position $R^{3,4}$, which opens the door to carrying alkyl or aryl groups at $R^8$. In the present invention, the substituents in the bacteriochlorin at $R^5$ are alkoxy or H as dictated by the macrocycle formation chemistry of the present invention, but we can now substitute $R^5$=H by bromination and then substitution to install acyl, alkyl, aryl, ethynyl, etc. groups. Annulation to install a fused ring also can be accomplished.

In some embodiments, an annulated bacteriochlorin may be prepared using two successive Pd-coupling reactions. For example, a first (e.g., Suzuki, intermolecular) reaction of a 3,13-dibromo-8,8,18,18-tetramethylbacteriochlorin with, e.g., about two equivalents of an arene bearing adjacent halo (e.g., bromo, fluoro, etc.) and dihydroxyboryl or dialkoxyboryl groups affords the 8,8,18,18-tetramethylbacteriochlorin bearing the halo-arene attached to the 3,13-positions. The second (e.g., intramolecular) reaction closes the ring to give the beta-meso-annulated bacteriochlorin.

In some embodiments, an annulated bacteriochlorin may be prepared utilizing a Suzuki coupling reaction of a 2,3,12,13-tetrabromo-8,8,18,18-tetramethylbacteriochlorin with, e.g., about two equivalents of an arene bearing adjacent dihydroxyboryl or dialkoxyboryl groups. An example suitable substrate includes, but is not limited to, 2,3,12,13-tetrabromo-5-methoxy-8,8,18,18-tetramethylbacteriochlorin (De Assis F F, Ferreira M A B, Brocksom T J and de Oliveira K T. NIR bacteriochlorin chromophores accessed by Heck and Sonogashira cross-coupling reactions on a tetrabromobacteriochlorin derivative. Org. Biomol. Chem. 2016, 14, 1402-1412).

"Adjacent" as used herein in reference to adjacent groups of a compound (e.g., adjacent dihydroxyboryl or dialkoxyboryl groups or halo and dihydroxyboryl or dialkoxyboryl groups), includes the 1,2-positions upon circumambulating an arene (e.g., 1-dihydroxyboryl-2-bromobenzene, 2-dihydroxyboryl-3-bromonaphthalene) or the proximal positions across a point of fusion in an arene (e.g., 1-dihydroxyboryl-8-bromonaphthalene, 1-dihydroxyboryl-9-bromoanthracene).

The example methods described herein for preparing an annulated bacteriochlorin may be used with the corresponding dihydrodipyrrin precursor to a bacteriochlorin. In some embodiments, a method involving two successive Pd-coupling reactions may employ a mono-bromodihydrodipyrrin. In some embodiments, a method involving a Suzuki coupling reaction (e.g., of a 2,3,12,13-tetrabromo-8,8,18,18-tetramethylbacteriochlorin with an arene bearing adjacent dihydroxyboryl or dialkoxyboryl groups) may employ a dibromodihydrodipyrrin. In reactions involving a dipyrrin (e.g., a mono-bromodihydrodipyrrin, dibromodihydrodipyrrin, etc.), the propensity for the dipyrrin unit to chelate the palladium catalyst may be circumvented (Yu, L.; Muthukumaran, K.; Sazanovich, I. V.; Kirmaier, C.; Hindin, E.; Diers, J. R.; Boyle, P. D.; Bocian, D. F.; Holten, D.; Lindsey, J. S. Excited-State Energy-Transfer Dynamics in Self-Assembled Triads Composed of Two Porphyrins and an Intervening Bis(dipyrrinato)metal Complex. Inorg. Chem. 2003, 42, 6629-6647) by inclusion of a stoichiometric quantity of a Pd(II) reagent above that of the catalytic amount of the Pd(II) catalyst, whereupon the bis(hydrodipyrrinato)Pd(II) complex is formed during the course of the reaction. Such complexes may be readily liberated upon treatment with acid or a thiol reagent.

Once made, compounds of Formula I may be metalated with any suitable metal in accordance with known techniques. See, e.g., U.S. Pat. No. 6,208,553. Suitable metals include but are not limited to Pd(II), Pt(II), Mg(II), Zn(II), Al(III), Ga(III), In(III), Sn(IV), Cu(II), Ni(II), and Au(III). Where the metal is trivalent or tetravalent a counterion is included as necessary in accordance with known techniques.

Linking Groups for Conjugates.

Linking groups are included in compounds of Formula I to provide a reactive site for conjugation so that the compounds may be coupled to or conjugated to other groups such as proteins, peptides, targeting agents such as antibodies, polymers, particles such as nanoparticles, organic, polymeric or inorganic beads, other solid support surfaces, etc., to form additional active compounds of the invention. In general each group is attached to a linking group including a linker which can be aryl, alkyl, heteroaryl, heteroalkyl (e.g., oligoethylene glycol), peptide, polysaccharide, etc. The linking group may be simply a reactive attachment group or moiety (e.g., —R' where R' is a reactive group such as bromo), or may comprise a combination of an intervening group coupled to a reactive group (e.g., —R"R', where R' is a reactive group and R' is an intervening group such as a hydrophilic group).

For bioconjugation purposes, the choice of water-solubilizing group(s) and conjugation groups is made so as to achieve orthogonal coupling. For example, if a carboxylic acid is used for water solubility, an aldehyde might be used for bioconjugation (via reductive amination with an amino-substituted biomolecule). If a carboxylic acid is used for bioconjugation (via carbodiimide-activation and coupling with an amino-substituted biomolecule), then a complementary group can be used for water solubility (e.g., sulfonic acid, guanidinium, pyridinium). Bioconjugatable groups include amines (including amine derivatives) such as isocyanates, isothiocyanates, iodoacetamides, azides, diazonium salts, etc. acids or acid derivatives such as N-hydroxysuccinimide esters (more generally, active esters derived from carboxylic acids; e.g., p-nitrophenyl ester), acid hydrazides, etc., and other linking groups such as aldehydes, sulfonyl chlorides, sulfonyl hydrazides, epoxides, hydroxyl groups, thiol groups, maleimides, aziridines, acryloyls, halo groups, biotin, 2-Iminobiotin, etc. Linking groups such as the foregoing are known and described in U.S. Pat. Nos. 6,728,129; 6,657,884; 6,212,093; and 6,208,553.

Conjugates.

Other groups can be attached to the bacteriochlorin to form a conjugate by means of a linking group to tune or adjust the solubility properties of the bacteriochlorin, including hydrophobic groups, hydrophilic groups, polar groups, or amphipathic groups. The polar groups include carboxylic acid, sulfonic acid, guanidinium, carbohydrate, hydroxy, amino acid, pyridinium, imidazolium, etc. Such groups can be attached to substituents that are linear or branched alkyl (e.g., swallowtail), aryl, heteroaryl, heteroalkyl (e.g., oligoethylene glycol), peptide, polysaccharide, etc. Targeting groups such as antibodies, proteins, peptides, and nucleic acids may be attached by means of the linking group. Particles such as nanoparticles, glass beads, etc. may be attached by means of the linking group. Where such additional compounds are attached to form a conjugate that may be attached directly to the bacteriochlorin or attached by means of an intervening group such as a hydrophilic group, depending upon the particular linking group employed (as noted above).

Hydrophilic Groups.

Compounds of the present invention may include hydrophilic groups coupled at the linking sites noted above, e.g., covalently coupled thereto, to facilitate delivery thereof, or improve stability, in accordance with known techniques (e.g., to the N-terminus of the peptide). Suitable hydrophilic groups are typically polyols or polyalkylene oxide groups, including straight and branched-chain polyols, with particularly examples including but not limited to poly(propylene glycol), polyethylene-polypropylene glycol or poly(ethylene glycol). The hydrophilic groups may have a number average molecular weight of 20,000 to 40,000 or 60,000. Suitable hydrophilic groups and the manner of coupling thereof are known and described in, for example, U.S. Pat. Nos. 4,179,337; 5,681,811; 6,524,570; 6,656,906; 6,716,811; and 6,720,306. For example, compounds can be pegylated using a single 40,000 molecular weight polyethylene glycol moiety that is attached to the compound by means of a linking group. Suitable hydrophilic groups also include ionic or polar groups, including linear or branched alkyl groups substituted with ionic or polar groups, examples of which include but are not limited to swallowtail groups such as described in Borbas and Lindsey, U.S. Pat. No. 8,530,459.

Surface Attachment Groups.

As noted above, compounds of the invention can be substituted with a surface attachment group, which may be in protected or unprotected form. A surface attachment group may be a reactive group coupled directly to the bacteriochlorin, or coupled to the bacteriochlorin by means of an intervening linker. Linkers L can be aryl, alkyl, heteroaryl, heteroalkyl (e.g., oligoethylene glycol), peptide, polysaccharide, etc. Examples of surface attachment groups (with the reactive site or group in unprotected form) include but are not limited to alkene, alkyne, alcohol, thiol, selenyl, phosphono, telluryl, cyano, amino, formyl, halo, boryl, and carboxylic acid surface attachment groups such as:

4-carboxyphenyl, carboxymethyl, 2-carboxyethyl, 3-carboxypropyl, 2-(4-carboxyphenyl)ethynyl, 4-(2-(4-carboxyphenyl)ethynyl)phenyl, 4-carboxymethylphenyl, 4-(3-carboxypropyl)phenyl, 4-(2-(4-carboxymethylphenyl)ethynyl) phenyl; 4-hydroxyphenyl, hydroxymethyl, 2-hydroxyethyl, 3-hydroxypropyl, 2-(4-hydroxyphenyl)ethynyl, 4-(2-(4-hydroxyphenyl)ethynyl)phenyl, 4-hydroxymethylphenyl, 4-(2-hydroxyethyl)phenyl, 4-(3-hydroxypropyl)phenyl, 4-(2-(4-hydroxymethylphenyl)ethynyl)phenyl; 4-mercaptophenyl, mercaptomethyl, 2-mercaptoethyl, 3-mercaptopropyl, 2-(4-mercaptophenyl)ethynyl, 4-(2-(4-mercaptophenyl) ethynyl)phenyl, 4-mercaptomethylphenyl, 4-(2-mercaptoethyl)phenyl, 4-(3-mercaptopropyl)phenyl, 4-(2-(4-mercaptomethylphenyl)ethynyl)phenyl; 4-selenylphenyl, selenylmethyl, 2-selenylethyl, 3-selenylpropyl, 2-(4-selenylphenyl)ethynyl, 4-selenylmethylphenyl, 4-(2-selenylethyl)phenyl, 4-(3-selenylpropyl)phenyl, 4-selenylmethylphenyl, 4-(2-(4-selenylphenyl)ethynyl)phenyl; 4-tellurylphenyl, tellurylmethyl,2-tellurylethyl,3-tellurylpropyl, 2-(4-tellurylphenyl)ethynyl, 4-(2-(4-tellurylphenyl) ethynyl)phenyl, 4-tellurylmethylphenyl, 4-(2-tellurylethyl) phenyl, 4-(3-tellurylpropyl)phenyl, 4-(2-(4-tellurylmethylphenyl)ethynyl)phenyl;

4-(dihydroxyphosphoryl)phenyl, (dihydroxyphosphoryl) methyl,2-(dihydroxyphosphoryl) ethyl, 3-(dihydroxyphosphoryl)propyl, 2-[4-(dihydroxyphosphoryl)phenyl]ethynyl, 4-[2-[4-(dihydroxyphosphoryl)phenyl]ethynyl]phenyl, 4-[(dihydroxyphosphoryl)methyl]phenyl, 4-[2-(dihydroxyphosphoryl)ethyl]phenyl, 4-[2-[4-(dihydroxyphosphoryl) methylphenyl]ethynyl]phenyl; 4-(hydroxy(mercapto)phosphoryl)phenyl, (hydroxy(mercapto)phosphoryl)methyl, 2-(hydroxy(mercapto)phosphoryl)ethyl, 3-(hydroxy(mercapto)phosphoryl)propyl, 2-[4-(hydroxy(mercapto)phosphoryl)phenyl]ethynyl, 4-[2-[4-(hydroxy(mercapto)phosphoryl)phenyl]ethynyl]phenyl, 4-[(hydroxy(mercapto) phosphoryl)methyl]phenyl, 4-[2-(hydroxy(mercapto)

phosphoryl)ethyl]phenyl, 4-[2-[4-(hydroxy(mercapto) phosphoryl)methylphenyl]ethynyl]phenyl;

4-cyanophenyl, cyanomethyl, 2-cyanoethyl, 3-cyanopropyl, 2-(4-cyanophenyl)ethynyl, 4-[2-(4-cyanophenyl)ethynyl]phenyl, 4-(cyanomethyl)phenyl, 4-(2-cyanoethyl)phenyl, 4-[2-[4-(cyanomethyl)phenyl]ethynyl]phenyl;

4-cyanobiphenyl; 4-aminophenyl, aminomethyl, 2-aminoethyl, 3-aminopropyl, 2-(4-aminophenyl)ethynyl, 4-[2-(4-aminophenyl)ethynyl]phenyl, 4-aminobiphenyl;

4-formylphenyl, 4-bromophenyl, 4-iodophenyl, 4-vinylphenyl, 4-ethynylphenyl, 4-allylphenyl, 4-[2-(trimethylsilyl)ethynyl]phenyl, 4-[2-(triisopropylsilyl)ethynyl]phenyl, 4-(4,4,5,5-tetramethyl-1,3,2-dioxaborolan-2-yl)phenyl;

formyl, bromo, iodo, bromomethyl, chloromethyl, ethynyl, vinyl, allyl; 4-(ethynyl)biphen-4'-yl, 4-[2-(triisopropylsilyl)ethynyl]biphen-4'-yl, 3,5-diethynylphenyl;

4-(bromomethyl)phenyl, and 2-bromoethyl.

In addition to the monodentate linker-surface attachment groups described above, multidentate linkers can be employed [Nikitin, K. *Chem. Commun.* 2003, 282-283; Hu, J.; Mattern, D. L. *J. Org. Chem.* 2000, 65, 2277-2281; Yao, Y.; Tour, J. M. *J. Org. Chem.* 1999, 64, 1968-1971; Fox, M. A. et al. *Langmuir*, 1998, 14, 816-820; Galoppini, E.; Guo, W. *J. Am. Chem. Soc.* 2001, 123, 4342-4343; Deng, X. et al. *J. Org. Chem.* 2002, 67, 5279-5283; Hector Jr., L. G. et al. *Surface Science*, 2001, 494, 1-20; Whitesell, J. K.; Chang, H. K. *Science*, 1993, 261, 73-76; Galoppini, E. et al. *J. Am. Chem. Soc.* 2002, 67, 7801-7811; Siiman, O. et al. *Bioconjugate Chem.* 2000, 11, 549-556]. Tripodal linkers bearing thiol, carboxylic acid, alcohol, or phosphonic acid units are particularly attractive for firmly anchoring a molecular device on a planar surface. Specific examples of such linkers are built around the triphenylmethane or tetraphenylmethane unit, including the following:

1,1,1-tris[4-(S-acetylthiomethyl)phenyl]methyl,
4-{1,1,1-tris[4-(S-acetylthiomethyl)phenyl]methyl}phenyl,
1,1,1-tris[4-(dihydroxyphosphoryl)phenyl]methyl,
4-{1,1,1-tris[4-(dihydroxyphosphoryl)phenyl]methyl}phenyl,
1,1,1-tris[4-dihydroxyphosphorylmethyl)phenyl]methyl, and
4-{1,1,1-tris[4-(dihydroxyphosphorylmethyl)phenyl]methyl}phenyl;

All as described in Balakumar, Muthukumaran and Lindsey, U.S. patent application Ser. No. 10/867,512 (filed Jun. 14, 2004). See also Lindsey, Loewe, Muthukumaran, and Ambroise, US Patent Application Publication No. 20050096465 (Published May 5, 2005), particularly paragraph 51 thereof. Additional examples of multidentate linkers include but are not limited to:

Alkene surface attachment groups (2, 3, 4 carbons) such as:
3-vinylpenta-1,4-dien-3-yl,
4-(3-vinylpenta-1,4-dien-3-yl)phenyl,
4-(3-vinylpenta-1,4-dien-3-yl)biphen-4'-yl,
4-allylhepta-1,6-dien-4-yl,
4-(4-allylhepta-1,6-dien-4-yl)phenyl,
4-(4-allylhepta-1,6-dien-4-yl)biphen-4'-yl,
5-(1-buten-4-yl)nona-1,8-dien-5-yl,
4-[5-(1-buten-4-yl)nona-1,8-dien-5-yl]phenyl,
4-[5-(1-buten-4-yl)nona-1,8-dien-5-yl]biphen-4'-yl, etc.

Alkyne surface attachment groups (2, 3, 4 carbons) such as:
3-ethynylpenta-1,4-diyn-3-yl,
4-(3-ethynylpenta-1,4-diyn-3-yl)phenyl,
4-(3-ethynylpenta-1,4-diyn-3-yl)biphen-4'-yl,
4-propargylhepta-1,6-diyn-4-yl,
4-(4-propargylhepta-1,6-diyn-4-yl)phenyl,
4-(4-propargylhepta-1,6-diyn-4-yl)biphen-4'-yl,
5-(1-butyn-4-yl)nona-1,8-diyn-5-yl,
4-[5-(1-butyn-4-yl)nona-1,8-diyn-5-yl]phenyl,
4-[5-(1-butyn-4-yl)nona-1,8-diyn-5-yl]biphen-4'-yl, Alcohol surface attachment groups (1, 2, 3 carbons), such as:
2-(hydroxymethyl)-1,3-dihydroxyprop-2-yl,
4-[2-(hydroxymethyl)-1,3-dihydroxyprop-2-yl]phenyl,
4-[2-(hydroxymethyl)-1,3-dihydroxyprop-2-yl]biphen-4'-yl,
3-(2-hydroxyethyl)-1,5-dihydroxypent-3-yl,
4-[3-(2-hydroxyethyl)-1,5-dihydroxypent-3-yl]phenyl,
4-[3-(2-hydroxyethyl)-1,5-dihydroxypent-3-yl]biphen-4'-yl,
4-(3-hydroxypropyl)-1,7-dihydroxyhept-4-yl,
4-[4-(3-hydroxypropyl)-1,7-dihydroxyhept-4-yl]phenyl,
4-[4-(3-hydroxypropyl)-1,7-dihydroxyhept-4-yl]biphen-4'-yl, etc., Thiol surface attachment groups (1, 2, 3 carbons) such as:
2-(mercaptomethyl)-1,3-dimercaptoprop-2-yl,
4-[2-(mercaptomethyl)-1,3-dimercaptoprop-2-yl]phenyl,
4-[2-(mercaptomethyl)-1,3-dimercaptoprop-2-yl]biphen-4'-yl,
3-(2-mercaptoethyl)-1,5-dimercaptopent-3-yl
4-[3-(2-mercaptoethyl)-1,5-dimercaptopent-3-yl]phenyl,
4-[3-(2-mercaptoethyl)-1,5-dimercaptopent-3-yl]biphen-4'-yl,
4-(3-mercaptopropyl)-1,7-dimercaptohept-4-yl,
4-[4-(3-mercaptopropyl)-1,7-dimercaptohept-4-yl]phenyl,
4-[4-(3-mercaptopropyl)-1,7-dimercaptohept-4-yl]biphen-4'-yl etc., Selenyl surface attachment groups (1, 2, 3 carbons), such as:
2-(selenylmethyl)-1,3-diselenylprop-2-yl,
4-[2-(selenylmethyl)-1,3-diselenylprop-2-yl]phenyl,
4-[2-(mercaptomethyl)-1,3-dimercaptoprop-2-yl]biphen-4'-yl,
3-(2-selenylethyl)-1,5-diselenylpent-3-yl,
4-[3-(2-selenylethyl)-1,5-diselenylpent-3-yl]phenyl,
4-[3-(2-selenylethyl)-1,5-diselenylpent-3-yl]biphen-4'-yl,
4-(3-selenylpropyl)-1,7-diselenylhept-4-yl,
4-[4-(3-selenylpropyl)-1,7-diselenylhept-4-yl]phenyl,
4-[4-(3-selenylpropyl)-1,7-diselenylhept-4-yl]biphen-4'-yl, etc.

Phosphono surface attachment groups (1, 2, 3 carbons), such as:
2-(phosphonomethyl)-1,3-diphosphonoprop-2-yl,
4-[2-(phosphonomethyl)-1,3-diphosphonoprop-2-yl]phenyl,
4-[2-(phosphonomethyl)-1,3-diphosphonoprop-2-yl]biphen-4'-yl,
3-(2-phosphonoethyl)-1,5-diphosphonopent-3-yl,
4-[3-(2-phosphonoethyl)-1,5-diphosphonopent-3-yl]phenyl,
4-[3-(2-phosphonoethyl)-1,5-diphosphonopent-3-yl]biphen-4'-yl,
4-(3-phosphonopropyl)-1,7-diphosphonohept-4-yl,
4-[4-(3-phosphonopropyl)-1,7-diphosphonohept-4-yl]phenyl,
4-[4-(3-phosphonopropyl)-1,7-diphosphonohept-4-yl]biphen-4'-yl, etc., and Carboxylic acid surface attachment groups (1, 2, 3 carbons), such as:
2-(carboxymethyl)-1,3-dicarboxyprop-2-yl,
4-[2-(carboxymethyl)-1,3-dicarboxyprop-2-yl]phenyl,
4-[2-(carboxymethyl)-1,3-dicarboxyprop-2-yl]biphen-4'-yl,
3-(2-carboxyethyl)-1,5-dicarboxypent-3-yl,
4-[3-(2-carboxyethyl)-1,5-dicarboxypent-3-yl]phenyl,
4-[3-(2-carboxyethyl)-1,5-dicarboxypent-3-yl]biphen-4'-yl,
4-(3-carboxypropyl)-1,7-dicarboxyhept-4-yl,
4-[4-(3-carboxypropyl)-1,7-dicarboxyhept-4-yl]phenyl,
4-[4-(3-carboxypropyl)-1,7-dicarboxyhept-4-yl]biphen-4'-yl, etc.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

Active compounds of the invention can be provided as pharmaceutically acceptable salts. Such salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-yl-methyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

Active compounds of the invention include prodrugs of the compounds described herein. As noted above, a "prodrug" is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) Medicinal Chemistry A Biochemical Approach, Oxford University Press, New York, pages 388-392).

Utility.

The methods and intermediates described herein are useful for the synthesis of compounds of Formula I as described herein. Such compounds are useful per se or in further modified form (e.g., as a salt, metalated compound, conjugate or prodrug) for diagnostic and therapeutic purposes in like manner as other compounds described for photodynamic therapy, such as described in US Patent Application Publication No. 2004/0044197 to Pandey et al. and as set forth in further detail below.

Stability.

An advantage of the compounds of the present invention is their stability and absorption characteristics. Thus, the present invention provides a "neat" composition consisting of an active compound of the invention (e.g., compounds of Formula I, or the pharmaceutically acceptable salts, prodrugs, or conjugates thereof (e.g, with a targeting agent such as a protein, peptide or antibody)), wherein the composition has or is characterized by a peak Molar absorption coefficient in solution of at least 10,000, up to 300,000 $M^{-1}$ $cm^{-1}$ or more, at a wavelength between 650 and 850 or 900 nanometers (it being understood that (a) the active compound must be placed into solution to determine its peak Molar absorption coefficient at the indicated wavelength; and (b) the compound may exhibit additional peaks outside of this range, or multiple peaks within this range).

In addition, the present invention provides compositions comprising or consisting essentially of an active compound of the invention (e.g., compounds of Formula I, or the pharmaceutically acceptable salts, prodrugs, or conjugates thereof (e.g, with a targeting agent such as a protein, peptide or antibody)) in a solvent. The amount of solvent is not critical and may comprise from 0.01 or 1 to 99 or 99.99 percent by weight of the composition. The composition has or is characterized by a peak Molar absorption coefficient in solution of at least 10,000, up to 300,000 $M^{-1}$ $cm^{-1}$ or more, at a wavelength between 650 and 850 or 900 nanometers. It will be appreciated that agitation may be required to break agglomerated particles back into solution prior to determining molar absorption, but that some level of agglomeration may actually be desired for practical use of the composition. Suitable solvents depend upon the particular compound and intended use for that compound, but include both organic solvents, aqueous solvents and combinations thereof.

The compositions, be they the bacteriochlorin compounds in "neat" form or the compounds mixed with a solvent, have or exhibit a loss of not more than 10, 15 or 20 percent by weight of the bacteriochlorin compound of the invention (due to degredation thereof) when stored in a sealed vessel (e.g., a flask ampoule or vial), at room temperature in the absence of ambient light for at least 3 or 4 months. Degredation can be determined by spectroscopy, thin-layer chromatography, NMR spectroscopy, and/or mass spectrometry, in accordance with known techniques.

2. Flow Cytometry.

Flow cytometry is known and described in, for example, U.S. Pat. Nos. 5,167; 5,915,925; 6,248,590; 6,589,792; and 6,890,487. In some embodiments the particle being detected, such as a cell, is labelled with a luminescent compound such as a phosphor or fluorophore for detection. Labelling can be carried out by any suitable technique such as coupling the luminescent compound to another compound such as an antibody which in turn specifically binds to the particle or cell, by uptake or internalization of the luminescent compound into the cell or particle, by non-specific adsorption of the luminescent compound to the cell or particle, etc. The bacteriochlorins described herein are useful in flow cytometry as such luminescent compounds, which flow cytometry techniques (including fluorescent activated cell sorting or FACS) may be carried out in accordance with known techniques or variations thereof which will be apparent to those skilled in the art based upon the instant disclosure.

3. Pharmaceutical Formulations.

Formulation of Pharmaceutical Compositions.

The pharmaceutical compositions provided herein contain therapeutically effective amounts of one or more of the compounds provided herein that are useful in the prevention, treatment, or amelioration of one or more of the symptoms of diseases or disorders associated with hyperproliferating tissue or neovascularization, or in which hyperproliferating tissue or neovascularization is implicated, in a pharmaceutically acceptable carrier. Diseases or disorders associated with hyperproliferating tissue or neovascularization include, but are not limited to, cancer, psoriasis, atherosclerosis, heart disease, and age-related macular degeneration. Pharmaceutical carriers suitable for administration of the compounds provided herein include any such carriers known to those skilled in the art to be suitable for the particular mode of administration.

Pharmaceutical compositions preferably exhibit the absorption characteristics and storage or stability characteristics described above.

In addition, the compounds may be formulated as the sole pharmaceutically active ingredient in the composition or may be combined with other active ingredients.

The compositions contain one or more compounds provided herein. The compounds are, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the compounds described above are formulated into pharmaceutical compositions using techniques and procedures well known in the art (see, e.g., Ansel, Introduction to Pharmaceutical Dosage Forms, Fourth Edition 1985, 126).

In the compositions, effective concentrations of one or more compounds or pharmaceutically acceptable derivatives thereof is (are) mixed with a suitable pharmaceutical carrier. The compounds may be derivatized as the corresponding salts, esters, enol ethers or esters, acetals, ketals, orthoesters, hemiacetals, hemiketals, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with hyperproliferating tissue or neovascularization or in which hyperproliferating tissue or neovascularization is implicated.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

The active compound is included in the pharmaceutically acceptable carrier in an amount sufficient to exert a therapeutically useful effect in the absence of undesirable side effects on the patient treated. The therapeutically effective concentration may be determined empirically by testing the compounds in in vitro and in vivo systems described herein and in U.S. Pat. No. 5,952,366 to Pandey et al. (1999) and then extrapolated therefrom for dosages for humans.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with hyperproliferating tissue or neovascularization or in which hyperproliferating tissue or neovascularization is implicated, as described herein.

In one embodiment, a therapeutically effective dosage should produce a serum concentration of active ingredient of from about 0.1 ng/ml to about 50-100 ug/ml. In one embodiment, a therapeutically effective dosage is from 0.001, 0.01 or 0.1 to 10, 100 or 1000 mg of active compound per kilogram of body weight per day. Pharmaceutical dosage unit forms are prepared to provide from about 0.01 mg, 0.1 mg or 1 mg to about 500 mg, 1000 mg or 2000 mg, and in one embodiment from about 10 mg to about 500 mg of the active ingredient or a combination of essential ingredients per dosage unit form.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975.

Dosage forms or compositions containing active ingredient in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

Compositions for Oral Administration.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

Solid Compositions for Oral Administration.

In certain embodiments, the formulations are solid dosage forms, in one embodiment, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether.

Emetic-coatings include fatty acids, fats, waxes, shellac, ammoniated shellac and cellulose acetate phthalates. Film coatings include hydroxyethylcellulose, gellan gum, sodium carboxymethylcellulose, polyethylene glycol 4000 and cellulose acetate phthalate.

The compound, or pharmaceutically acceptable derivative thereof, could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient. When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid Compositions for Oral Administration.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wefting agents. Pharmaceutically acceptable substances used in effervescent granules, to be reconstituted into a liquid oral dosage form, include organic acids and a source of carbon dioxide. Coloring and flavoring agents are used in all of the above dosage forms. Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, xanthan gum, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation. For a solid dosage form, the solution or suspension, in for example propylene carbonate, vegetable oils, or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

3. Injectables, Solutions and Emulsions.

Parenteral administration, in some embodiments characterized by injection, either subcutaneously, intramuscularly, or intravenously, is also contemplated herein. Injectables can be prepared in conventional forms, either as liquid solutions or suspensions, solid forms suitable for solution or suspension in liquid prior to injection, or as emulsions. The injectables, solutions, and emulsions also contain one or more excipients. Suitable excipients include, for example, water, saline, dextrose, glycerol, and ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate, and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, and Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, xanthan gum, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Lyophilized Powders.

Lyophilized powders, which can be reconstituted for administration as solutions, emulsions and other mixtures, can also be used to carry out the present invention. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical Administration.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126; 4,414,209; and 4,364,923, which describe aerosols for delivery of a steroid useful for treatment of inflammatory diseases, particularly asthma). These formulations for administration to the respiratory tract can be in the form of an aerosol or solution for a nebulizer, or as a microtine powder for insufflation, alone or in combination with an inert carrier such as lactose. In such a case, the particles of the formulation will, in one embodiment, have diameters of less than 50 microns, in one embodiment less than 10 microns.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered. These solutions, particularly those intended for ophthalmic use, may be formulated as 0.01%-10% isotonic solutions, pH about 5-7, with appropriate salts.

Compositions for other Routes of Administration.

Other routes of administration, such as transdermal patches, including iontophoretic and electrophoretic devices, and rectal administration, are also contemplated herein.

Transdermal patches, including iotophoretic and electrophoretic devices, are well known to those of skill in the art. For example, such patches are disclosed in U.S. Pat. Nos. 6,267,983; 6,261,595; 6,256,533; 6,167,301; 6,024,975; 6,010715; 5,985,317; 5,983,134; 5,948,433 and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration are manufactured using the same pharmaceutically acceptable substance and by the same methods as for formulations for oral administration.

Targeted Formulations.

The compounds provided herein, or pharmaceutically acceptable derivatives thereof, may also be formulated to be targeted to a particular tissue, receptor, infecting agent or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542 and 5,709,874.

Liposomes.

In one embodiment, liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Ligands.

In another embodiment, the disclosed compounds may be targeted to specific target tissues or target compositions using ligands specific for the target tissue or target composition, for example, using ligands or ligand-receptor pairs such as antibodies and antigens. Antibodies against tumor antigens and against pathogens are known. For example, antibodies and antibody fragments which specifically bind markers produced by or associated with tumors or infectious lesions, including viral, bacterial, fungal and parasitic infections, and antigens and products associated with such microorganisms have been disclosed, inter alia, in Hansen et al., U.S. Pat. No. 3,927,193 and Goldenberg, U.S. Pat. Nos. 4,331,647; 4,348,376; 4,361,544; 4,468,457; 4,444,744; 4,818,709 and 4,624,846. Antibodies against an antigen, e.g., a gastrointestinal, lung, breast, prostate, ovarian, testicular, brain or lymphatic tumor, a sarcoma or a melanoma, can be used.

A wide variety of monoclonal antibodies against infectious disease agents have been developed, and are summarized in a review by Polin, in Eur. J. Clin. Microbiol., 3(5): 387-398 (1984), showing ready availability. These include monoclonal antibodies (MAbs) against pathogens and their antigens such as the following: Anti-bacterial Mabs such as those against *Streptococcus agalactiae, Legionella pneumophilia, Streptococcus pyogenes, Esherichia coli, Neisseria gonorrhosae, Neisseria meningitidis*, Pneumococcus, *Hemophilis influenzae* B, *Treponema pallidum*, Lyme disease, spirochetes, *Pseudomonas aeruginosa, Mycobacterium leprae, Brucella abortus, Mycobacterium tuberculosis*, Tetanus toxin, Anti-protozoan Mabs such as those against *Plasmodium falciparum, Plasmodium vivax, Toxoplasma gondii, Trypanosoma rangeli, Trypanosoma cruzi, Trypanosoma rhodesiensei, Trypanosoma brucei, Schistosoma mansoni, Schistosoma japanicum, Mesocestoides corti, Emeria tenella, Onchocerca volvulus, Leishmania tropica, Trichinella spiralis, Theileria parva, Taenia hydatigena, Taenia ovis*, and *Taenia saginata*, anti-viral MAbs such as those against HIV-1, -2, and -3, Hepatitis A, B, C, D, Rabies virus, Influenza virus, Cytomegalovirus, Herpes simplex I and II, Human serum parvo-like virus, Respiratory syncytial virus, Varicella-Zoster virus, Hepatitis B virus, Measles virus, Adenovirus, Human T-cell leukemia viruses, Epstein-Barr virus, Mumps virus, Sindbis virus, Mouse mammary tumor virus, Feline leukemia virus, Lymphocytic choriomeningitis virus, Wart virus, Blue tongue virus, Sendai virus, Reo virus, Polio virus, Dengue virus, Rubella virus, Murine leukemia virus; and antimycoplasmal MAbs such as those against *Acholeplasma laidlawii, Mycoplasma arthritidis, M. hyorhinis, M. orale, M. arginini, M. pneumonia*; etc.

Suitable MAbs have been developed against most of the microorganisms (bacteria, viruses, protozoa, other parasites) responsible for the majority of infections in humans, and many have been used previously for in vitro diagnostic purposes. These antibodies, and newer MAbs that can be generated by conventional methods, are appropriate for use as target agents with the compounds provided herein.

MAbs against malaria parasites can be directed against the sporozoite, merozoite, schizont and gametocyte stages. Monoclonal antibodies have been generated against sporozoites (circumsporozoite antigen), and have been shown to neutralize sporozoites in vitro and in rodents (N. Yoshida et al., Science 207: 71-73 (1980)). Monoclonal antibodies to *T. gondii*, the protozoan parasite involved in toxoplasmosis have been developed (Kasper et al., J. Immunol. 129: 1694-1699 (1982). MAbs have been developed against schistosomular surface antigens and have been found to act against schistosomulae in vivo or in vitro (Simpson et al., Parasitology 83: 163-177 (1981); Smith et al., Parasitology 84: 83-91 (1982); Gryzch et al., J. Immunol. 129: 2739-2743 (1982); Zodda et al., J. Immunol. 129: 2326-2328 (1982); Dissous et al., J. Immunol. 129: 2232-2234 (1982).

It should be noted that mixtures of antibodies and immunoglobulin classes can be used, as can hybrid antibodies. Multispecific, including bispecific and hybrid, antibodies and antibody fragments are especially preferred in the methods of the present invention for detecting and treating target tissue and are comprised of at least two different substantially monospecific antibodies or antibody fragments, wherein at least two of said antibodies or antibody fragments specifically bind to at least two different antigens produced or associated with the targeted lesion or at least two different epitopes or molecules of a marker substance produced or associated with the target tissue. Multispecific antibodies and antibody fragments with dual specificities can be prepared analogously to the anti-tumor marker hybrids disclosed in U.S. Pat. No. 4,361,544. Other techniques for preparing hybrid antibodies are disclosed in, e.g., U.S. Pat. Nos. 4,474,893 and 4,479,895, and in Milstein et al., Immunol. Today 5: 299 (1984).

Antibody fragments useful in the present invention include F(ab')$_2$, F(ab)$_2$, Fab', Fab, Fv and the like including hybrid fragments. Preferred fragments are Fab', F(ab')$_2$, Fab, and F(ab)$_2$. Also useful are any subfragments retaining the hypervariable, antigen-binding region of an immunoglobulin and having a size similar to or smaller than a Fab' fragment. This will include genetically engineered and/or recombinant proteins, whether single-chain or multiple-chain, which incorporate an antigen-binding site and otherwise function in vivo as targeting vehicles in substantially the same way as natural immunoglobulin fragments. Such single-chain binding molecules are disclosed in U.S. Pat. No. 4,946,778, which is hereby incorporated by reference. Fab' antibody fragments may be conveniently made by reductive cleavage of F(ab')$_2$ fragments, which themselves may be made by pepsin digestion of intact immunoglobulin. Fab antibody fragments may be made by papain digestion of intact immunoglobulin, under reducing conditions, or by cleavage of F(ab)$_2$ fragments which result from careful papain digestion of whole immunoglobulin.

A ligand or one member of a ligand-receptor binding pair can be conjugated to the compounds provided herein for targeting the compounds to specific target tissues or target compositions. Examples of ligand-receptor binding pairs are set out in U.S. Pat. Nos. 4,374,925 and 3,817,837, the teachings of which are incorporated herein by reference.

Conjugation to Ligands.

Many compounds that can serve as targets for ligand-receptor binding pairs, and more specifically, antibodies, have been identified, and the techniques to construct conjugates of such ligands with photosensitizers are well known to those of ordinary skill in this art. For example, Rakestraw et al. teaches conjugating Sn(IV) chlorin e via covalent bonds to monoclonal antibodies using a modified dextran carrier (Rakestraw, S. L., Tompkins, R. D., and Yarmush, M. L., Proc. Nad. Acad. Sci. USA 87: 4217-4221 (1990). The compounds disclosed herein can also be conjugated to a ligand, such as an antibody, by using a coupling agent. Any bond which is capable of linking the components such that they are stable under physiological conditions for the time needed for administration and treatment is suitable, but covalent linkages are preferred. The link between two components may be direct, e.g., where a photosensitizer is linked directly to a targeting agent, or indirect, e.g., where a photosensitizer is linked to an intermediate and that intermediate being linked to the targeting agent.

A coupling agent should function under conditions of temperature, pH, salt, solvent system, and other reactants that substantially retain the chemical stability of the photosensitizer, the backbone (if present), and the targeting agent. Coupling agents should link component moieties stably, but such that there is only minimal or no denaturation or deactivation of the photosensitizer or the targeting agent. Many coupling agents react with an amine and a carboxylate, to form an amide, or an alcohol and a carboxylate to form an ester. Coupling agents are known in the art (see, e.g., M. Bodansky, "Principles of Peptide Synthesis", 2nd ed., and T. Greene and P. Wuts, "Protective Groups in Organic Synthesis," 2nd Ed, 1991, John Wiley, NY).

The conjugates of the compounds provided herein with ligands such as antibodies can be prepared by coupling the compound to targeting moieties by cleaving the ester on the "d" ring and coupling the compound via peptide linkages to the antibody through an N terminus, or by other methods known in the art. A variety of coupling agents, including cross-linking agents, can be used for covalent conjugation. Examples of cross-linking agents include N,N'-dicyclohexylcarbodiimide (DCC), N-succinimidyl-S-acetyl-thioacetate (SATA), N-succinimidyl-3-(2-pyridyidi-thio)propionate (SPDP), ortho-phenylene-dimaleimide (o-PDM), and sulfo-succinimidyl 4-(N-maleimido-methyl)-cyclohexane-1-carboxylate (sulfo-SMCC). See, e.g., Karpovsky et al. J. Exp. Med. 160:1686 (1984); and Liu, M A et al., Proc. Natl. Acad. Sci. USA 82: 8648 (1985). Other methods include those described by Brennan et al. Science 229: 81-83 (1985) and Glennie et al., J. Immunol. 139: 2367-2375 (1987). A large number of coupling agents for peptides and proteins, along with buffers, solvents, and methods of use, are described in the Pierce Chemical Co. catalog, pages 0-90 to 0-110 (1995, Pierce Chemical Co., 3747 N. Meridian Rd., Rockford Ill., 61105, U.S.A.), which catalog is hereby incorporated by reference.

For example, DCC is a useful coupling agent that can be used to promote coupling of the alcohol NHS to chlorin e6 in DMSO forming an activated ester which can be cross-linked to polylysine. DCC is a carboxy-reactive cross-linker commonly used as a coupling agent in peptide synthesis, and has a molecular weight of 206.32. Another useful cross-linking agent is SPDP, a heterobifunctional cross-linker for use with primary amines and sulfhydryl groups. SPDP has a molecular weight of 312.4, a spacer arm length of 6.8 angstroms, is reactive to NETS-esters and pyridyldithio groups, and produces cleavable cross-linking such that, upon further reaction, the agent is eliminated so the photosensitizer can be linked directly to a backbone or targeting agent. Other useful conjugating agents are SATA for introduction of blocked SH groups for two-step cross-linking, which is deblocked with hydroxylamine-HCl, and sulfo-SMCC, reactive towards amines and sulfhydryls. Other cross-linking and coupling agents are also available from Pierce Chemical Co. Additional compounds and processes, particularly those involving a Schiff base as an intermediate, for conjugation of proteins to other proteins or to other compositions, for example to reporter groups or to chelators for metal ion labeling of a protein, are disclosed in European Patent No. EP 0 243 929 A2 (published Nov. 4, 1987).

Photosensitizers which contain carboxyl groups can be joined to lysine ε-amino groups in the target polypeptides either by preformed reactive esters (such as N-hydroxy succinimide ester) or esters conjugated in situ by a carbodiimide-mediated reaction. The same applies to photosensitizers which contain sulfonic acid groups, which can be transformed to sulfonyl chlorides which react with amino groups. Photosensitizers which have carboxyl groups can be joined to amino groups on the polypeptide by an in situ carbodiimide method. Photosensitizers can also be attached to hydroxyl groups, of serine or threonine residues or to sulfhydryl groups of cysteine residues.

Methods of joining components of a conjugate, e.g., coupling polyamino acid chains bearing photosensitizers to antibacterial polypeptides, can use heterobifunctional cross linking reagents. These agents bind a functional group in one chain and to a different functional group in the second chain. These functional groups typically are amino, carboxyl, sulfhydryl, and aldehyde. There are many permutations of appropriate moieties which will react with these groups and with differently formulated structures, to conjugate them together. See the Pierce Catalog, and Merrifield, R. B. et al., Ciba Found Symp. 186: 5-20 (1994).

The compounds or pharmaceutically acceptable derivatives thereof may be packaged as articles of manufacture containing packaging material, a compound or pharmaceutically acceptable derivative thereof provided herein, which is effective for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization activity, is implicated, within the packaging material, and a label that indicates that the compound or composition, or pharmaceutically acceptable derivative thereof, is used for modulating the activity of hyperproliferating tissue or neovascularization, or for treatment, prevention or amelioration of one or more symptoms of hyperproliferating tissue or neovascularization mediated diseases or disorders, or diseases or disorders in which hyperproliferating tissue or neovascularization is implicated.

The articles of manufacture provided herein contain packaging materials. Packaging materials for use in packaging pharmaceutical products are well known to those of skill in the art. See, e.g., U.S. Pat. Nos. 5,323,907; 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which hyperproliferating tissue or neovascularization is implicated as a mediator or contributor to the symptoms or cause.

4. Methods of Use.

A. Methods of PDT, Diagnostic and Therapeutic Applications.

Briefly, the photosensitizing compound is generally administered to the subject before the target tissue, target composition or subject is subjected to illumination. The photosensitizing compound is administered as described elsewhere herein.

The dose of photosensitizing compound can be determined clinically. Depending on the photosensitizing compound used, an equivalent optimal therapeutic level will have to be established. A certain length of time is allowed to pass for the circulating or locally delivered photosensitizer to be taken up by the target tissue. The unbound photosensitizer is cleared from the circulation during this waiting period, or additional time can optionally be provided for clearing of the unbound compound from non-target tissue. The waiting period will be determined clinically and may vary from compound to compound.

At the conclusion of this waiting period, a laser light source or a non-laser light source (including but not limited to artificial light sources such as fluorescent or incandescent light, or natural light sources such as ambient sunlight) is used to activate the bound drug. The area of illumination is determined by the location and dimension of the pathologic region to be detected, diagnosed or treated. The duration of illumination period will depend on whether detection or treatment is being performed, and can be determined empirically. A total or cumulative period of time anywhere from between about 4 minutes and 72 hours can be used. In one embodiment, the illumination period is between about 60 minutes and 148 hours. In another embodiment, the illumination period is between about 2 hours and 24 hours.

Preferably, the total fluence or energy of the light used for irradiating, as measured in Joules, is between about 10 Joules and about 25,000 Joules; more preferably, between about 100 Joules and about 20,000 Joules; and most preferably, between about 500 Joules and about 10,000 Joules. Light of a wavelength and fluence sufficient to produce the desired effect is selected, whether for detection by fluorescence or for therapeutic treatment to destroy or impair a target tissue or target composition. Light having a wavelength corresponding at least in part with the characteristic light absorption wavelength of the photosensitizing agent is preferably used for irradiating the target issue.

The intensity or power of the light used is measured in watts, with each Joule equal to one watt-sec. Therefore, the intensity of the light used for irradiating in the present invention may be substantially less than 500 mW/cm$^2$. Since the total fluence or amount of energy of the light in Joules is divided by the duration of total exposure time in seconds, the longer the amount of time the target is exposed to the irradiation, the greater the amount of total energy or fluence may be used without increasing the amount of the intensity of the light used. The present invention employs an amount of total fluence of irradiation that is sufficiently high to activate the photosensitizing agent.

In one embodiment of using compounds disclosed herein for photodynamic therapy, the compounds are injected into the mammal, e.g. human, to be diagnosed or treated. The level of injection is usually between about 0.1 and about 0.5 umol/kg of body weight. In the case of treatment, the area to be treated is exposed to light at the desired wavelength and energy, e.g. from about 10 to 200 J/cm$^2$. In the case of detection, fluorescence is determined upon exposure to light at a wavelength sufficient to cause the compound to fluoresce at a wavelength different than that used to illuminate the compound. The energy used in detection is sufficient to cause fluorescence and is usually significantly lower than is required for treatment.

Any one of the photosensitizing compounds disclosed herein or a pharmaceutically acceptable derivative thereof may be supplied in a kit along with instructions on conducting any of the methods disclosed herein. Instructions may be in any tangible form, such as printed paper, a computer disk that instructs a person how to conduct the method, a video cassette containing instructions on how to conduct the method, or computer memory that receives data from a remote location and illustrates or otherwise provides the instructions to a person (such as over the Internet). A person may be instructed in how to use the kit using any of the instructions above or by receiving instructions in a classroom or in the course of treating a patient using any of the methods disclosed herein, for example.

Additional examples and specific examples of methods of using compounds and compositions of the present invention include but are not limited to the following:

(i) Treatment of opportunistic infections. Compounds, compositions and methods of the invention are useful for PDT of opportunistic infections, particularly of soft tissue. For antimicrobial treatment (via PDT) of infections, particularly wound infections, the infecting organism can include (as non limiting examples) *Staphylococcus aureus, Pseudomonas aeruginosa, Escherichia coli*. In nosocomial infections, *P. aeruginosa* is responsible for 8% of surgical-wound infections and 10% of bloodstream infections. In some embodiments the subjects are immunocompromised subjects, such as those afflicted with AIDS or undergoing treatment with immunosupressive agents.

(ii) Treatment of burns. Infections by *S. aureus* and gram-positive bacteria in general are particularly pronounced in burns (Lambrechts, 2005). The multidrug resistance of *S. aureus* presents significant medical challenges. In this regard, compounds, compositions and methods of the invention are useful for the treatment of opportunistic infections of burns.

(iii) Sepsis. Compounds, compositions and methods of the invention are useful for the PDT treatment of subjects afflicted with opportunistic infections of *Vibrio vulnificus*. *V. vulnificus*, a gram-negative bacterium, causes primary sepsis, wound infections, and gastrointestinal illness in humans.

(iv) Ulcers. Compounds, compositions and methods of the invention are useful for PDT treatment of the bacterium that causes ulcers (*Helicobacter pylori*). In the clinic, treatment can be effected in any suitable manner, such as by insertion of a fiber optic cable (akin to an endoscope but with provisions for delivery of red or near-IR light) into the stomach or afflicted region.

(v) Periodontal disease. Compounds, compositions and methods of the invention are useful in PDT for the treatment of periodontal disease, including gingivitis. Periodontal disease is caused by the overgrowth of bacteria, such as the gram-negative anaerobe *Porphyromonas gingivalis*. As with many PDT treatments, targeting or solubilizing entities in conjunction with the photoactive species are essential for appropriate delivery of the photoactive species to the desired cells. The oral pathogens of interest for targeting include *Porphyromonas gingivalis, Actinobacillus actinomycetemcomitans, Bacteroides forsythus, Campylobacter rectus, Eikenella corrodens, Fusobacterium nucleatum* subsp. *Polymorphum, Actinomyces viscosus*, and the streptococci. For such applications the compounds or compositions of the invention can be topically applied (e.g., as a mouthwash or rinse) and then light administered with an external device, in-the-mouth instrument, or combination thereof.

(vi) Atherosclerosis. Compounds, compositions and methods of the invention are useful in PDT to treat vulnerable atherosclerotic plaque. Without wishing to be bound to any particular theory, invading inflammatory macrophages are believed to secrete metalloproteinases that degrade a thin layer of collagen in the coronary arteries, resulting in thrombosis, which often is lethal (Demidova and Hamblin, 2004). Bacteriochlorins targeted to such inflammatory macrophages are useful for PDT of vulnerable plaque.

(vii) Cosmetic and dermatologic applications. Compounds, compositions and methods of the invention are useful in PDT to treat a wide range of cosmetic dermatological problems, such as hair removal, treatment of psoriasis, or removal of skin discoloration. Ruby lasers are currently used for hair removal; in many laser treatments melanin is the photosensitized chromophore. Such treatments work reasonably well for fair-skinned individuals with dark hair. Compounds, compositions and methods of the invention can be used as near-IR sensitizers for hair removal, which enables targeting a chromophore with a more specific and sharp absorption band.

(viii) Acne. Compounds, compositions and methods of the invention are useful in PDT to treat acne. Acne vulgaris is caused by *Propionibacterium acnes*, which infects the sebaceous gland; some 80% of young people are affected. Here again, the growing resistance of bacteria to antibiotic treatment is leading to an upsurge of acne that is difficult to treat. Current PDT treatments of acne typically rely on the addition of aminolevulinic acid, which in the hair follicle or sebaceous gland is converted to free base porphyrins. Compounds and compositions of the invention can be administered to subjects topically or parenterally (e.g., by subcutaneous injection) depending upon the particular condition.

(ix) Infectious diseases. Compounds, compositions and methods of the invention are useful in PDT to treat infectious diseases. For example, Cutaneous leishmaniasis and subcutaneous leishmaniasis, which occurs extensively in the Mediterranean and Mideast regions, is currently treated with arsenic-containing compounds. PDT has been used to reasonable effect recently, at least in one case, on a human patient. The use of compounds and compositions of the present invention are likewise useful, and potentially offer advantages such as ease of synthesis and better spectral absorption properties.

(x) Tissue sealants. Compounds, compositions and methods of the invention are useful in PDT as tissue sealants in subjects in need thereof. Light-activated tissue sealants are attractive for sealing wounds, bonding tissue, and closing defects in tissue There are many applications where sutures or staples are undesirable, and use of such mechanical methods of sealing often lead to infection and scarring.

(xi) Neoplastic disease. Compounds, compositions and methods of the invention are useful in PDT for treating neoplastic diseases or cancers, including skin cancer, lung cancer, colon cancer, breast cancer, prostate cancer, cervical cancer, ovarian cancer, basal cell carcinoma, leukemia, lymphoma, squamous cell carcinoma, melanoma, plaque-stage cutaneous T-cell lymphoma, and Kaposi sarcoma.

B. Imaging Enhancing Agents.

In addition to PDT, the compositions provided herein can be used as imaging enhancing agents in diagnostic imaging techniques, or for the labeling of target tissues or target compositions for diagnostic radiology. In the modern medical field, there are a variety of treatments including magnetic resonance imaging (MRI) for the diagnosis of diseases. Detection of cancer in its early stages should improve the ability to cure eliminate the cancerous tissue. Early diagnosis of precancerous regions and minute cancer are important subject matters in modern cancer treatments. MRI has emerged as a powerful tool in clinical settings because it is noninvasive and yields an accurate volume rendering of the subject. The image is created by imposing one or more orthogonal magnetic field gradients upon the subject or specimen while exciting nuclear spins with radio frequency pulses as in a typical nuclear magnetic resonance (NMR) experiment. After collection of data with a variety of gradient fields, deconvolusion yields a one, two, or three dimensional image of the specimen/subject. Typically, the image is based on the NMR signal from the protons of water where the signal intensity in a given volume element is a function of the water concentration and relaxation times. Local variation in there parameters provide the vivid contrast observed in MR images.

MRI contrast agents act by increasing the rate of relaxation, thereby increasing the contrast between water molecules in the region where the imaging agent accretes and water molecules elsewhere in the body. However, the effect of the agent is to decrease both $T_1$ and $T_2$, the former resulting in greater contrast while the latter results in lesser contrast. Accordingly, the phenomenon is concentration-dependent, and there is normally an optimum concentration of a paramagnetic species for maximum efficacy. This optimal concentration will vary with the particular agent used, the locus of imaging, the mode of imaging, i.e., spin-echo, saturation-recovery, inversion-recovery and/or various other strongly $T_1$-dependent or $T_2$-dependent imaging techniques, and the composition of the medium in which the agent is dissolved or suspended. These factors, and their relative importance are known in the art. See, e.g., Pykett, Scientific American 246: 78 (1982); Runge et al., Am. J. Radiol. 141: 1209 (1983). When MRI contrast agents are used diagnostically, they are vascularly perfused, enhancing the contrast of blood vessels and reporting on organ lesions and infiltration. However, the labeling of specific tissues for diagnostic radiology remains a difficult challenge for MRI. Efforts to develop cell and tissue-specific MRI image enhancing agents by modifying existing immunological techniques has been the focus of much research in diagnostic radiology. For example, antibodies labeled with paramagnetic ions, generally the gadolinium chelate Gd-DTPA, have been generated and tested for their effects on MRI contrast of tumors and other tissues (U.S. Pat. No. 5,059,415). Unfortunately, the relaxivity of Gd bound to antibodies has been found to be only slightly better than that of unbound Gd-DTPA (Paajanen et al., Magn. Reson. Med 13: 38-43 (1990)).

MRI is generally used to detect $^1H$ nuclei in the living body. However, MRI is capable of detecting NMR spectrums of other nuclear species, including $^{13}C$, $^{15}N$, $^{31}P$, and $^{19}F$. The $^{19}F$ is not abundant in the living body. By incorporating isotopes useful in MRI, such as $^{13}C$, $^{15}N$, $^{31}P$, or $^{19}F$, and particularly $^{19}F$ in the compositions provided herein and administering to a subject, the compounds provided herein would accumulate in target tissue, and subsequent MR imaging would produce NMR data with enhanced signal from the targeted tissue or target compositions due to the presence of the accumulated compound with the MRI recognizable isotope, such as $^{19}F$. Thus, the disclosed compounds can be used as image enhancing agents and provide labeling of specific target tissues or target compositions for diagnostic radiology, including MRI.

C. Detecting Target Tissue or Target Compositions.

In addition to PDT, the compositions provided herein can be used to detect target cells, target tissue, or target compositions in a subject. When the compounds provided herein are to be used for detection of target tissue or target composition, the compounds are introduced into the subject and sufficient time is allowed for the compounds to accumulate in the target tissue or to become associated with the target composition. The area of treatment is then irradiated, generally using light of an energy sufficient to cause fluorescence of the compound, and the energy used is usually significantly lower than is required for photodynamic therapy treatment. Fluorescence is determined upon exposure to light at the desired wavelength, and the amount of fluorescence can be correlated to the presence of the compound, qualitatively or quantitatively, by methods known in the art.

D. Diagnosing an Infecting Agent.

The compositions provided herein can be used to diagnose the presence of an infecting agent, or the identity of an infecting agent in a subject. The compounds provided herein can be conjugated to one or more ligands specific for an infecting agent, such as an antibody or antibody fragment, that selectively associates with the infecting agent, and after allowing sufficient time for the targeted compound to associate with the infecting agent and to clear from non-target tissue, the compound can be visualized, such as by exposing to light of an energy sufficient to cause fluorescence of the compound, or by imaging using diagnostic radiology, including MRI. By way of example, any one of the compounds provided herein can be conjugated to an antibody that is targeted against a suitable *Helicobacter pylori* antigen, and formulated into a pharmaceutical preparation that, when introduced into a subject, releases the conjugated compound to a gastric mucus/epithelial layer where the bacterium is found. After sufficient time for the compound to selectively associate with the target infecting agent, and for any unbound compound to clear from non-target tissue, the subject can be examined to determine whether any *Helicobacter pylori* is present. This can be done by MRI to detect accumulated compound because of the presence of $^{19}F$ substituents, for example, or by irradiating the suspect target area with light of an energy sufficient to cause fluorescence of the compound, such as by using fiberoptics, and detecting any fluorescence of the targeted compound.

5. Solar Cells, Light Harvesting Rods and Light Harvesting Arrays.

Bacteriochlorins of Formula I herein may be used as chromophores (also referred to as photosensitizers or simply sensitizers) in solar cells, including but not limited to high surface area colloidal semiconductor film solar cells (Gratzel cells), as described in, for example, U.S. Pat. Nos. 5,441,827; 6,420,648; 6,933,436; 6,924,427; 6,913,713; 6,900,382; 6,858,158; and 6,706,963.

Bacteriochlorins of Formula I may be used as chromophores in the light harvesting rods described in U.S. Pat. Nos. 6,407,330 and 6,420,648 (incorporated herein by reference). The light harvesting rod may comprise one or more bacteriochlorins of Formula I coupled to one or two adjacent chromophores depending upon the position thereof in the light harvesting rod. Such light harvesting rods may be utilized to produce light harvesting arrays as described in U.S. Pat. No. 6,420,648 and solar cells as described in U.S. Pat. No. 6,407,330.

6. Information Storage Devices.

Bacteriochlorins of the invention are also useful immobilized to a substrate for making charge storage molecules and information storage devices containing the same, either individually or as linked polymers thereof, either optionally including additional compounds to add additional oxidation states. Such charge storage molecules and information storage devices are known and described in, for example, U.S. Pat. No. 6,208,553 to Gryko et al.; U.S. Pat. No. 6,381,169 to Bocian et al.; and U.S. Pat. No. 6,324,091 to Gryko et al.

The bacteriochlorins of the invention may comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the following non-limiting experimental section.

EXPERIMENTAL

Synthesizing and tailoring bacteriochlorins with different substituents and uniting multiple functions in one molecule has been our synthetic objective. Up until the present Northern-Southern strategy was invented, we used an Eastern-Western route[184] to synthesize bacteriochlorins (Scheme 1). A 2-(2-nitroethyl)-1H-pyrrole B synthesized from a pyrrole-2-carbaldehyde A could perform a Michael-addition with C or D followed by a McMurry type of reductive ring closure to give dihydrodipyrrin F or dihydrodipyrrin-acetal H. Dihydrodipyrrin F can also be easily converted to dihydrodipyrrin-acetal H via simple oxidation and protection. Self-condensation of dihydrodipyrrin-acetal H under Lewis acidic conditions affords bacteriochlorin bearing a 5-methoxy substituent (5-MeOBC) or bacteriochlorin with no meso-substituents (HBC). Based on our current methodology, a variety of β-pyrrole substituents can be introduced to provide, and 15-bromination of 5-MeOBC could be carried out to provide a site for Pd coupling reactions, which allows further functionalization of the molecule.[219]

Scheme 1. De novo synthesis of bacteriochlorins

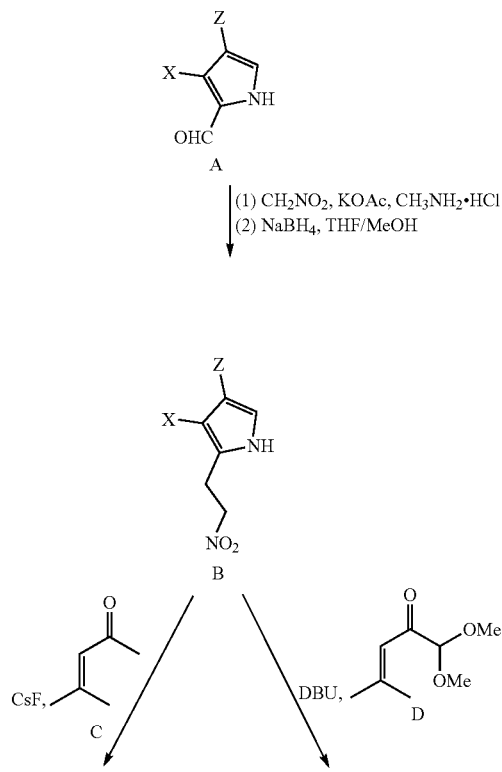

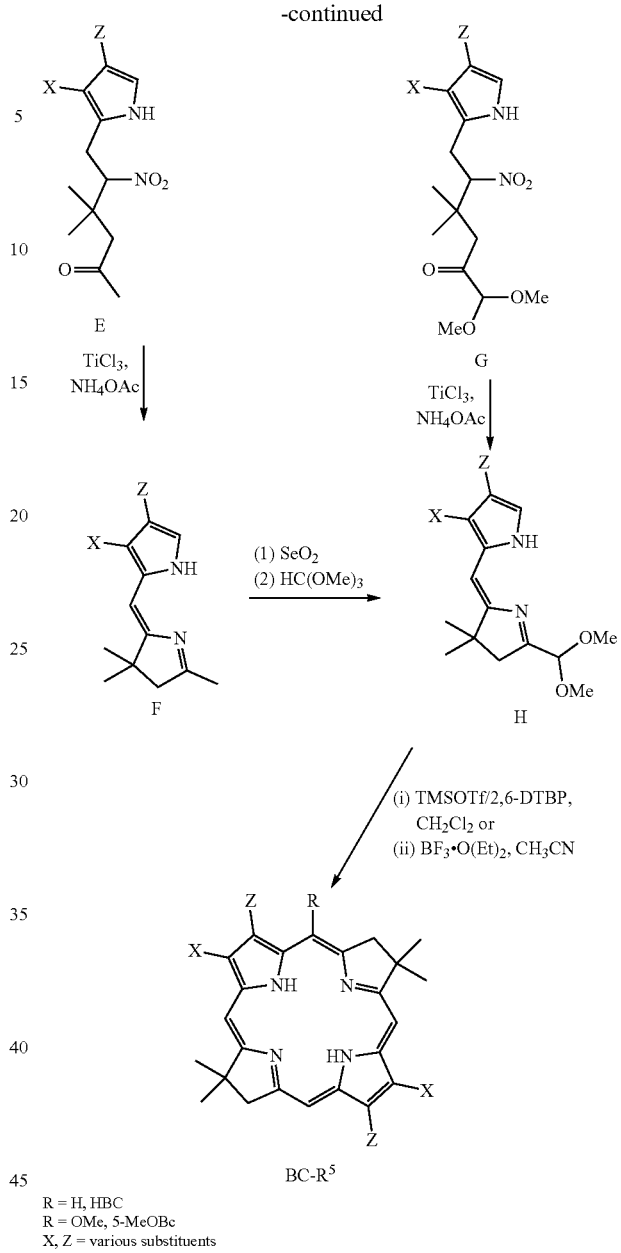

R = H, HBC
R = OMe, 5-MeOBc
X, Z = various substituents

However, as further application is required, more sites need to be functionalized, causing the synthesis to become complicated and challenging. There are two limitations in the current synthesis of bacteriochlorins (Scheme 2): (1) the preparation of meso-disubstituted bacteriochlorins (BC-$R^{5,15}$); and (2) synthesis of swallowtail bacteriochlorins (BC-SWT), where long chain alkyl groups replace methyl groups in the pyrroline rings. A meso-disubstituted bacteriochlorin (BC-$R^{5,15}$) in principle could be made from a 5,15-dibromobacteriochlorin (BC-$R^{5,15-Br}$) via Pd coupling reactions, or a Michael-addition reaction with preinstalled Michael precursors (C-$R^1$ or D-$R^1$). The problem with the former design is the low yield and difficulty in isolation of the meso-dibrominated derivative of HBC. The latter approach relies on access to H-$R^1$ and Michael accepters (C-$R^1$ or D-$R^1$), which have hardly been explored. As we reported before,[304] unexpected isomerization of the Michael acceptor is the major issue.

Scheme 2. Limitations of current bacteriochlorin synthesis.

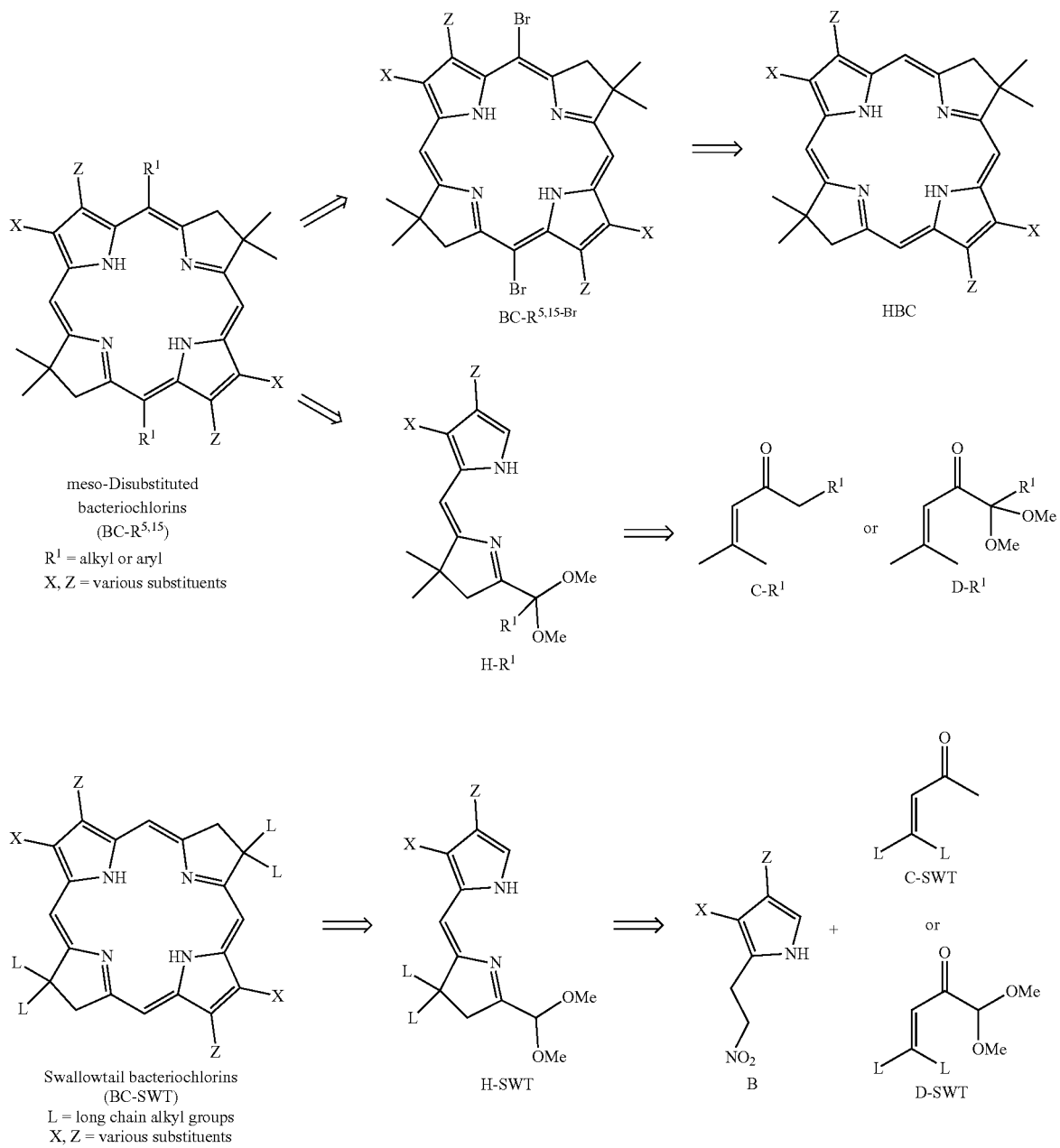

Thus, an exploration of a novel robust route to synthesize bacteriochlorins is required to complement our current methodology. The pattern of substituents that can be introduced to a bacteriochlorin depends in large part on access to the corresponding dihydrodipyrrin. In this regard, we were struck by the apparent complementary features of our route to dihydrodipyrrins (Scheme 1) and a route developed to dihydrodipyrrins by Jacobi and coworkers for use in a synthesis of chlorins.[6] Jacobi's route is shown in Scheme 3. A Pd-coupling reaction of iodopyrrole J2 and pent-4-ynoic acid J1 afforded the enelactone J3. The subsequent Petasis reagent treatment and Paal-Knorr type of ring formation gave the dihydrodipyrrin J5, which was further tailored as a Southern half in chlorin synthesis.

Jacobi and coworkers have successfully demonstrated the preparation of a family of meso-methyl, phenyl, and long chain alkyl-substituted and unsubstituted chlorins, which is a tremendous milestone in dihydrodipyrrin and chlorin chemistry. However, this methodology: (1) has only been used in chlorin chemistry, and no other tetrapyrrole macrocycles have been isolated via this route; (2) substituents other than dimethyl groups as β-pyrrole substituents have not been demonstrated; and (3) no substituents other than dimethyls as β-pyrroline substituents have been demonstrated. Nevertheless, we attempted to adapt Jacobi's approach for our synthesis of meso-disubstituted bacteriochlorins.

Scheme 3. Jacobi's chlorin synthesis

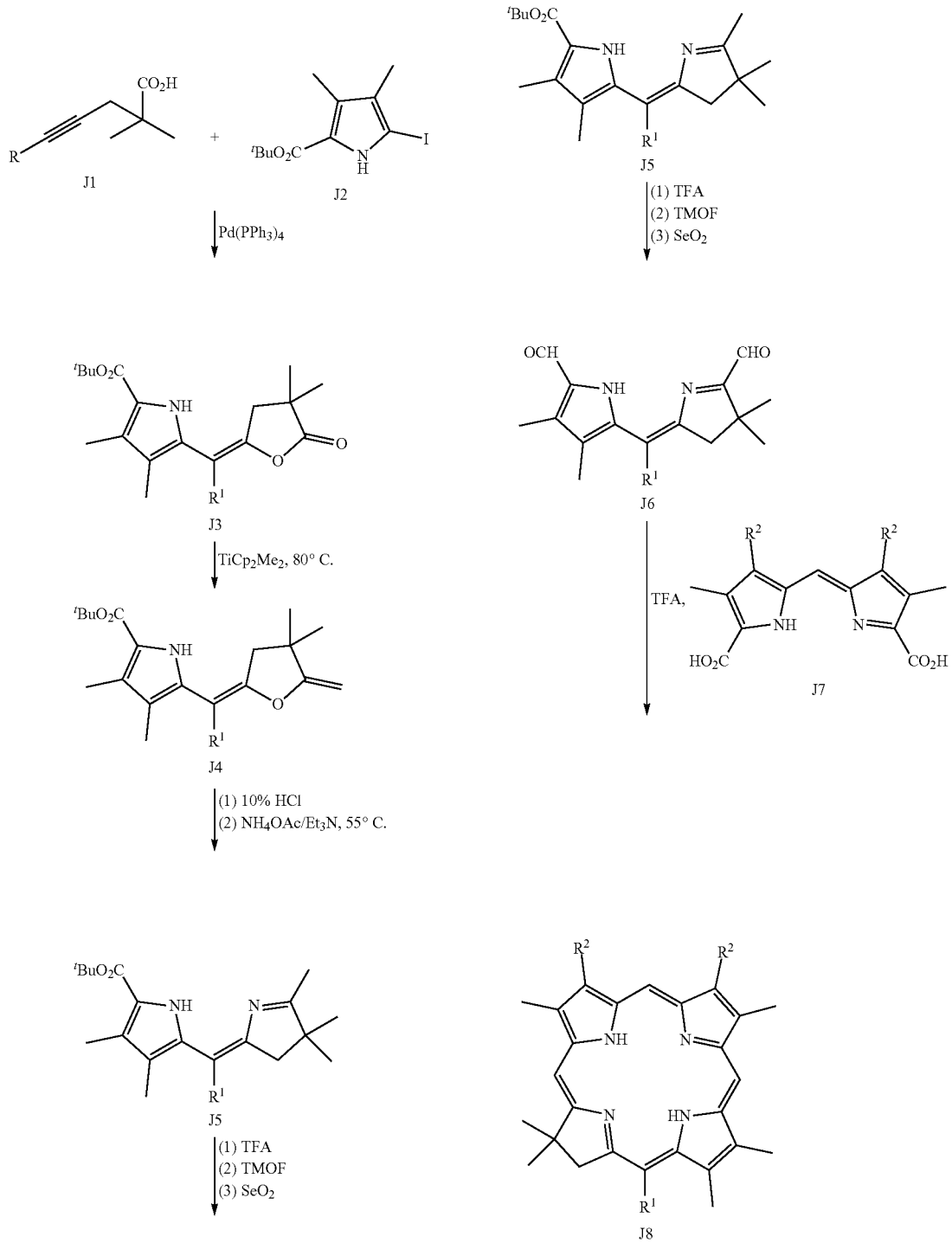

R[1] = Me, Ph or long chain alkyl
R[2] = Me or (CH$_2$)$_n$CO$_2$Me

The distinction between our prior Eastern-Western condensation to give bacteriochlorins and our new Northern-Southern route is shown in Scheme 4. There are at least two major differences between these two routes: (1) instead of a 3,3-dimethyldihydrodipyrrin-acetal H, a 2,2-dimethyldihydrodipyrrin-acetal I (L=Me) is required to perform a Northern-Southern self-condensation; and (2) the targeted bacteriochlorin is expected to have a methoxy group substituted at the 10-position instead of the 5-position (if a methoxy-bacteriochlorin indeed is obtained).

Scheme 4. Eastern-Western route versus Northern-Southern route

Eastern-Western Route

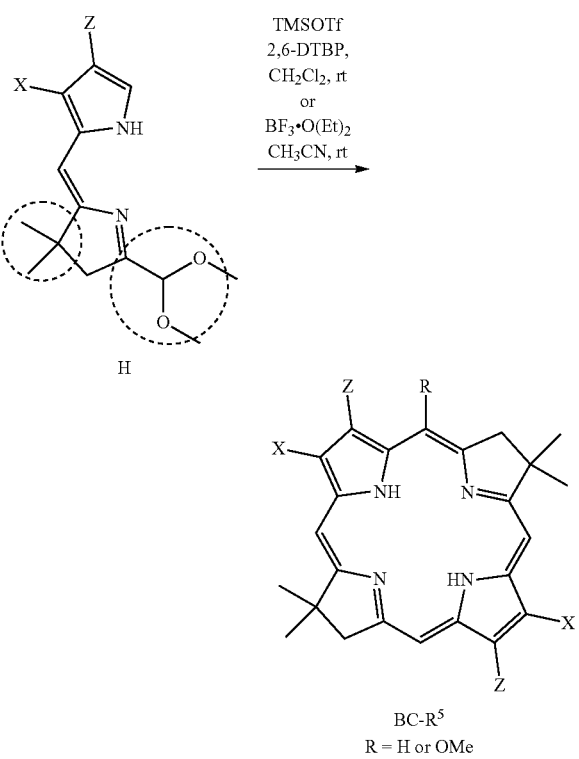

BC-R⁵
R = H or OMe

New Northern-Southern Route

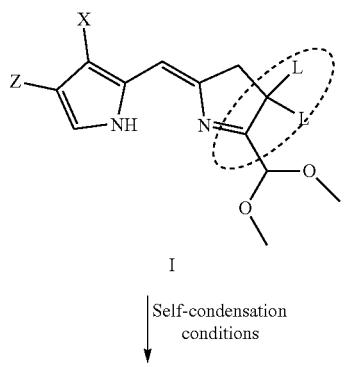

Self-condensation conditions

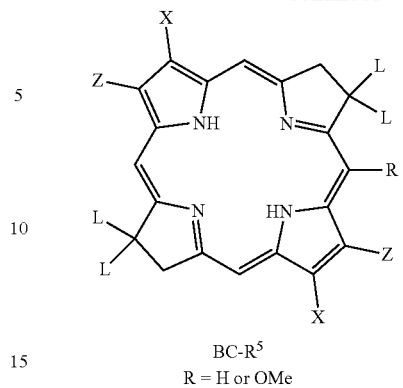

BC-R⁵
R = H or OMe

Disclosed herein is the synthesis of the new dihydrodipyrrins of type I (L=Me) required for the Northern-Southern route to bacteriochlorins. We then examine the synthesis of a variety of novel bacteriochlorins that contain previously unaccessed substituent patterns at the β-pyrrole and meso-positions.

Results and Discussion

I. Northern-Southern Route to Bacteriochlorin Development

The synthetic route towards 2,2-dimethyldihydrodipyrrins in this work largely followed Jacobi's methodology. However, bacteriochlorin formation reaction requires a free α-position on the pyrrole of the dihydrodipyrrin-acetal, which enables distinctive β-substituents design for pyrroles. Here, ethyl 2-iodo-4-ethyl-pyrrole-3-carboxylate 2a was chosen for the first attempt and simple demonstration (Scheme 5). After adjusting the reactant ratio from Jacobi's procedure, the Pd-coupling reaction between these two partners worked well to provide 3aa in 87% yield. Further transformation of 3aa by the Petasis reagent gave 4aa in 71% yield. Compound 4aa was easily hydrolyzed under acidic conditions and converted to dihydrodipyrrin 5aa via a Paal-Knorr type of ring formation. The 1-methyl group of dihydrodipyrrin 5aa was converted with SeO$_2$ and HC(OMe)$_3$ to the corresponding acetal (6aa) following a reported procedure[304] of similar compounds.

Scheme 5. Northern-southern self-condensation to bacteriochlorins: route development

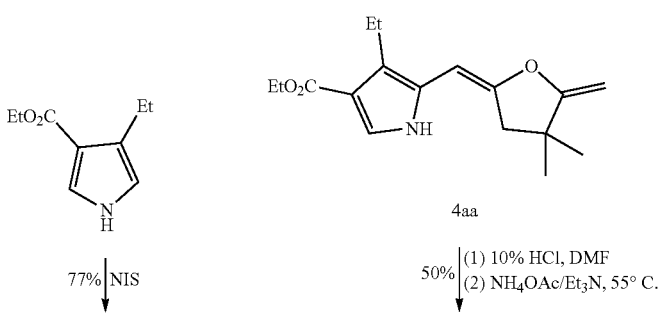

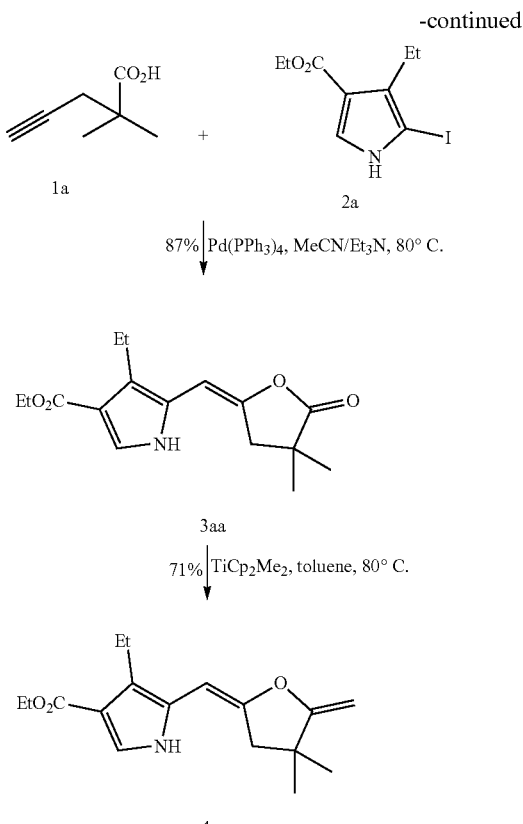
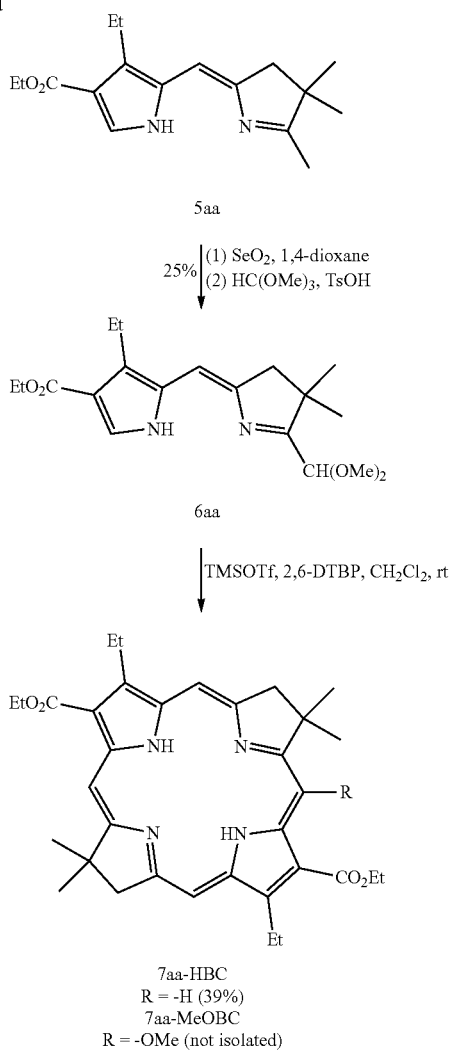

7aa-HBC
R = -H (39%)
7aa-MeOBC
R = -OMe (not isolated)

With 2,2-dimethyldihydrodipyrrin-acetal 6aa in hand, we tried to synthesize bacteriochlorins following our existing method. With numerous 3,3-dimethyldihydrodipyrrin-acetals, the general reaction conditions of TMSOTf and 2,6-di-tert-butylpyridine (2,6-DTBP) in $CH_2Cl_2$ at room temperature typically afford the 5-methoxybacteriochlorin to the exclusion of any 5-unsubstituted bacteriochlorin.[265] Indeed, for the 3,3-dimethyldihydrodipyrrin-acetal 6aa' with identical pyrrole substituents (but position-interchanged versus that for 6aa), the yield of the 5-methoxybacteriochlorin was 42%. Here, 6aa gave 5-unsubstituted bacteriochlorin 7aa-HBC in 39% yield while no 5-methoxybacteriochlorin 7aa-MeOBC was isolated.

The absence of the meso-methoxy group is an unexpected result we have never observed previously under these reaction conditions. It is tempting to attribute this result to the steric hindrance from the position changes of the geminal dimethyl groups, which makes the 10-MeOBC less stable. Prior studies were inconclusive concerning the mechanism of HBC formation and the nature of the requisite reductant. The UV-Vis absorption spectrum of bacteriochlorin 7aa-HBC is almost identical with that of the related 7aa'-HBC that we synthesized previously,[265] which is consistent with our general understanding that the presence of the dimethyl group in the pyrroline ring has little influence on the π electron orbitals of the macrocycle.

II. Synthesis of Meso-Disubstituted Bacteriochlorins Via Meso-Substituted Dihydrodipyrrins Two types of meso-aryl bacteriochlorins have been prepared to date. Hydrogenation of a meso-tetraarylporphyrin gives the corresponding meso-tetraarylbacteriochlorin, a procedure first described by Whitlock and coworkers 45 years ago.[41] The bacteriochlorins so-formed are susceptible to dehydrogenation to form the chlorins and porphyrins. Such bacteriochlorin, chlorin, and porphyrin species are separated with difficulty. A second type of meso-tetraarylbacteriochlorins accessed from vicinal dihydroxylation with $OsO_4$, which typically forms syn and anti isomers.[42] We sought to exploit the new route to dihydrodipyrrins to gain access to bacteriochlorins bearing two-aryl substituents.

To synthesize meso-substituted bacteriochlorins, the corresponding 5-substituted 2,2-dimethylpent-4-ynoic acid precursors were prepared following the reported procedure for known or similar compounds:[6(a), 6(c)] (1) alkyl substituents were introduced as the 1-alkyl substituted propargyl bromide; and (2) aryl substituents were installed via sonogashira coupling reactions (Scheme 6).

Scheme 6. Preparation of meso-substituted bacteriochlorin acid precursors

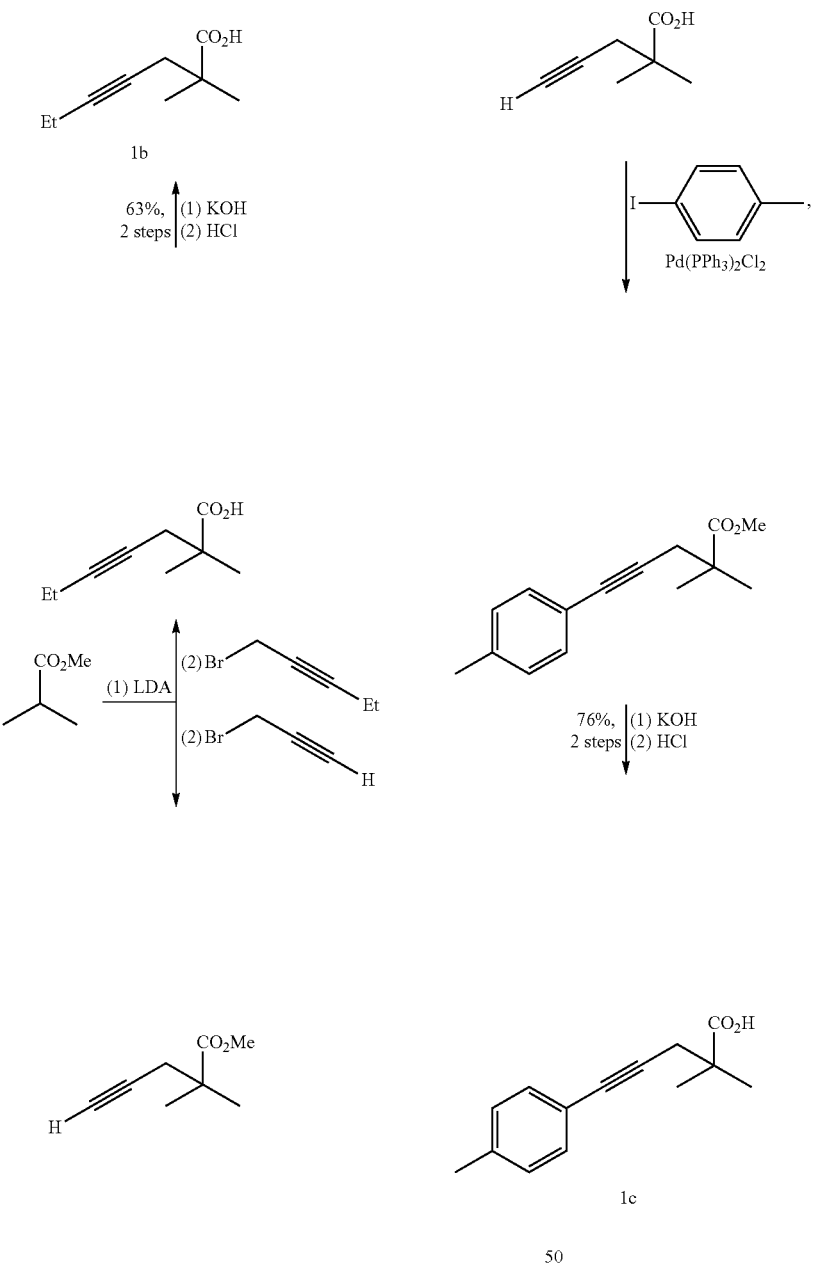

Different combinations of the substituted pentynoic acids and halopyrroles were then explored. The original Pd-coupling reaction condition worked well for Pyrrole 2b, which only has one β-substituent, with all kinds of acid precursors; however, Pyrrole 2a and 2d gave poor yield to afford the meso-substituted lactone product. This difficulty may stem from the steric hindrance between β-pyrrole and meso-substituents of the target molecules, and it could be largely resolved by with higher reaction temperature (Scheme 7). Following TiCp$_2$Cl$_2$ treatment and the Paal-Knorr typical of ring formation, six dihydrodipyrrins with different meso- and β-substitution patterns were prepared and they were all successfully converted to the corresponding dihydrodipyrrin-acetal.

Scheme 7. Preparation of meso-substituted dihydrodipyrrin-acetals

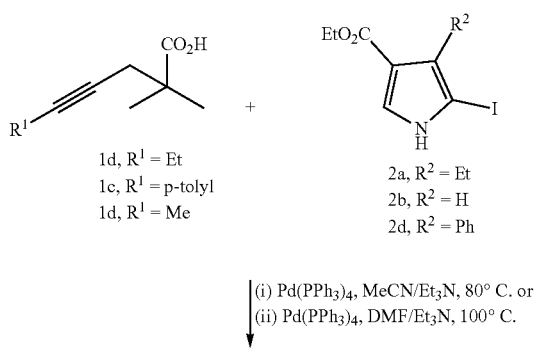

-continued

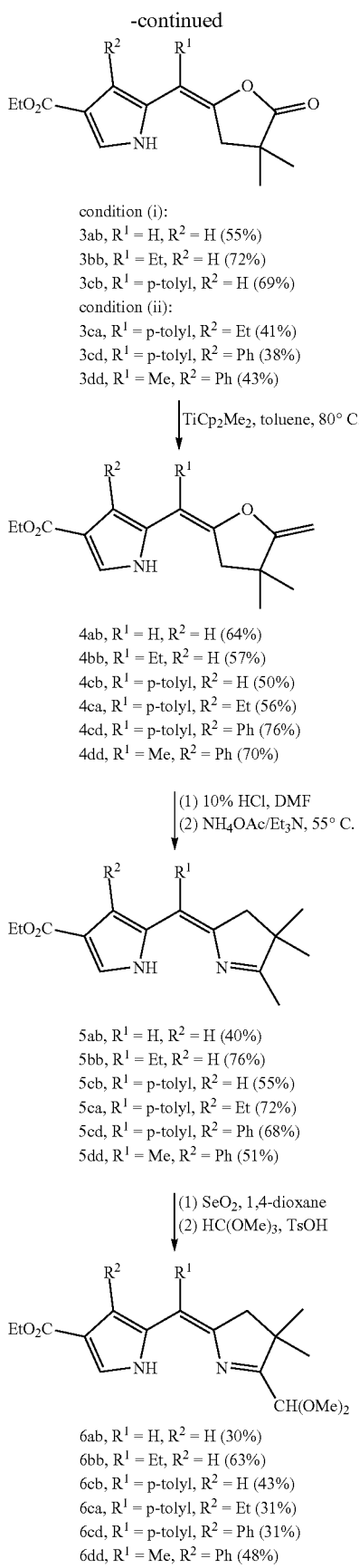

condition (i):
3ab, R$^1$ = H, R$^2$ = H (55%)
3bb, R$^1$ = Et, R$^2$ = H (72%)
3cb, R$^1$ = p-tolyl, R$^2$ = H (69%)
condition (ii):
3ca, R$^1$ = p-tolyl, R$^2$ = Et (41%)
3cd, R$^1$ = p-tolyl, R$^2$ = Ph (38%)
3dd, R$^1$ = Me, R$^2$ = Ph (43%)

TiCp$_2$Me$_2$, toluene, 80° C.

4ab, R$^1$ = H, R$^2$ = H (64%)
4bb, R$^1$ = Et, R$^2$ = H (57%)
4cb, R$^1$ = p-tolyl, R$^2$ = H (50%)
4ca, R$^1$ = p-tolyl, R$^2$ = Et (56%)
4cd, R$^1$ = p-tolyl, R$^2$ = Ph (76%)
4dd, R$^1$ = Me, R$^2$ = Ph (70%)

(1) 10% HCl, DMF
(2) NH$_4$OAc/Et$_3$N, 55° C.

5ab, R$^1$ = H, R$^2$ = H (40%)
5bb, R$^1$ = Et, R$^2$ = H (76%)
5cb, R$^1$ = p-tolyl, R$^2$ = H (55%)
5ca, R$^1$ = p-tolyl, R$^2$ = Et (72%)
5cd, R$^1$ = p-tolyl, R$^2$ = Ph (68%)
5dd, R$^1$ = Me, R$^2$ = Ph (51%)

(1) SeO$_2$, 1,4-dioxane
(2) HC(OMe)$_3$, TsOH

6ab, R$^1$ = H, R$^2$ = H (30%)
6bb, R$^1$ = Et, R$^2$ = H (63%)
6cb, R$^1$ = p-tolyl, R$^2$ = H (43%)
6ca, R$^1$ = p-tolyl, R$^2$ = Et (31%)
6cd, R$^1$ = p-tolyl, R$^2$ = Ph (31%)
6dd, R$^1$ = Me, R$^2$ = Ph (48%)

The bacteriochlorin formation reaction generally gave HBC with higher yields compared to the results we reported before, except lab-HBC (entry 1), which is from a relatively electron deficient dihydrodipyrrin-acetal (Table 1). 7cb-MeOBC (entry 3) is the only bacteriochlorin bearing a meso-methoxy group that was isolated. Again, we believe the steric effects from the gem-dimethyl groups on the β-pyrroline rings are the major reason for the absence of the meso-methoxy groups.

TABLE 1

Synthesis of meso-substitutedbacteriochlorins

| Entry | DHDPA | R$^1$ | R$^2$ | R | BC | Yield (%) |
|---|---|---|---|---|---|---|
| 1 | 6ab | H | H | H | 7ab-HBC | 6.0 |
| 2 | 6bb | Et | H | H | 7bb-HBC | 35 |
| 3 | 6cb | p-tolyl | H | H | 7cb-HBC | 38 |
|   |     |         |   | OMe | 7cb-MeOBC | 9.1 |
| 4 | 6ca | p-tolyl | Et | H | 7ca-HBC | 33 |
| 5 | 6cd | p-tolyl | Ph | H | 7cd-HBC | 32 |
| 6 | 6dd | Me | Ph | H | 7dd-HBC | 29 |

III. Synthesis of Novel Bacteriochlorins with No β-Ester Substituents.

While all the above examples have ethyl ester on the β-pyrrole positions, it was tempting to also synthesize bacteriochlorins with β-ester substituents. To access such substitution patterns, an electron-withdrawing group is still essential to stabilize the halopyrrole precursor. Here, a straightforward strategy is to put a tert-butyl ester on the α-position we plan to free up in the later stage of the synthesis. Therefore, the bromo-pyrrole 2c was chosen as the starting material. As a general rule, the electrophilic aromatic substitution of a pyrrole bearing an electron-withdrawing group at the 2-position generally proceeds at the 4-position. However, this rule does not apply to all substrates satisfactorily, for example, the halogenation of a pyrrole-2-carboxylate gave very poor selectivity and, as some early references described,' afforded complicated mixtures. As a result, the synthesis of 4-bromo-pyrrole-2-carboxylates was usually conducted via bromination of a 2-trichloroacetylpyrrole followed by treatment with NaOMe. Nevertheless, taking advantage of this poor selectivity also provided the potential of preparing 5-halo-pyrrole-2-carboxylates directly from halogenation of pyrrole 2-carboxylates. In 2006, Trost and Dong successfully prepared the methyl 5-bromo-pyrrole-2-carboxylate via bromination of methyl pyrrole-2-carboxylate.[8] We applied the same procedure to tert-butyl pyrrole-2-carboxylate 9 and obtained the similar tert-butyl 5-bromo-pyrrole-2-carboxylate 2c (Scheme 8).

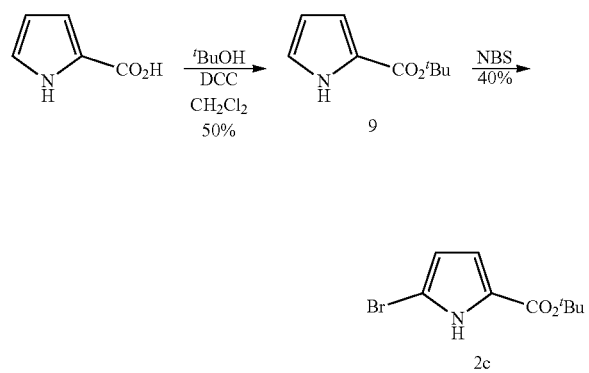

With pyrrole 2c in hand, dihydrodipyrrin-acetal 6cc was successfully obtained (Scheme 9). However, treating this dihydrodipyrrin-acetal with various Lewis acids (TMSOTf/ 2,6-DTBP, neat TFA or BF$_3$.Et$_2$O) did not provide any bacteriochlorin, likely due to the problematic ester cleavage and/or decarboxylation under these conditions. Attempts to cleave and decarboxylate the dihydrodipyrrin 5cc were also unsuccessful.

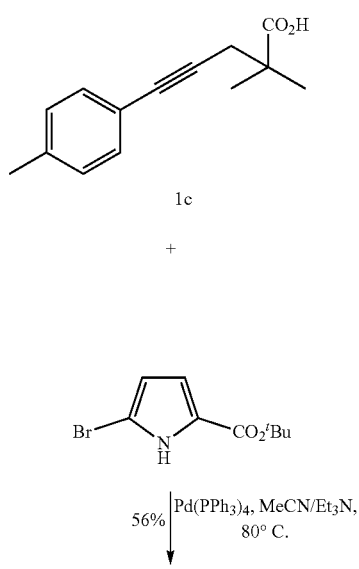

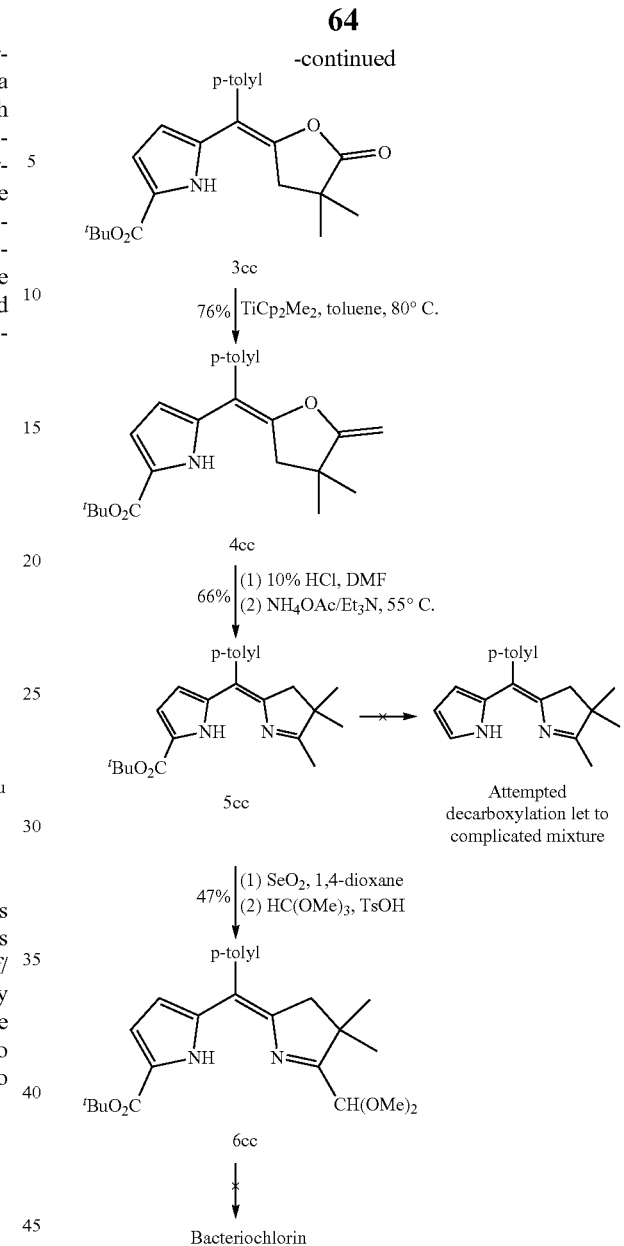

One possible reason for difficult decarboxylation of dihydrodipyrrins, as pointed out by Jacobi,[6(b)] is the competition of protonation on the N atoms in the pyrroline rings. We also would like to mention that the resulting protonated species is expected to be highly reactive as demonstrated in our previous work,[120] where an intramolecular cyclization was observed for a similar tetrahydropyrrin under acid conditions. Here due to the relatively rigid structure of dihydrodipyrrins, strong decomposition was observed.

Therefore, we attempted to remove the tert-butyl ester at an earlier stage. Ene-lactone 3cc was chosen to be the substrate as it is relatively stable; moreover, the pyrrole of 3cc is also more electron-rich, which may facilitate the decarboxylation. Treating 3cc with a 1:1 mixed solution of TFA and CH$_2$Cl$_2$ for 2 hours at room temperature gave the desired product 3cc-DC. Subsequent steps afforded the desired dihydrodippyrin 5cc-DC. However, the SeO$_2$ oxidation of 5cc-DC led to unstable product and could not be further converted to any bacteriochlorin (Scheme 10).

Scheme 10. Synthesis of a bacteriochlorin with meso-substituents and no β-substituents (II)

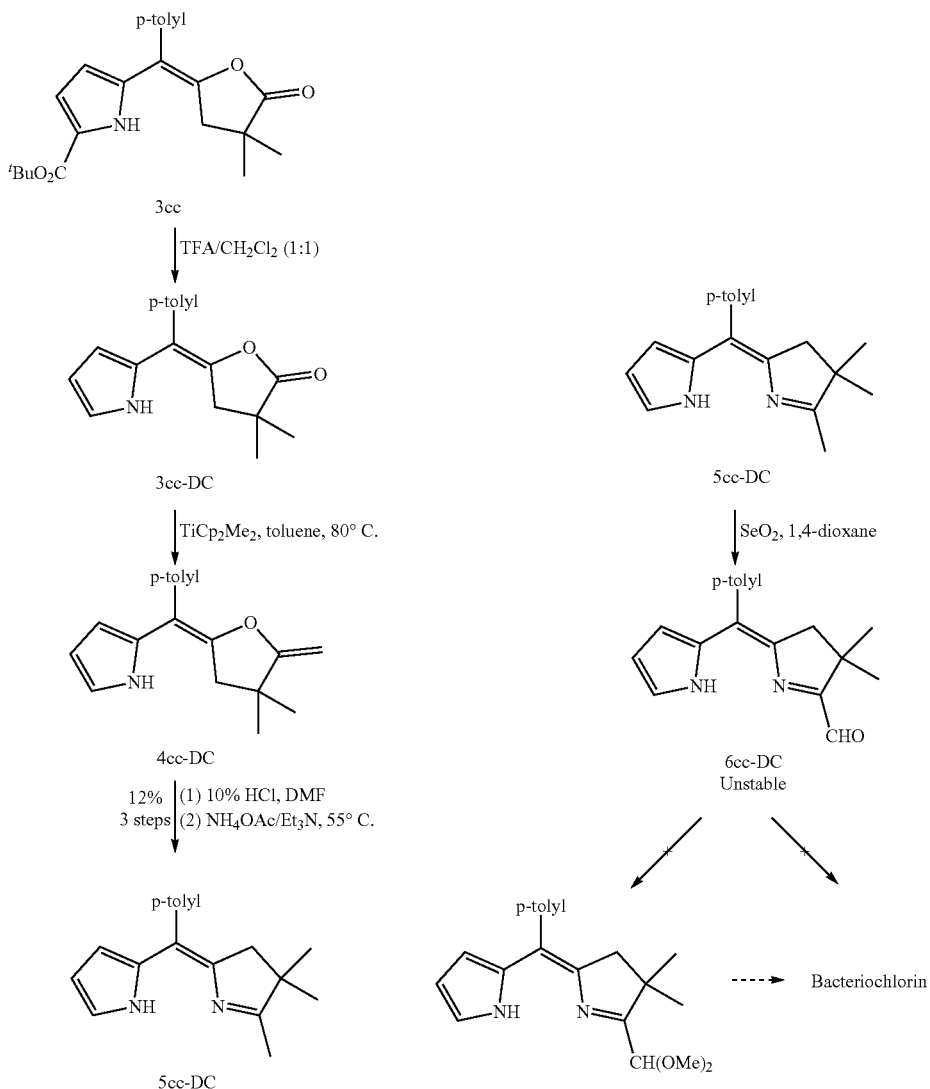

Afterwards, we also attempted to install β- or/and meso-substituents on the bacteriochlorin via this route. The β-substituents could be installed by a bromination on the ene-lactone 3ac followed by a Suzuki coupling. However, the resulting intermediates of these syntheses were generally unstable. Thus, the decarboxylated ene-lactone 3ac'-Ph was quickly decomposed and failed to give the desired product 4ac'-Ph under Petasis reagent treatment (Scheme 11).

Scheme 11. Synthesis of a bacteriochlorin with β-aryl but no meso-substituent

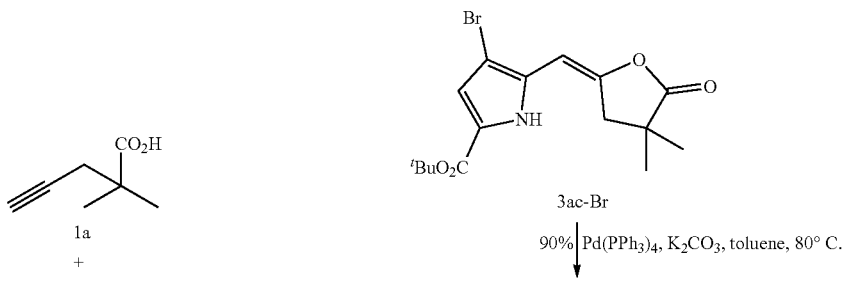

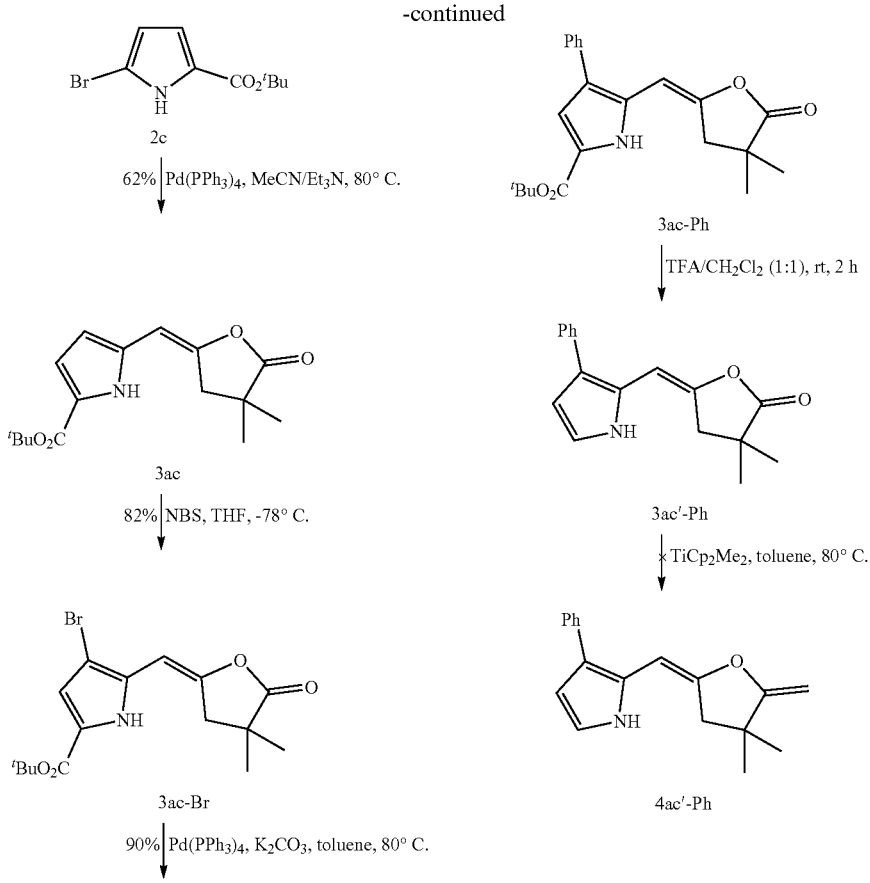

Finally, we attempted to prepare a bacteriochlorin without any peripheral substituents. Treating 3ac with a 1:1 mixed solution of TFA and $CH_2Cl_2$ for 2 hours at room temperature gave the desired product 3ac', which was not isolated but directly treated with Petasis reagent. The resulting compound 4ac' was easily converted to a dihydrodipyrrin 5ac-DC. TLC analysis showed the following $SeO_2$ oxidation of 5ac-DC happened in 1,4-dioxane, but the resulting aldehyde was not stable enough to be isolated or further converted to the corresponding acetal. Fortunately, Treating 5ac-DC with $SeO_2$ in $CH_2Cl_2$ followed immediately by TMSOTf/2,6-DTBP gave the desired bacteriochlorin 7ac-HBC in about 6% yield (Scheme 12).

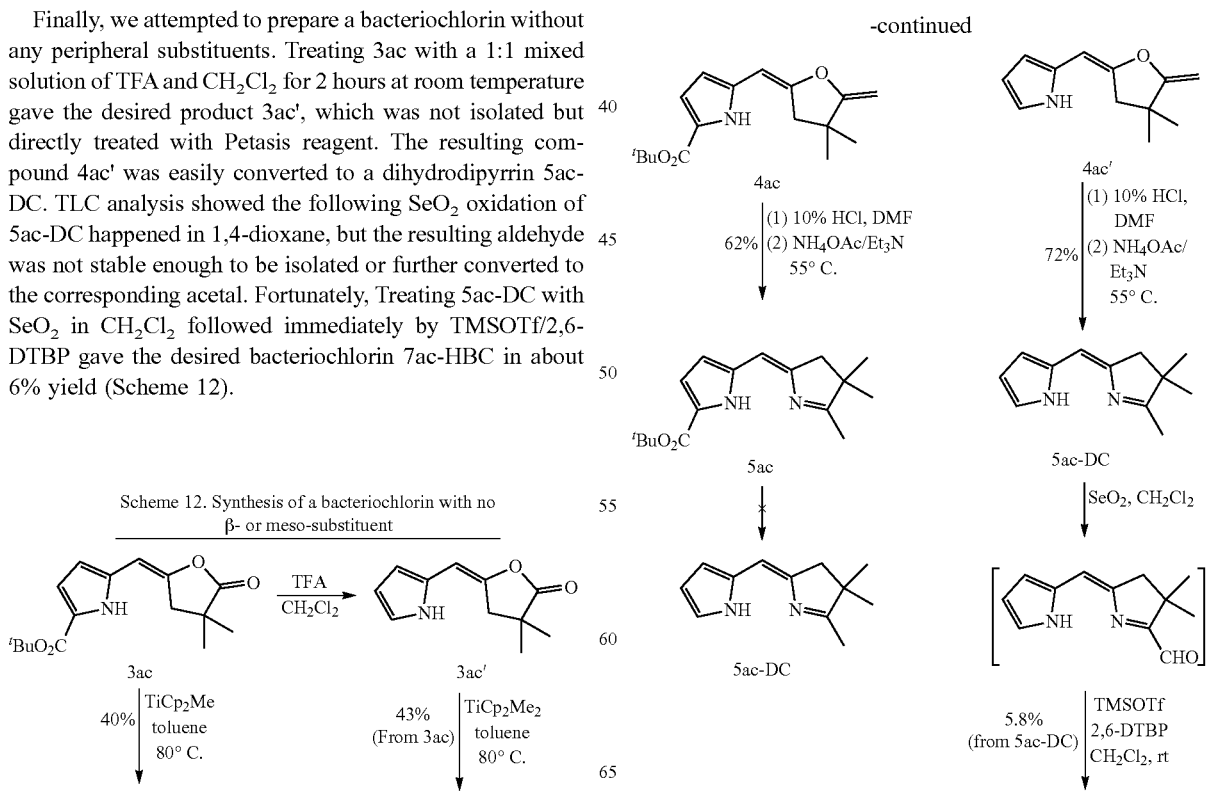

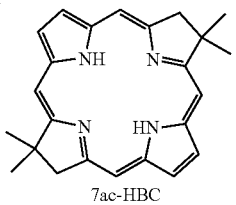

7ac-HBC

Characterization

All new compounds and existing compounds synthesized via new pathways were fully characterized with $^1$H NMR (300 MHz), $^{13}$C NMR (75 MHz) and electrospray ionization mass spectrometry (ESI-MS). Melting points were measured for compounds that appeared to be solid. Compounds 2, 3, 4, 5 are generally solids unless otherwise indicated. Single-crystal X-ray structures of compound 3cc, 3ca, 7bb-HBC and 7cb-HBC were analyzed (not shown). The X-ray structure of 3cc indicated a trans-conformation of Pyrrole and meso-H in the lattice, which is to minimize the β- and meso-substituents (both hydrogen atoms in this case). The Northern-Southern self-condensation was also confirmed by the X-ray patterns of compound 7bb-HBC and 7cb-HBC.

UV-Vis spectra of all bacteriochlorins synthesized were measured. They all match the typical UV-Vis spectra of bacteriochlorins. Novel meso-disubstituted bacteriochlorins first prepared in this work have $Q_y$ bands at near IR region of 753-760 nm (data not shown).

CONCLUSIONS

The modification of Jacobi's route of dihydrodipyrrin synthesis to prepare precursors has afforded a new pathway to synthetic bacteriochlorins. This study has (1) revealed a new Northern-Southern self-condensation to provide bacteriochlorins, (2) enabled the syntheses of previously inaccessible substitution patterns, such as the meso-disubstituted bacteriochlorins.

Experimental Section

General Methods.

$^1$H NMR (300 MHz) and $^{13}$C NMR (75 MHz) spectra were collected at room temperature in CDCl$_3$ unless noted otherwise. Silica gel (40 μm average particle size) was used for column chromatography. All solvents were reagent grade and were used as received unless noted otherwise. THF was freshly distilled from sodium/benzophenone ketyl. Electrospray ionization mass spectrometry (ESI-MS) data are reported for the molecular ion, protonated molecular ion, or sodium-cationized molecular ion. Commercial compounds are used as received.

Ethyl 4-ethyl-5-iodo-1H-pyrrole-3-carboxylate (2a)

A stirred solution of ethyl 4-ethyl-1H-pyrrole-3-carboxylate (1.67 g, 10 mmol) in dry DMF (50 mL) was treated with NIS (2.25 g, 10 mmol) in batches at 0° C. After 1 h, ethyl acetate (100 mL) was added. The mixture was washed with water and brine. The organic layer was dried (Na$_2$SO$_4$) and concentrated. Column chromatography [silica, hexanes/ethyl acetate (1:6)] afforded a white solid (2.26 g, 77%): mp 95-96° C.; $^1$H NMR δ 1.11 (t, J=7.2 Hz, 3H), 1.33 (t, J=6.9 Hz, 3H), 2.67 (q, J=7.2 Hz, 2H), 4.27 (q, J=6.9 Hz, 2H), 7.47 (d, J=2.7 Hz, 1H), 8.36 (s, 1H); $^{13}$C NMR δ 15.6, 24.2, 30.3, 55.3, 70.6, 73.0, 103.1, 127.6, 127.8, 128.5, 138.8; ESI-MS obsd 293.9980, calcd 293.9987 [(M+H)$^+$, M=C$_9$H$_{12}$NO$_2$I].

Ethyl 5-[(4,4-dimethyl-5-methylenedihydrofuran-2 (3H)-ylidene)methyl]-4-ethyl-1H-pyrrole-3-carboxylate (3aa)

Following a general procedure,[6] a solution of 1a (1.26 g, 10.1 mmol), 2a (1.48 g, 5.05 mmol) and BnNEt$_3$Cl (1.15 g, 5.05 mmol) in dry acetonitrile (20 mL) and Et$_3$N (5 mL) was added to a Schlenk flask and deaerated by three freeze-pump-thaw cycles. A sample of Pd(PPh$_3$)$_4$ (293 mg, 0.253 mmol) was then added, and the resulting mixture was further deaerated. The reaction mixture was kept at 80° C. for 24 h, and then CH$_2$Cl$_2$ and water were added. The organic layer was dried (Na$_2$SO$_4$) and concentrated. Column chromatography [silica, hexanes/ethyl acetate (3:1)] afforded a clear yellow solid (2.55 g, 87%): mp 128-129° C.; $^1$H NMR δ 1.12 (t, J=7.2 Hz, 3H), 1.31-1.36 (m, 9H), 2.72 (q, J=7.2 Hz, 2H), 4.27 (q, J=6.9 Hz, 2H), 6.22 (s, 1H), 7.39 (d, J=3.3 Hz, 1H), 8.58 (s, 1H); $^{13}$C NMR δ 24.0, 39.6, 69.5, 73.0, 127.8, 128.6, 138.6, 210.6; ESI-MS obsd 292.1539, calcd 292.1543 [(M+H)$^+$, M=C$_{16}$H$_{21}$NO$_4$].

Ethyl 5-[(4,4-dimethyl-5-methylenedihydrofuran-2 (3H)-ylidene)methyl]-4-ethyl-1H-pyrrole-3-carboxylate (4aa)

Following a standard procedure,[6] a solution of TiCp$_2$Cl$_2$ (3.045 g, 12.37 mmol) in toluene (33 mL) was treated dropwise with LiMe solution (1.6 M, 17 mL in Et$_2$O, 27 mmol) at 0° C. under an argon atmosphere. After 1 h at 0° C., saturated aqueous NH$_4$Cl solution was added. The organic layer was washed (water and brine), dried (Na$_2$SO$_4$) and filtered. The filtrate was treated with lactone 3aa (760 mg, 2.61 mmol) and TiCp$_2$Cl$_2$ (39 mg). The solution was heated to 80° C. in the dark for 6 h under argon. Afterwards, the resulting mixture was allowed to cool to room temperature whereupon MeOH (3.1 mL), NaHCO$_3$ (130 mg) and water (31 μL) were added. The mixture was kept at 40° C. for another 12 h with stirring and then filtered through Celite. The filtrate was concentrated. Column chromatography [silica, hexanes/ethyl acetate (3:1)] afforded a clear orange solid (536 mg, 71%): mp 101-102° C.; $^1$H NMR δ 1.11 (t, J=7.2 Hz, 3H), 1.24 (s, 6H), 1.33 (t, J=6.9 Hz, 3H), 2.62 (s, 2H), 2.75 (q, J=7.2 Hz, 2H), 4.01 (d, J=2.4 Hz, 1H), 4.26 (q, J=6.9 Hz, 2H), 4.40 (d, J=2.4 Hz, 1H), 5.91 (s, 1H), 7.35 (d, J=3.3 Hz, 1H), 8.19 (s, 1H); $^{13}$C NMR δ 3.7, 25.1, 39.9, 70.6, 70.7, 73.0, 80.5, 82.1, 127.8, 128.5, 138.4; ESI-MS obsd 290.1742, calcd 290.1751 [(M+H)$^+$, M=C$_{17}$H$_{23}$NO$_3$].

7-Ethyl-8-(ethoxycarbonyl)-1-methyl-2,2-dimethyl-2,3-dihydrodipyrrin (5aa)

Following a general procedure,[6] a solution of 4aa (569 mg, 1.97 mmol) in DMF (20 mL) was treated with 1M HCl (1.0 mL). After 30 min, NH$_4$OAc (3.03 g, 39.5 mmol) and Et$_3$N (5.4 mL, 40 mmol) were added, and the resulting mixture was stirred at 55° C. for 4 h. Then, the reaction was quenched by the addition of saturated aqueous KH$_2$PO$_4$ solution. Ethyl acetate (100 mL) was added, and the organic layer was washed (water), dried and concentrated. Column chromatography [silica, hexanes/ethyl acetate (3:1)] afforded a light yellow solid (281 mg, 50%): mp 117-119° C.; $^1$H NMR δ 1.14-1.18 (m, 9H), 1.35 (t, J=6.9 Hz, 3H), 2.08 (s, 3H), 2.62 (s, 2H), 2.79 (q, J=7.2 Hz, 2H), 4.27 (q, J=6.9 Hz, 2H), 5.93 (s, 1H), 7.39 (d, J=3.3 Hz, 1H), 11.1 (bs, 1H); $^{13}$C NMR δ 28.0, 28.8, 29.3, 32.1, 35.3, 69.6, 70.5, 73.0, 73.1, 123.6, 127.8, 128.5, 128.6, 138.5, 138.7, 162.2, 198.4; ESI-MS obsd 289.1910, calcd 289.1910 [(M+H)$^+$, M=$C_{17}H_{24}N_2O_2$].

7-Ethyl-8-(ethoxycarbonyl)-1-(1,1-dimethoxymethyl)-2,2-dimethyl-2,3-dihydrodipyrrin (6aa)

Following a general procedure,[304] a solution of 5aa (245 mg, 0.851 mmol) in 1,4-dioxane (15 mL) was treated with SeO$_2$ (284 mg, 2.55 mmol). The reaction mixture was stirred at room temperature for 30 min. Ethyl acetate and water were then added. The organic layer was washed (brine), dried and concentrated to dryness. The crude product was treated directly with HC(OMe)$_3$ (7 mL) and TsOH.H$_2$O (48 mg, 0.25 mmol). After 12 h with stirring at room temperature, the reaction mixture was quenched by the addition of saturated aqueous NaHCO$_3$ solution, and then extracted with ethyl acetate. The organic layer was dried (Na$_2$SO$_4$) and concentrated. Column chromatography [silica, hexanes/ethyl acetate (4:1)] afforded a brown oil (74 mg, 25%): $^1$H NMR δ 1.16 (t, J=7.2 Hz, 3H), 1.27 (s, 6H), 1.33 (t, J=6.9 Hz, 3H), 2.61 (s, 2H), 2.78 (q, J=7.2 Hz, 2H), 3.44 (s, 6H), 4.28 (q, J=6.9 Hz, 2H), 5.10 (s, 1H), 6.01 (s, 1H), 7.41 (d, J=3.3 Hz, 1H), 10.96 (bs, 1H); $^{13}$C NMR δ 28.0, 32.7, 70.2, 73.1, 109.4, 127.8, 128.6, 138.8, 148.8; ESI-MS obsd 349.2141, calcd 349.2122 [(M+H)$^+$, M=$C_{19}H_{28}N_2O_4$].

Diethyl 8,8,18,18-tetramethyl-3,13-diethylbacteriochlorin-2,12-dicarboxylate (7aa-HBC)

Following a general procedure,[265] a solution of 6aa (47 mg, 0.16 mmol) in anhydrous CH$_2$Cl$_2$ (9 mL) was treated with 2,6-DTBP (735 µL, 3.2 mmol) followed by TMSOTf (150 µL, 0.80 mmol). The reaction mixture was stirred at room temperature for 15 h, and then diluted with CH$_2$Cl$_2$ and washed with saturated aqueous NaHCO$_3$. The organic layer was dried (Na$_2$SO$_4$) and concentrated. Column chromatography [silica, hexanes/ethyl acetate (4:1)] afforded a dark green solid (15 mg, 39%): $^1$H NMR δ −1.46 (s, 2H), 1.25 (t, J=7.2 Hz, 6H), 1.71-1.78 (m, 14H), 1.96 (s, 12H), 4.13 (q, J=7.2 Hz, 4H), 4.40 (s, 4H), 4.79 (q, J=6.9 Hz, 4H), 8.77 (s, 2H), 9.62 (s, 2H); $^{13}$C NMR δ 14.9, 17.8, 20.8, 31.3, 46.4, 51.7, 61.0, 96.81, 96.89, 132.7, 135.8, 159.3, 166.6, 172.6; ESI-MS obsd 571.3265, calcd 571.3279 [(M+H)$^+$, M=$C_{34}H_{42}N_4O_4$]; $\lambda_{abs}$ 353, 383, 519, 758 nm (CH$_2$Cl$_2$).

2,2-Dimethylhept-4-ynoic acid (1b)

A solution of methyl isobutyrate (4.54 g, 50.0 mmol) in anhydrous THF (50 mL) was treated with LDA solution (2.0 M, 25 mL in THF/heptane/ethylbenzene, 50 mmol) at −78° C. under argon. After 30 min, 1-bromopent-2-yne (7.35 g, 50.0 mmol) was added dropwise, and the reaction mixture was allowed to warm to room temperature. After 1 h at room temperature, the reaction was quenched by the addition of saturated aqueous NH$_4$Cl solution. The organic layer was extracted with diethyl ether. The combined organic extract was dried (Na$_2$SO$_4$) and concentrated. To the resulting oil, KOH (8.4 g, 150 mmol), water (10 mL), MeOH (10 mL), and THF (30 mL) were added, and the mixture was stirred overnight under argon. Afterwards, 6 M HCl solution was added until the reaction mixture exhibited pH=1. The resulting mixture was extracted with CH$_2$Cl$_2$. The organic fraction was dried (Na$_2$SO$_4$) and concentrated to afford a colorless oil which was used without further purification (4.85 g, 63%): $^1$H NMR δ 1.11 (t, J=6.8 Hz, 3H), 1.27 (s, 6), 2.15 (qd, J=2.4 Hz, J=7.2 Hz, 2H), 2.40 (t, J=2.4 Hz, 2H); $^{13}$C NMR δ 12.6, 14.4, 24.5, 29.9, 42.5, 75.8, 84.5; ESI-MS obsd 155.1071, calcd 155.1066 [(M+H)$^+$, M=$C_9H_{14}O_2$];

Ethyl 5-iodo-1H-pyrrole-3-carboxylate (2b)

A stirred solution of ethyl 1H-pyrrole-3-carboxylate (1.39 g, 10 mmol) in dry DMF (50 mL) was treated with NIS (2.25 g, 10 mmol) in batches at 0° C. After 1 h, ethyl acetate (100 mL) was added. The mixture was washed with water and brine. The organic layer was dried (Na$_2$SO$_4$) and concentrated. Column chromatography [silica, hexanes/ethyl acetate (1:3)] afforded a yellow solid (1.59 g, 60%): mp 86-88° C.; $^1$H NMR δ 1.33 (t, J=6.9 Hz, 3H), 4.29 (q, J=6.9 Hz, 2H), 6.78 (dd, J=1.7, 2.8 Hz, 1H), 7.42 (dd, J=1.7, 2.8 Hz, 1H), 9.72 (bs, 1H); $^{13}$C NMR δ 14.7, 60.7, 64.1, 119.0, 119.2, 127.9, 164.8; ESI-MS obsd 265.9683, calcd 265.9674 [(M+H)$^+$, M=$C_7H_8INO_2$].

(E)-Ethyl 5-[1-(4,4-dimethyl-5-oxodihydrofuran-2(3H)-ylidene)propyl]-1H-pyrrole-3-carboxylate (3bb)

Following a general procedure,[6] a solution of 1b (2.36 g, 15.3 mmol), 2b (1.35 g, 5.10 mmol) and BnNEt$_3$Cl (1.16 g, 5.06 mmol) in dry acetonitrile (20 mL) and Et$_3$N (5 mL) was added to a Schlenk flask and deaerated by three freeze-pump-thaw cycles. A sample of Pd(PPh$_3$)$_4$ (383 mg, 0.332 mmol) was then added and the resulting mixture was further deaerated. The reaction mixture was kept at 80° C. for 24 h, and then CH$_2$Cl$_2$ and water were added. The organic layer was dried (Na$_2$SO$_4$) and concentrated. Column chromatography [silica, hexanes/ethyl acetate (3:1)] afforded a light yellow solid (1.06 g, 72%): mp 121-122° C.; $^1$H NMR δ 1.04 (t, J=7.4 Hz, 3H), 1.31-1.38 (m, 9H), 2.52 (q, J=7.4 Hz, 2H), 2.88 (s, 2H), 4.30 (q, J=7.2 Hz, 2H), 6.44 (s, 1H), 7.42 (s, 1H), 8.76 (s, 1H); $^{13}$C NMR δ 13.7, 14.7, 22.3, 25.3, 40.3, 41.3, 60.2, 108.7, 111.7, 117.4, 123.4, 129.8, 143.7, 165.2, 180.3; ESI-MS obsd 292.1539, calcd 292.1543 [(M+H)$^+$, M=$C_{16}H_{21}NO_4$].

(E)-Ethyl 5-[1-(4,4-dimethyl-5-methylenedihydrofuran-2(3H)-ylidene)propyl]-1H-pyrrole-3-carboxylate (4bb)

Following a general procedure,[6] a solution of TiCp$_2$Cl$_2$ (4.25 g, 17.25 mmol) in toluene (40 mL) was treated dropwise with LiMe solution (1.6 M, 24 mL in Et$_2$O, 38 mmol) at 0° C. under an argon atmosphere, then the resulting solution was stirred at 0° C. After 1 h at 0° C., saturated aqueous NH$_4$Cl solution was added. The organic layer was washed (water and brine), dried (Na$_2$SO$_4$) and filtered. The filtrate was treated with lactone 3bb (1.06 g, 3.63 mmol) and TiCp$_2$Cl$_2$ (56 mg). The resulting solution was heated to 80° C. in the dark for 6 h. Afterwards, the resulting mixture was allowed to cool to room temperature whereupon MeOH (4.3 mL), NaHCO$_3$ (180 mg) and water (43 µL) were added. The resulting solution was kept at 40° C. for another 12 h with stirring and then filtered through Celite. The filtrate was concentrated. Column chromatography [silica, hexanes/ethyl acetate (3:1)] afforded a brown solid (601 mg, 57%): mp 106-108° C.; $^1$H NMR δ 1.04 (t, J=7.4 Hz, 3H), 1.21 (s, 6H), 1.34 (t, J=7.2 Hz, 3H), 2.48 (q, J=7.2 Hz, 2H), 2.62 (s, 2H), 3.98 (d, J=2.2 Hz, 1H), 4.29 (q, J=7.2 Hz, 2H), 4.38 (d, J=2.2 Hz, 1H), 6.37 (s, 1H), 7.36 (dd, J=3, 1.7 Hz, 1H), 8.34 (s, 1H); $^{13}$C NMR δ 3.7, 25.1, 39.9, 70.6, 70.7, 73.0, 80.5, 82.1, 127.8, 128.5, 138.4; ESI-MS obsd 290.1748, calcd 290.1751 [(M+H)$^+$, M=C$_{17}$H$_{23}$NO$_3$].

5-Ethyl-8-(ethoxycarbonyl)-1-methyl-2,2-dimethyl-2,3-dihydrodipyrrin (5bb)

Following a general procedure,[6] a solution of 4bb (601 mg, 2.07 mmol) in DMF (20 mL) was treated with 1 M HCl (1.0 mL). After 30 min, NH$_4$OAc (3.20 g, 41.6 mmol) and Et$_3$N (5.7 mL, 42 mmol) were added, and the resulting mixture was stirred at 55° C. for 4 h. Then, the reaction was quenched by the addition of saturated aqueous KH$_2$PO$_4$ solution. Ethyl acetate (100 mL) was added, and the organic layer was washed (water), dried and concentrated. Column chromatography [silica, hexanes/ethyl acetate (3:1)] afforded a light yellow solid (456 mg, 76%): mp 133-134° C.; $^1$H NMR 1.11-1.19 (m, 9H), 1.35 (t, J=7.2 Hz, 3H), 2.12 (s, 3H), 2.34 (q, J=7.2 Hz, 2H), 2.56 (s, 2H), 4.28 (q, J=7.2 Hz, 2H), 6.56 (s, 1H), 7.43 (d, J=3.3 Hz, 1H), 11.86 (bs, 1H); $^{13}$C NMR δ 13.9, 14.8, 15.8, 24.2, 26.2, 42.8, 48.0, 59.8, 106.7, 106.8, 116.0, 119.6, 124.1, 124.2, 146.8, 185.0; ESI-MS obsd 289.1911, calcd 289.1910 [(M+H)$^+$, M=C$_{17}$H$_{24}$N$_2$O$_2$].

5-Ethyl-8-(ethoxycarbonyl)-1-(1,1-dimethoxymethyl)-2,2-dimethyl-2,3-dihydrodipyrrin (6bb)

Following a general procedure,[304] a solution of 5bb (456 mg, 1.58 mmol) in 1,4-dioxane (20 mL) was treated with SeO$_2$ (527 mg, 4.75 mmol). The reaction mixture was stirred at room temperature for 30 min. Ethyl acetate and water were then added, and the organic layer was washed (brine), dried and concentrated. The resulting crude solid was treated directly with HC(OMe)$_3$ (10 mL) and TsOH.H$_2$O (90 mg, 0.475 mmol). After 12 h at room temperature, the reaction mixture was quenched by the addition of saturated aqueous NaHCO$_3$ solution followed by extraction with ethyl acetate. The organic layer was dried (Na$_2$SO$_4$) and concentrated. Column chromatography [silica, hexanes/ethyl acetate (4:1)] afforded a brown solid (347 mg, 63%): mp 124-126° C.; $^1$H NMR δ 1.15 (t, J=7.2 Hz, 3H), 1.29 (s, 6H), 1.35 (t, J=7.2 Hz, 3H), 2.37 (q, J=7.2 Hz, 2H), 2.60 (s, 2H), 3.44 (s, 6H), 4.28 (q, J=7.2 Hz, 2H), 5.11 (s, 1H), 6.62 (s, 1H), 7.46 (dd, J=2.9, 1.5 Hz, 1H), 11.67 (s, 1H); $^{13}$C NMR δ 12.7, 13.8, 14.8, 24.4, 26.5, 44.5, 47.9, 54.5, 59.8, 102.2, 107.8, 116.1, 123.1, 124.9, 133.5, 146.0, 166.6, 179.7; ESI-MS obsd 349.2116 calcd 349.2122 [(M+H)$^+$, M=C$_{19}$H$_{28}$N$_2$O$_4$].

Diethyl 8,8,18,18-tetramethyl-5,15-diethylbacteriochlorin-2,12-dicarboxylate (7bb-HBC)

Following a general procedure,[265] a solution of 6bb (100 mg, 0.29 mmol) in anhydrous CH$_2$Cl$_2$ (15 mL) was treated with 2,6-DTBP (1.10 g, 5.75 mmol) followed by TMSOTf (262 μL, 1.44 mmol). The reaction mixture was stirred at room temperature for 15 h, and then diluted with CH$_2$Cl$_2$ and washed with saturated aqueous NaHCO$_3$. The organic layer was dried (Na$_2$SO$_4$) and concentrated. Column chromatography [silica, hexanes/ethyl acetate (4:1)] afforded a purple solid (29 mg, 35%): $^1$H NMR δ −0.98 (s, 2H), 1.68-1.79 (m, 12H), 1.96 (s, 12H), 4.07 (q, J=7.4 Hz, 4H), 4.24 (s, 4H), 4.77 (q, J=7.0 Hz, 4H), 9.32 (d, J=2.2 Hz, 2H), 9.74 (s, 2H); $^{13}$C NMR δ 15.0, 18.7, 27.4, 31.5, 45.9, 49.5, 61.1, 97.3, 115.8, 122.3, 123.0, 134.2, 134.9, 160.4, 166.2, 171.2; ESI-MS obsd 571.3055, calcd 571.3279 [(M+H)$^+$, M=C$_{34}$H$_{42}$N$_4$O$_4$]; λ$_{abs}$ 361, 383, 548, 753 nm (CH$_2$Cl$_2$).

2,2-Dimethyl-5-(p-tolyl)pent-4-ynoic acid (1c)

A solution of methyl 2,2-dimethylpent-4-ynoate (2.50 g, 17.8 mmol) in Et$_3$N was added to a Schlenk flask and treated with CuI (110 mg, 0.60 mmol), Pd(PPh$_3$)$_4$Cl$_2$ (150 mg, 0.20 mmol) and PPh$_3$ (206 mg, 0.80 mmol). The resulting mixture was deaerated by three freeze-pump-thaw cycles and then kept at 80° C. for 12 h. Upon cooling to rt, 150 mL CH$_2$Cl$_2$ was added and the reaction mixture was filtered through Celite. The filtrate was concentrated to dryness and sequentially treated with KOH (2.35 g, 42.0 mol), water (10 mL), MeOH (10 mL) and THF (30 mL) under argon. After 12 h, 6 M HCl was added until the reaction mixture exhibited pH=1. The organic layer was then extracted with CH$_2$Cl$_2$. The organic extract was dried (Na$_2$SO$_4$) and concentrated. Column chromatography [silica, hexanes/ethyl acetate (2:1)] afforded a white solid (2.73 g, 72%): mp 183-185° C.; $^1$H NMR δ 1.38 (s, 6H), 2.34 (s, 6H), 2.69 (s, 3H), 7.08-7.31 (m, 4H); $^{13}$C NMR δ 21.7, 24.6, 30.5, 42.6, 83.2, 85.7, 120.7, 129.2, 131.7, 138.0, 183.7; ESI-MS obsd 217.1217, calcd 217.1223 [(M+H)$^+$, M=C$_{14}$H$_{16}$O$_2$].

(E)-Ethyl 5-[(4,4-dimethyl-5-oxodihydrofuran-2(3H)-ylidene)(p-tolyl)methyl]-1H-pyrrole-3-carboxylate (3cb)

Following a general procedure,[6] a solution of 1c (1.70 g, 7.87 mmol), 2b (1.05 g, 3.96 mmol) and BnNEt$_3$Cl (894 mg, 3.94 mmol) in dry acetonitrile (20 mL) and Et$_3$N (5 mL) was added to a Schlenk flask and deaerated by three freeze-pump-thaw cycles. A sample of Pd(PPh$_3$)$_4$ (296 mg, 0.296 mmol) was then added, and the resulting mixture was further deaerated. The reaction mixture was kept at 80° C. for 24 h, and then CH$_2$Cl$_2$ and water were added. The organic layer was dried (Na$_2$SO$_4$) and concentrated. Column chromatography [silica, hexanes/ethyl acetate (4:1)] afforded a yellow solid (960 mg, 69%): mp 117-119° C.; $^1$H NMR δ 1.33-1.37 (m, 9H), 2.36 (s, 3H), 3.06 (s, 2H), 4.30 (q, J=7.1 Hz, 2H), 6.56 (dd, J=2.6, 1.5 Hz, 1H), 7.18 (s, 4H), 7.32 (dd, J=3.2, 1.5 Hz, 1H), 8.10 (s, 1H); $^{13}$C NMR δ 14.8, 21.5, 25.4, 40.2, 42.0, 60.1, 109.2, 111.1, 117.5, 123.4, 129.6, 129.8, 129.9, 132.3, 138.0, 145.0, 165.1, 179.8; ESI-MS obsd 354.1696, calcd 354.1700 [(M+H)$^+$, M=C$_{21}$H$_{23}$NO$_4$].

(E)-Ethyl-5-((4,4-dimethyl-5-methylenedihydrofuran-2(3H)-ylidene)(p-tolyl)methyl)-1H-pyrrole-3-carboxylate (4cb)

Following a general procedure,[6] a solution of TiCp$_2$Cl$_2$ (2.99 g, 12.13 mmol) in toluene (30 mL) was treated dropwise with LiMe solution (1.6 M, 17 mL in THF/heptane/ethylbenzene, 27 mmol) at 0° C. under an argon atmosphere, then the resulting solution was stirred at 0° C. After 1 h, saturated aqueous NH$_4$Cl solution was added. The organic layer was washed (water and brine), dried (Na$_2$SO$_4$) and filtered. The filtrate was treated with lactone 3cb (904 mg, 2.56 mmol) and TiCp$_2$Cl$_2$ (39 mg). The resulting solution was heated at 80° C. in the dark for 6 h. Afterwards, the resulting mixture was allowed to cool to room temperature whereupon MeOH (3.1 mL), NaHCO$_3$ (130 mg) and water (31 μL) were added. The resulting solution was kept at 40° C. for another 12 h with stirring and then filtered through Celite. The filtrate was concentrated. Column chromatography [silica, hexanes/ethyl acetate (3:1)] afforded a yellow solid (451 mg, 50%): mp 107-108° C.; $^1$H NMR δ 1.27 (s, 6H), 1.35 (t, J=7.2 Hz, 3H), 2.35 (s, 3H), 2.79 (s, 2H), 4.00 (d, J=2.2 Hz, 1H), 4.29 (q, J=7.2 Hz, 2H), 4.35 (d, J=2.2 Hz, 1H), 6.48 (dd, J=2.6, 1.5 Hz, 1H), 7.14-7.24 (m, 4H), 7.36 (dd, J=3, 1.5 Hz, 1H), 8.04 (s, 1H); $^{13}$C NMR δ 14.7, 21.5, 27.8, 40.1, 44.2, 60.0, 81.4, 105.8, 108.5, 117.1, 122.7, 129.3, 129.8, 131.9, 133.8, 136.9, 151.8, 165.3, 170.0; ESI-MS obsd 352.1914, calcd 352.1907 [(M+H)$^+$, M=C$_{22}$H$_{25}$NO$_3$].

5-p-Tolyl-8-(ethoxycarbonyl)-1-methyl-2,2-dimethyl-2,3-dihydrodipyrrin (5cb)

Following a general procedure,[6] a solution of 4cb (451 mg, 1.28 mmol) in DMF (20 mL) was treated with 1M HCl (1.0 mL). After 30 min, NH$_4$OAc (1.97 g, 25.6 mmol) and Et$_3$N (3.5 mL, 26 mmol) were added and the mixture was stirred at 55° C. for 4 h. Then, the reaction was quenched by the addition of saturated aqueous KH$_2$PO$_4$ solution. Ethyl acetate (100 mL) was added and the organic layer was washed (water), dried and concentrated. Column chromatography [silica, hexanes/ethyl acetate (3:1)] afforded a light yellow solid (247 mg, 55%): mp 114-116° C.; $^1$H NMR δ 1.13 (s, 6H), 1.28 (t, J=7.2 Hz, 3H), 2.17 (s, 3H), 2.37 (s, 2H), 2.40 (s, 3H), 4.22 (q, J=7.2 Hz, 2H), 6.02 (t, J=1.9 Hz, 1H), 7.16-7.19 (m, 4H), 7.48 (dd, J=3.0, 1.7 Hz, 1H), 11.85 (s, 1H); $^{13}$C NMR δ 14.8, 15.9, 21.5, 25.9, 44.1, 48.2, 59.7, 76.9, 77.3, 77.8, 109.6, 116.1, 120.4, 124.4, 129.3, 129.8, 135.0, 136.2, 137.0, 148.1, 165.6, 186.9; ESI-MS obsd 351.2076, calcd 351.2067 [(M+H)$^+$, M=C$_{22}$H$_{26}$N$_2$O$_2$].

5-p-Tolyl-8-(ethoxycarbonyl)-1-(1,1-dimethoxymethyl)-2,2-dimethyl-2,3-dihydrodipyrrin (6cb)

Following a general procedure,[304] a solution of 5cb (247 mg, 0.706 mmol) in 1,4-dioxane (15 mL) was treated with SeO$_2$ (235 mg, 2.12 mmol). The reaction mixture was stirred at room temperature for 30 min. Ethyl acetate and water were then added, and the organic layer was washed (brine), dried and concentrated. The resulting crude solid was treated directly with HC(OMe)$_3$ (10 mL) and TsOH·H$_2$O (80 mg, 0.21 mmol). After 12 h, the reaction mixture was quenched by the addition of saturated aqueous NaHCO$_3$ solution followed by extraction with ethyl acetate. The organic layer was dried (Na$_2$SO$_4$) and concentrated. Column chromatography [silica, hexanes/ethyl acetate (2:1)] afforded a brown oil (122 mg, 43%): $^1$H NMR δ 1.22 (s, 6H), 1.28 (t, J=7.2 Hz, 3H), 2.40 (s, 2H), 3.48 (s, 6H), 4.22 (q, J=7.2 Hz, 2H), 5.11 (s, 1H), 6.07 (s, 1H), 7.15-7.23 (m, 4H), 7.50 (dd, J=2.9, 1.7 Hz, 1H), 11.65 (s, 1H); $^{13}$C NMR δ 14.7, 21.5, 26.2, 45.8, 48.0, 54.6, 59.8, 102.2, 110.7, 116.3, 123.6, 125.1, 129.3, 129.5, 134.6, 135.8, 137.3, 147.2, 165.5, 181.4; ESI-MS obsd 411.2268, calcd 411.2278 [(M+H)$^+$, M=C$_{24}$H$_{30}$N$_2$O$_4$].

Diethyl 8,8,18,18-tetramethyl-5,15-di-p-tolylbacteriochlorin-2,12-dicarboxylate) (7cb-HBC)

Following a general procedure,[265] a solution of 6cb (122 mg, 0.30 mmol) in anhydrous CH$_2$Cl$_2$ (15 mL) was treated with 2,6-DTBP (1.14 g, 5.95 mmol) followed by TMSOTf (270 µL, 1.50 mmol). The reaction mixture was stirred at room temperature for 15 h, diluted with CH$_2$Cl$_2$ and washed with saturated aqueous NaHCO$_3$. The organic layer was dried (Na$_2$SO$_4$) and concentrated. Column chromatography [silica, hexanes/ethyl acetate (4:1)] gave two bands (both purple). The first band was isolated and concentrated to afford the title compound 7cb-HBC as a dark purple solid (39 mg, 38%). The second band afforded bacteriochlorin 7cb-MeOBc as a dark purple solid (9.8 mg, 9.1%). Data for the title compound: $^1$H NMR δ −0.99 (s, 2H), 1.62 (t, J=7.2 Hz, 6H), 1.88 (s, 12H), 2.65 (s, 6H), 3.96 (s, 6H), 4.68 (q, J=7.2 Hz, 4H), 7.51 (d, J=7.7 Hz, 4H), 7.72 (d, J=7.7 Hz, 4H), 8.65 (s, 2H), 9.77 (s, 2H); $^{13}$C NMR δ 15.0, 21.8, 31.3, 46.1, 51.3, 61.0, 98.1, 115.9, 122.2, 126.0, 129.0, 132.2, 135.0, 135.7, 137.5, 139.1, 160.7, 166.0, 172.5; ESI-MS obsd 694.3514, calcd 694.3514 [(M)$^+$, M=C$_{44}$H$_{46}$N$_4$O$_4$]; λ$_{abs}$ 360, 371, 382, 542, 759 nm (CH$_2$Cl$_2$).

Data for diethyl 10-methoxy-8,8,18,18-tetramethyl-5,15-di-p-tolylbacteriochlorin-2,12-dicarboxylate (7cb-MeOBC): $^1$H NMR δ −0.91 (s, 1H), −0.81 (s, 1H), 1.49-1.62 (m, 6H), 1.84 (s, 6H), 1.96 (s, 6H), 2.61 (s, 4H), 2.63 (s, 4H), 3.86 (s, 3H), 3.88 (s, 3H), 4.04 (s, 3H), 4.57-4.88 (m, 4H), 7.45-7.69 (m, 8H), 8.09 (d, J=2.2 Hz, 1H), 8.56 (d, J=2.2 Hz, 1H), 9.55 (s, 1H); $^{13}$C NMR δ 14.5, 14.9, 21.7, 29.3, 30.9, 46.1, 47.1, 50.9, 61.0, 61.9, 68.0, 96.8, 115.3, 116.2, 122.0, 125.0, 126.9, 128.9, 129.7, 131.9, 132.1, 134.2, 135.3, 136.5, 137.4, 137.5, 137.9, 139.1, 139.4, 159.2, 159.7, 165.8, 168.4, 173.1; ESI-MS obsd 752.3692, calcd 752.3697 [(M+H)$^+$, M=C$_{45}$H$_{48}$N$_4$O$_5$]; λ$_{abs}$ 379, 548, 748 nm (CH$_2$Cl$_2$).

tert-Butyl 1H-pyrrole-2-carboxylate (9)

A solution of 1H-pyrrole-2-carboxylic acid (5.00 g, 45.0 mmol) in THF (120 mL) was treated with tert-BuOH (60 mL) followed by DCC (13.9 g, 67.6 mmol) at 0° C. under an argon atmosphere. After 1 h, the reaction mixture was filtered. The filtrate was concentrated and chromatographed [silica, hexanes/ethyl acetate (10:1)] to afford a white solid (3.76 g, 50%): mp 91-93° C.; $^1$H NMR δ 1.47 (s, 9H), 6.22-6.25 (m, 1H), 6.82-6.85 (m, 1H), 6.90-6.92 (m, 1H), 9.23 (bs, 1H); $^{13}$C NMR δ 28.6, 81.0, 110.4, 112.4, 114.8, 160.9; ESI-MS obsd 168.1017, calcd 168.1019 [(M+H)$^+$, M=C$_9$H$_{13}$NO$_2$].

tert-Butyl 5-bromo-1H-pyrrole-2-carboxylate (2c)

Following a procedure for the preparation of a similar compound,[8] a solution of tert-butyl 1H-pyrrole-2-carboxylate (670 mg, 4.0 mmol) in THF (40 mL) and MeOH (20 mL) was treated with NBS (89 mg, 0.50 mmol) at 0° C. After 30 min, another portion of NBS (89 mg, 0.50 mmol) was added. After 30 min, another portion of NBS (89 mg, 0.50 mol) was added. After 30 min, another portion of NBS (89 mg, 0.50 mmol) was added. After 30 min, the last portion of NBS (178 mg, 1.0 mol) was added. After 30 min, the last portion of NBS (178 mg, 1.0 mol) was added. After 2 h, the reaction solution was concentrated. Column chromatography [silica, hexanes/diethyl ether (20:1)] afforded a white solid (396 mg, 40%): mp 95-96° C.; $^1$H NMR δ 1.21 (s, 9H), 6.22 (dd, J=3.0, 3.2 Hz, 1H), 6.73 (dd, J=3.0, 3.2 Hz, 1H), 9.37 (bs, 1H); $^{13}$C NMR δ 28.6, 81.7, 104.2, 112.7, 116.4, 125.8, 159.8; ESI-MS obsd 246.0117, calcd 246.0125 [(M+H)$^+$, M=C$_9$H$_{12}$BrNO$_2$].

tert-Butyl (E)-5-((4,4-dimethyl-5-oxodihydrofuran-2(3H)-ylidene)(p-tolyl)methyl)-1H-pyrrole-2-carboxylate (3cc)

Following a general procedure,[6] a solution of 1c (645 mg, 3.00 mmol), 2c (493 mg, 2.00 mmol) and BnNEt$_3$Cl (456 mg, 2.00 mmol) in dry acetonitrile (15 mL) and Et$_3$N (5 mL) was added to a Schlenk flask and deaerated by three freeze-pump-thaw cycles. A sample of Pd(PPh$_3$)$_4$ (150 mg, 0.130 mmol) was then added and the resulting mixture was further deaerated. The reaction mixture was kept at 80° C. for 24 h, and then CH$_2$Cl$_2$ and water were added. The organic layer was dried (Na$_2$SO$_4$) and concentrated. Column chromatography [silica, hexanes/ethyl acetate (4:1)] afforded a yellow solid (426 mg, 56%): mp 117-119° C.; $^1$H NMR δ 1.37 (s, 6H), 1.52 (s, 9H), 2.37 (s, 3H), 3.03 (s, 2H), 6.14-6.17 (m, 1H), 6.82-6.84 (m, 1H), 8.52 (s, 1H); $^{13}$C NMR δ 21.5, 25.1, 25.3, 28.5, 28.6, 40.2, 42.0, 81.1, 110.4, 111.7, 115.4, 124.2, 128.3, 129.4, 129.58, 129.65, 132.2, 133.4, 138.0, 145.7, 160.8, 179.7; ESI-MS obsd 404.1824, calcd 404.1832 [(M+Na)$^+$, M=C$_{23}$H$_{27}$NO$_4$].

tert-Butyl (E)-5-((4,4-dimethyl-5-methylenedihydrofuran-2(3H)-ylidene)(p-tolyl)methyl)-1H-pyrrole-2-carboxylate (4cc)

Following a general procedure,[6] a solution of TiCp$_2$Cl$_2$ (1.23 g, 4.93 mmol) in toluene (15 mL) was treated dropwise with LiMe solution (1.6 M, 17 mL in THF/heptane/ethylbenzene, 27 mmol) at 0° C. under an argon atmosphere, then the resulting solution was stirred at 0° C. After 1 h, saturated aqueous NH$_4$Cl solution was added. The organic layer was washed (water and brine), dried (Na$_2$SO$_4$) and filtered. The filtrate was treated with lactone 3cc (396 mg, 1.04 mmol) and TiCp$_2$Cl$_2$ (18 mg). The resulting solution was heated to 80° C. in the dark for 6 h. Afterwards, the resulting mixture was allowed to cool to room temperature whereupon MeOH (1.5 mL), NaHCO$_3$ (60 mg) and water (15 µL) were added. The resulting solution was kept at 40° C. for another 12 h and then filtered through Celite. The filtrate was concentrated. Column chromatography [silica, hexanes/ethyl acetate (3:1)] afforded a yellow solid (228 mg, 58%): mp 93-95° C.; $^1$H NMR δ 1.28 (s, 6H), 1.53 (s, 9H), 2.37 (s, 3H), 2.79 (s, 2H), 2.77 (s, 2H), 4.00 (d, J=2.1 Hz, 1H), 4.37 (d, J=2.1 Hz, 1H), 6.08 (t, J=2.9 Hz, 1H), 6.82 (t, J=2.9 Hz, 1H), 7.15-7.26 (m, 4H), 8.43 (s, 1H); $^{13}$C NMR δ 21.5, 27.8, 28.6, 40.2, 44.2, 80.8, 81.6, 106.5, 109.8, 115.4, 123.3, 129.4, 129.8, 133.6, 135.7, 137.0, 152.3, 160.9, 169.8; ESI-MS obsd 757.4195, calcd 757.4211 [(2M−H)$^+$, M=C$_{24}$H$_{29}$NO$_3$].

5-p-Tolyl-9-(tert-butoxycarbonyl)-1-methyl-2,2-dimethyl-2,3-dihydrodipyrrin (5cc)

Following a general procedure,[6] a solution of 4cc (228 mg, 0.602 mmol) in DMF (20 mL) was treated with 1M HCl (1.0 mL). After 30 min, NH$_4$OAc (1.62 g, 21.2 mmol) and Et$_3$N (2.9 mL, 21 mmol) were added and the mixture was stirred at 55° C. for 4 h. Then, the reaction was quenched by the addition of saturated aqueous KH$_2$PO$_4$ solution. Ethyl acetate (100 mL) was added and the organic layer was washed (water), dried and concentrated. Column chromatography [silica, hexanes/ethyl acetate (3:1)] afforded a white solid (150 mg, 66%): mp 114-116° C.; $^1$H NMR δ 1.13 (s, 6H), 1.58 (s, 9H), 2.19 (s, 3H), 2.38 (s, 5H), 5.63 (dd, J=1.2, 2.4 Hz, 1H), 6.71 (dd, J=1.2, 2.4 Hz, 1H), 7.14-7.21 (m, 4H), 12.0 (s, 1H); $^{13}$C NMR δ 16.1, 21.5, 25.9, 28.7, 44.3, 48.3, 80.3, 110.8, 114.8, 120.2, 124.5, 129.3, 129.8, 136.1, 137.0, 137.4, 149.9, 160.9, 188.0; ESI-MS obsd 379.2381, calcd 379.2380 [(M+H)$^+$, M=C$_{24}$H$_{30}$N$_2$O$_2$].

5-p-Tolyl-9-(tert-butoxycarbonyl)-1-(1,1-dimethoxymethyl)-2,2-dimethyl-2,3-dihydrodipyrrin (6cc)

Following a general procedure,[304] a solution of 5cc (150 mg, 0.396 mmol) in 1,4-dioxane (10 mL) was treated with SeO$_2$ (132 mg, 1.19 mmol). The reaction mixture was stirred at room temperature for 30 min. Ethyl acetate and water were then added, and the organic layer was washed (brine), dried and concentrated. The resulting crude solid was treated directly with HC(OMe)$_3$ (5 mL) and TsOH.H$_2$O (23 mg, 0.12 mmol). After 12 h, the reaction mixture was quenched by the addition of saturated aqueous NaHCO$_3$ solution followed by extraction with ethyl acetate. The organic layer was dried (Na$_2$SO$_4$) and concentrated. Column chromatography [silica, hexanes/ethyl acetate (2:1)] afforded a brown solid (82 mg, 47%): mp 123-125° C.; $^1$H NMR δ 1.23 (s, 6H), 1.59 (s, 9H), 2.39 (s, 3H), 2.41 (s, 2H), 3.50 (s, 6H), 5.16 (s, 1H), 5.67-5.69 (m, 1H), 6.71-6.74 (m, 1H), 7.14-7.21 (m, 4H), 11.70 (s, 1H); $^{13}$C NMR δ 21.5, 26.3, 28.7, 46.1, 48.2, 54.9, 80.4, 103.1, 111.8, 114.9, 123.3, 125.2, 129.3, 129.6, 135.9, 136.8, 137.3, 149.0, 160.7, 182.3; ESI-MS obsd 439.2607, calcd 439.2591 [(M+H)$^+$, M=C$_{26}$H$_{34}$N$_2$O$_4$].

tert-Butyl (E)-5-((4,4-dimethyl-5-oxodihydrofuran-2(3H)-ylidene)methyl)-1H-pyrrole-2-carboxylate (3ac)

Following a general procedure,[6] a solution of 1a (1.25 g, 9.90 mmol), 2c (975 mg, 3.96 mmol) and BnNEt$_3$Cl (903 mg, 3.96 mmol) in dry acetonitrile (21 mL) and Et$_3$N (7 mL) was added to a Schlenk flask and deaerated by three freeze-pump-thaw cycles. A sample of Pd(PPh$_3$)$_4$ (309 mg, 0.258 mmol) was then added and the resulting mixture was further deaerated. The reaction mixture was kept at 80° C. for 24 h, and then CH$_2$Cl$_2$ and water were added. The organic layer was dried (Na$_2$SO$_4$) and concentrated. Column chromatography [silica, hexanes/ethyl acetate (4:1)] afforded a yellow solid (711 mg, 62%): mp 96-98° C.; $^1$H NMR δ 1.35 (s, 6H), 1.58 (s, 9H), 2.95 (s, 2H), 6.03-6.06 (m, 1H), 6.31-6.32 (m, 1H), 6.83-6.85 (m, 1H), 9.73 (s, 1H); $^{13}$C NMR δ 25.6, 28.6, 40.1, 40.8, 81.4, 98.3, 108.4, 116.5, 123.9, 131.4, 149.6, 161.2, 179.8; ESI-MS obsd 314.1350, calcd 314.1363 [(M+Na)$^+$, M=C$_{16}$H$_{21}$NO$_4$].

tert-Butyl (E)-5-((4,4-dimethyl-5-methylenedihydrofuran-2(3H)-ylidene)methyl)-1H-pyrrole-2-carboxylate (4ac)

Following a general procedure,[6] a solution of TiCp$_2$Cl$_2$ (1.90 g, 7.60 mmol) in toluene (21 mL) was treated dropwise with LiMe solution (1.6 M, 11 mL in THF/heptane/ethylbenzene, 18 mmol) at 0° C. under an argon atmosphere, then the resulting solution was stirred at 0° C. After 1 h, saturated aqueous NH$_4$Cl solution was added. The organic layer was washed (water and brine), dried (Na$_2$SO$_4$) and filtered. The filtrate was treated with lactone 3ac (474 mg, 1.62 mmol) and TiCp$_2$Cl$_2$ (24 mg). The resulting solution was heated to 80° C. in the dark for 6 h. Afterwards, the resulting mixture was allowed to cool to room temperature whereupon MeOH (2.0 mL), NaHCO$_3$ (81 mg) and water (20 µL) were added. The resulting solution was kept at 40° C. for another 12 h and then filtered through Celite. The filtrate was concentrated. Column chromatography [silica, hexanes/ethyl acetate (4:1)] afforded a yellow solid (189 mg, 40%): mp 90-92° C.; $^1$H NMR δ 1.26 (s, 6H), 1.57 (s, 9H), 2.72 (s, 2H), 4.03 (d, J=2.1 Hz, 1H), 4.41 (d, J=2.1 Hz, 1H), 5.91 (s, 1H), 3.97 (t, J=2.8 Hz, 1H), 6.81 (t, J=2.8 Hz, 1H), 8.82 (s, 1H); $^{13}$C NMR δ 25.5, 28.6, 40.1, 40.8, 81.3, 98.3, 108.4, 116.4, 123.9, 131.4, 149.6, 161.2, 179.8; ESI-MS obsd 290.1752, calcd 290.1755 [(M+H)$^+$, M=C$_{17}$H$_{23}$NO$_3$].

9-(tert-Butoxycarbonyl)-1-methyl-2,2-dimethyl-2,3-dihydrodipyrrin (5ac)

Following a general procedure,[6] a solution of 4ac (181 mg, 0.626 mmol) in DMF (20 mL) was treated with 1M HCl (1.0 mL). After 30 min, NH$_4$OAc (0.957 g, 12.5 mmol) and Et$_3$N (1.7 mL, 13 mmol) were added and the mixture was stirred at 55° C. for 4 h. Then, the reaction was quenched by the addition of saturated aqueous KH$_2$PO$_4$ solution. Ethyl acetate (100 mL) was added and the organic layer was washed (water), dried and concentrated. Column chromatography [silica, hexanes/ethyl acetate (3:1)] afforded a white solid (112 mg, 62%): mp 90-91° C.; $^1$H NMR δ 1.25 (s, 6H), 1.55 (s, 9H), 2.14 (s, 3H), 2.55 (s, 2H), 5.80 (s, 1H), 6.01-6.02 (m, 1H), 6.75-6.77 (m, 1H), 11.3 (s, 1H); $^{13}$C NMR δ 16.0, 23.8, 29.5, 44.7, 49.5, 80.2, 105.8, 109.7, 115.1, 124.3, 135.0, 152.2, 160.4, 188.8; ESI-MS obsd 289.1905, calcd 289.1910 [(M+H)$^+$, M=C$_{17}$H$_{24}$N$_2$O$_2$].

(E)-5-((4,4-Dimethyl-5-methylenedihydrofuran-2 (3H)-ylidene)methyl)-1H-pyrrole (4ac')

Compound 3ac (401 mg, 1.38 mmol) was treated with TFA (5 mL) in CH$_2$Cl$_2$ (5 mL) at room temperature for 2 h. Aqueous saturated NaHCO$_3$ solution (100 mL) was added and the resulting mixture was extracted with CH$_2$Cl$_2$ (100 mL). The organic layer was dried (Na$_2$SO$_4$) and concentrated. The resulting crude decarboxylated compound was directly treated with Petasis reagent prepared from TiCp$_2$Cl$_2$ (1.90 g, 7.60 mmol) and LiMe solution (1.6 M, 11 mL in THF/heptane/ethylbenzene, 18 mmol) in toluene (21 mL) following the general procedure as described previously. The resulting solution was heated to 80° C. in the dark for 6 h. Afterwards, the resulting mixture was allowed to cool to room temperature whereupon MeOH (2.0 mL), NaHCO$_3$ (81 mg) and water (20 μL) were added. The resulting solution was kept at 40° C. for another 12 h and then filtered through Celite. The filtrate was concentrated. Column chromatography [silica, hexanes/ethyl acetate (10:1)] afforded a yellow solid (112 mg, 43%): mp 75-77° C.; $^1$H NMR δ 1.28 (s, 6H), 1.53 (s, 9H), 2.37 (s, 3H), 2.79 (s, 2H), 2.77 (s, 2H), 4.02 (d, J=2.4 Hz, 1H), 4.40 (d, J=2.4 Hz, 1H), 5.93 (d, J=1.8 Hz, 1H), 5.99 (s, 1H), 6.25 (dd, J=2.7 Hz, 1H), 6.72-6.75 (m, 1H), 7.96 (s, 1H); $^{13}$C NMR δ 28.2, 40.4, 42.6, 80.5, 93.5, 105.4, 109.8, 117.0, 128.6, 153.2, 169.8; ESI-MS obsd 190.1222, calcd 190.1226 [(M+H)$^+$, M=C$_{12}$H$_{15}$NO].

1-Methyl-2,2-dimethyl-2,3-dihydrodipyrrin (5ac-DC)

Following a general procedure,[6] a solution of 4ac' (107 mg, 0.566 mmol) in DMF (20 mL) was treated with 1M HCl (0.2 mL, acid dose reduced due to substrate stability). After 30 min, NH$_4$OAc (0.87 g, 11.3 mmol) and Et$_3$N (1.6 mL, 12 mmol) were added and the mixture was stirred at 55° C. for 4 h. Then, the reaction was quenched by the addition of saturated aqueous KH$_2$PO$_4$ solution. Ethyl acetate (100 mL) was added and the organic layer was washed (water), dried and concentrated. Column chromatography [silica, hexanes/ethyl acetate (10:1)] afforded a yellow solid (77 mg, 72%): mp 82-84° C.; $^1$H NMR δ 1.17 (s, 6H), 2.12 (s, 3H), 2.55 (s, 2H), 5.86 (s, 1H), 6.05 (s, 1H), 6.14 (q, J=3.0 Hz, 1H), 6.81 (d, J=1.5 Hz, 1H), 10.8 (s, 1H); $^{13}$C NMR δ 15.8, 25.8, 44.3, 48.4, 106.5, 107.9, 108.4, 118.7, 131.3, 148.4, 186.1; ESI-MS obsd 189.1384, calcd 189.1386 [(M+H)$^+$, M=C$_{12}$H$_{16}$N$_2$].

8,8,18,18-Tetramethylbacteriochlorin (7ac-HBC)

Compound 5ac-DC (53 mg, 0.28 mmol) in CH$_2$Cl$_2$ (15 mL) was treated with SeO$_2$ (67 mg, 0.60 mmol) under argon under room temperature. After TLC analysis showed the disappearance the 5ac-DC, TMSOTf (282 μL, 1.55 mmol) and 2,6-DTBP (1.18 g, 6.16 mmol) was added immediately to the reaction mixture. The reaction mixture was stirred at room temperature for 3 h, and then diluted with CH$_2$Cl$_2$ and washed with saturated aqueous NaHCO$_3$. The organic layer was dried (Na$_2$SO$_4$) and concentrated. Column chromatography [silica, hexanes/ethyl acetate (10:1)] afforded a dark green solid (3.0 mg, 5.8%): $^1$H NMR δ −2.38 (s, 2H), 1.97 (s, 12H), 4.46 (s, 4H), 7.24 (d, J=1.2 Jz, 2H), 8.71-8.77 (m, 2H), 8.83 (s, 2H); $^{13}$C NMR δ 29.9, 31.3, 46.2, 51.7, 96.7, 98.9, 121.9, 122.1, 135.5, 136.4, 157.8, 169.8; ESI-MS obsd 371.2224, calcd 371.2230 [(M+H)$^+$, M=C$_{24}$H$_{26}$N$_4$]; $\lambda_{abs}$ 339, 364, 488, 713 nm (CH$_2$Cl$_2$).

tert-Butyl (E)-4-bromo-5-((4,4-dimethyl-5-oxodihydrofuran-2(3H)-ylidene)methyl)-1H-pyrrole-2-carboxylate (3ac-Br)

A solution of 3ac (470 mg, 1.62 mmol) in THF (15 mL) was treated with NBS (287 mg, 1.62 mmol) at −78° C. for 15 min. Water and CH$_2$Cl$_2$ were added. The organic layer was separated, dried (Na$_2$SO$_4$) and concentrated. Column chromatography [silica, hexanes/ethyl acetate (4:1)] afforded a white solid (492 mg, 82%): mp 102-104° C.; $^1$H NMR δ 1.36 (s, 6H), 1.56 (s, 9H), 2.95 (d, J=2.4 Hz, 2H), 6.23 (t, J=2.4 Hz, 1H), 6.81 (d, J=2.7 Hz, 1H), 8.91 (s, 1H); $^{13}$C NMR δ 25.4, 28.5, 40.2, 40.6, 82.1, 96.5, 99.3, 117.4, 124.5, 128.7, 150.1, 160.2, 179.1; ESI-MS obsd 370.0650, calcd 370.0649 [(M+H)$^+$, M=C$_{16}$H$_{20}$BrNO$_4$].

tert-Butyl (E)-4-phenyl-5-((4,4-dimethyl-5-oxodihydrofuran-2(3H)-ylidene)methyl)-1H-pyrrole-2-carboxylate (3ac-Ph)

A solution of 3ac-Br (490 mg, 1.32 mmol), K$_2$CO$_3$ (550 mg, 3.96 mmol), Pd(PPh$_3$)$_4$ (76 mg, 0.066 mmol) and phenylboronic acid (323 mg, 2.64 mmol) in toluene (20 mL) was added to a Schlenk flask and deaerated by three freeze-pump-thaw cycles. The reaction mixture was kept at 80° C. for 16 h. Water and CH$_2$Cl$_2$ were added. The organic layer was separated, dried (Na$_2$SO$_4$) and concentrated. Column chromatography [silica, hexanes/ethyl acetate (5:1)] afforded a white solid (434 mg, 90%): mp 113-115° C.; $^1$H NMR δ 1.26 (s, 6H), 1.56 (s, 9H), 2.71 (d, J=2.1 Hz, 2H), 6.34 (s, 1H), 6.94 (d, J=2.7 Hz, 1H), 7.37-7.41 (m, 5H), 8.98 (s, 1H); $^{13}$C NMR δ 25.3, 28.6, 40.2, 40.4, 81.6, 97.7, 115.3, 124.1, 126.2, 126.8, 128.3, 128.9, 135.4, 149.9, 161.1, 179.4; ESI-MS obsd 368.1862, calcd 368.1856 [(M+H)$^+$, M=C$_{22}$H$_{25}$NO$_4$].

(E)-5-((4,4-Dimethyl-5-methylenedihydrofuran-2 (3H)-ylidene)(p-tolyl)methyl)-1H-pyrrole (4cc-DC)

Compound 3cc (608 mg, 1.60 mmol) was treated with TFA (5 mL) in CH$_2$Cl$_2$ (5 mL) at room temperature for 2 h. Aqueous saturated NaHCO$_3$ solution (100 mL) was added and the resulting mixture was extracted with CH$_2$Cl$_2$ (100 mL). The organic layer was dried (Na$_2$SO$_4$) and concentrated. The resulting crude decarboxylated compound was directly treated with Petasis reagent prepared from TiCp$_2$Cl$_2$ (1.81 g, 7.24 mmol) and LiMe solution (1.6 M, 11 mL in THF/heptane/ethylbenzene, 18 mmol) in toluene (21 mL) following the general procedure.[6] The resulting solution was heated to 80° C. in the dark for 6 h. Afterwards, the resulting mixture was allowed to cool to room temperature whereupon MeOH (1.6 mL), NaHCO$_3$ (65 mg) and water (1.6 μL) were added. The resulting solution was kept at 40° C. for another 12 h and then filtered through Celite. The filtrate was concentrated. The compound was directly applied to the next step without purification or further characterization due to stability issues.

5-p-Tolyl-1-methyl-2,2-dimethyl-2,3-dihydrodipyrrin (5cc-DC)

Following a general procedure,[6] a solution of 4cc-DC (unpurified, prepared from 608 mg of 3cc) in DMF (20 mL) was treated with 1M HCl (1.0 mL). After 30 min, NH$_4$OAc (1.47 g, 19.2 mmol) and Et$_3$N (2.6 mL, 19 mmol) were added and the mixture was stirred at 55° C. for 4 h. Then, the reaction was quenched by the addition of saturated aqueous KH$_2$PO$_4$ solution. Ethyl acetate (100 mL) was added and the organic layer was washed (water), dried and concentrated. Column chromatography [silica, hexanes/ethyl acetate (3:1)] afforded a white solid (57 mg, 12% overall from 3cc): mp 103-105° C.; $^1$H NMR δ 1.11 (s, 6H), 2.15 (s, 3H), 2.35 (s, 2H), 2.38 (s, 3H), 5.61-5.64 (m, 1H), 6.06-6.09 (m, 1H), 6.86-6.88 (m, 1H), 7.16-7.22 (m, 4H), 11.4 (s, 1H); $^{13}$C NMR δ 15.8, 21.5, 25.9, 44.2, 48.1, 108.1, 109.2, 118.9, 121.2, 129.1, 129.9, 134.1, 136.4, 137.1, 146.3, 185.5; ESI-MS obsd 279.1855, calcd 279.1856 [(M+H)$^+$, M=C$_{19}$H$_{22}$N$_2$].

Ethyl 5-[(4,4-dimethyl-5-methylenedihydrofuran-2(3H)-ylidene)(p-tolyl)methyl]-4-ethyl-1H-pyrrole-3-carboxylate (3ca)

Following a general procedure,[6] a solution of 1c (1.12 g, 5.19 mmol), 2a (760 mg, 2.59 mmol) and BnNEt$_3$Cl (590 mg, 2.59 mmol) in dry DMF (12 mL) and Et$_3$N (3 mL) was added to a Schlenk flask and deaerated by three freeze-pump-thaw cycles. A sample of Pd(PPh$_3$)$_4$ (194 mg, 0.168 mmol) was then added, and the resulting mixture was further deaerated. The reaction mixture was kept at 100° C. for 24 h, and then CH$_2$Cl$_2$ and water were added. The organic layer was dried (Na$_2$SO$_4$) and concentrated. Column chromatography [silica, hexanes/ethyl acetate (2:1)] afforded a clear white solid (405 mg, 41%): mp 131-133° C.; $^1$H NMR δ 1.09 (t, J=7.2 Hz, 3H), 1.31-1.36 (m, 9H), 2.31 (s, 3H), 2.56 (q, J=7.2 Hz, 2H), 2.66 (s, 2H), 4.27 (q, J=6.9 Hz, 2H), 7.07-7.31 (m, 4H), 7.40 (d, J=3.3 Hz, 1H), 8.16 (s, 1H); $^{13}$C NMR δ 14.7, 15.6, 18.9, 21.4, 25.0, 39.7, 41.9, 59.8, 109.3, 114.9, 124.8, 126.0, 126.4, 128.7, 129.1, 133.4, 137.3, 147.2, 165.4, 180.2; ESI-MS obsd 382.2005, calcd 382.2013 [(M+H)$^+$, M=C$_{23}$H$_{27}$NO$_4$].

Ethyl 5-[(4,4-dimethyl-5-methylenedihydrofuran-2(3H)-ylidene)(p-tolyl)methyl]-4-ethyl-1H-pyrrole-3-carboxylate (4ca)

Following a standard procedure,[6] a solution of TiCp$_2$Cl$_2$ (1.16 g, 4.74 mmol) in toluene (13 mL) was treated dropwise with LiMe solution (1.6 M, 7 mL in Et$_2$O, 11 mmol) at 0° C. under an argon atmosphere. After 1 h at 0° C., saturated aqueous NH$_4$Cl solution was added. The organic layer was washed (water and brine), dried (Na$_2$SO$_4$) and filtered. The filtrate was treated with lactone 3ca (380 mg, 1.00 mmol) and TiCp$_2$Cl$_2$ (15 mg). The solution was heated to 80° C. in the dark for 6 h under argon. Afterwards, the resulting mixture was allowed to cool to room temperature whereupon MeOH (1.2 mL), NaHCO$_3$ (50 mg) and water (12 μL) were added. The mixture was kept at 40° C. for another 12 h with stirring and then filtered through Celite. The filtrate was concentrated. Column chromatography [silica, hexanes/ethyl acetate (4:1)] afforded a yellow solid (212 mg, 56%): mp 123-125° C.; $^1$H NMR δ 1.09 (t, J=7.2 Hz, 3H), 1.22 (s, 6H), 1.35 (t, J=6.9 Hz, 3H), 2.31 (s, 3H), 2.43 (s, 2H), 2.60 (q, J=7.2 Hz, 2H), 4.06 (d, J=2.1 Hz, 1H), 4.26 (q, J=6.9 Hz, 2H), 4.50 (d, J=2.1 Hz, 1H), 7.07-7.30 (m, 4H), 7.39 (d, J=3.3 Hz, 1H), 7.90 (s, 1H); $^{13}$C NMR δ 14.7, 15.6, 18.8, 21.3, 27.5, 39.4, 44.4, 59.6, 81.9, 103.5, 114.7, 124.0, 125.9, 128.1, 128.2, 129.0, 134.8, 135.9, 154.1, 165.5, 170.6; ESI-MS obsd 380.2214, calcd 380.2220 [(M+H)$^+$, M=C$_{24}$H$_{29}$NO$_3$].

7-Ethyl-8-(ethoxycarbonyl)-6-p-tolyl-1-methyl-2,2-dimethyl-2,3-dihydrodipyrrin (5ca)

Following a general procedure,[6] a solution of 4ca (135 mg, 0.356 mmol) in DMF (10 mL) was treated with 1M HCl (0.5 mL). After 30 min, NH$_4$OAc (546 mg, 7.12 mmol) and Et$_3$N (1.0 mL, ~7.2 mmol) were added, and the resulting mixture was stirred at 55° C. for 4 h. Then, the reaction was quenched by the addition of saturated aqueous KH$_2$PO$_4$ solution. Ethyl acetate (100 mL) was added, and the organic layer was washed (water), dried and concentrated. Column chromatography [silica, hexanes/ethyl acetate (4:1)] afforded a light yellow solid (97 mg, 72%): mp 115-116° C.; $^1$H NMR δ 0.74 (t, J=7.2 Hz, 3H), 1.11 (s, 6H), 1.29 (t, J=6.9 Hz, 3H), 2.00 (q, J=6.9 Hz, 2H), 2.14 (s, 3H), 2.29 (s, 2H), 2.39 (s, 3H), 4.21 (q, J=7.2 Hz, 2H), 7.12-7.16 (m, 4H), 7.46 (d, J=3.3 Hz, 1H), 11.61 (bs, 1H); $^{13}$C NMR δ 14.7, 15.9, 16.5, 17.8, 21.5, 25.9, 44.5, 47.9, 59.2, 114.5, 121.2, 124.8, 127.2, 129.1, 129.3, 129.6, 136.9, 137.1, 148.7, 165.6, 186.6; ESI-MS obsd 379.2380, calcd 379.2380 [(M+H)$^+$, M=C$_{24}$H$_{30}$N$_2$O$_2$].

7-Ethyl-8-(ethoxycarbonyl)-6-p-tolyl-1-(1,1-dimethoxymethyl)-2,2-dimethyl-2,3-dihydrodipyrrin (6ca)

Following a general procedure,[304] a solution of 5ca (64 mg, 0.17 mmol) in 1,4-dioxane (10 mL) was treated with SeO$_2$ (56 mg, 0.51 mmol). The reaction mixture was stirred at room temperature for 30 min. Ethyl acetate and water were then added. The organic layer was washed (brine), dried and concentrated to dryness. The crude product was treated directly with HC(OMe)$_3$ (5 mL) and TsOH.H$_2$O (20 mg, 0.10 mmol). After 1 h with stirring at room temperature, the reaction mixture was quenched by the addition of saturated aqueous NaHCO$_3$ solution, and then extracted with ethyl acetate. The organic layer was dried (Na$_2$SO$_4$) and concentrated. Column chromatography [silica, hexanes/ethyl acetate (4:1)] afforded a yellow oil (23 mg, 31%): $^1$H NMR δ 0.75 (t, J=7.2 Hz, 3H), 1.21 (s, 6H), 1.30 (t, J=6.9 Hz, 3H), 2.01 (q, J=7.2 Hz, 2H), 2.32 (s, 2H), 2.41 (s, 3H), 3.47 (s, 6H), 4.23 (q, J=6.9 Hz, 2H), 5.12 (s, 1H), 7.06-7.18 (m, 4H), 7.51 (d, J=3.3 Hz, 1H), 11.50 (b s, 1H); $^{13}$C NMR δ 14.7, 16.5, 17.9, 21.6, 21.9, 26.2, 46.2, 47.7, 54.7, 59.3, 102.4, 114.7, 124.3, 125.6, 128.3, 128.8, 129.4, 130.0, 136.8, 137.2, 147.8, 165.5, 181.1; ESI-MS obsd 439.2587, calcd 439.2591 [(M+H)$^+$, M=C$_{26}$H$_{34}$N$_2$O$_4$].

Diethyl 8,8,18,18-tetramethyl-3,13-diethyl-5,15-di-p-tolylbacteriochlorin-2,12-dicarboxylate (7ca-HBC)

Following a general procedure,[265] a solution of 6ca (21 mg, 0.048 mmol) in anhydrous CH$_2$Cl$_2$ (5 mL) was treated with 2,6-DTBP (220 μL, 0.96 mmol) followed by TMSOTf (45 μL, 0.24 mmol). The reaction mixture was stirred at room temperature for 15 h, and then diluted with $CH_2Cl_2$ and washed with saturated aqueous $NaHCO_3$. The organic layer was dried ($Na_2SO_4$) and concentrated. Column chromatography [silica, hexanes/ethyl acetate (5:1)] afforded a purple solid (6.0 mg, 33%): $^1$H NMR δ −0.54 (s, 2H), 1.15 ((t, J=7.2 Hz, 6H), 1.65 (t, J=6.9 Hz, 6H), 1.82 (s, 12H), 2.63 (s, 6H), 3.08 (q, J=7.2 Hz, 4H), 3.78 (s, 4H), 4.73 (q, J=6.9 Hz, 4H), 7.55 (ABq, ΔδAB=0.19, J=7.8 Hz, 4H), 9.51 (s, 2H); $^{13}$C NMR δ 14.8, 17.9, 20.7, 21.8, 26.6, 31.3, 45.8, 51.7, 61.1, 86.8, 115.2, 122.4, 129.1, 131.6, 132.5, 134.1, 137.6, 139.5, 142.7, 161.2, 167.1, 170.1; ESI-MS obsd 750.4142, calcd 750.4140 [(M)$^+$, M=$C_{48}H_{54}N_4O_4$]; $λ_{abs}$ 361, 387, 534, 757 nm ($CH_2Cl_2$).

Ethyl 5-[(4,4-dimethyl-5-methylenedihydrofuran-2 (3H)-ylidene)(p-tolyl)methyl]-4-phenyl-1H-pyrrole-3-carboxylate (3cd)

Following a general procedure,[6] a solution of 1c (658 mg, 3.05 mmol), 2d (520 mg, 1.52 mmol) and $BnNEt_3Cl$ (346 mg, 1.52 mmol) in dry DMF (12 mL) and $Et_3N$ (3 mL) was added to a Schlenk flask and deaerated by three freeze-pump-thaw cycles. A sample of $Pd(PPh_3)_4$ (114 mg, 0.099 mmol) was then added, and the resulting mixture was further deaerated. The reaction mixture was kept at 100° C. for 24 h, and then $CH_2Cl_2$ and water were added. The organic layer was dried ($Na_2SO_4$) and concentrated. Column chromatography [silica, hexanes/ethyl acetate (2:1)] afforded a white solid (250 mg, 38%): mp 137-139° C.; $^1$H NMR δ 0.90 (s, 6H), 1.23 (t, J=7.2 Hz, 3H), 2.19 (s, 2H), 2.35 (s, 3H), 4.23 (q, J=7.2 Hz, 2H), 7.15-7.41 (m, 9H), 7.51 (d, J=2.7 Hz, 1H), 8.22 (s, 1H); $^{13}$C NMR δ 14.5, 21.4, 24.5, 39.4, 41.3, 59.9, 114.5, 125.3, 125.7, 127.0, 127.3, 127.9, 128.2, 129.1, 129.4, 129.6, 130.0, 133.8, 134.7, 137.5, 147.2, 164.9, 180.2; ESI-MS obsd 430.2015, calcd 430.2013 [(M+H)$^+$, M=$C_{27}H_{27}NO_4$].

Ethyl 5-[(4,4-dimethyl-5-methylenedihydrofuran-2 (3H)-ylidene)(p-tolyl)methyl]-4-phenyl-1H-pyrrole-3-carboxylate (4cd)

Following a standard procedure,[6] a solution of $TiCp_2Cl_2$ (512 mg, 2.08 mmol) in toluene (33 mL) was treated dropwise with LiMe solution (1.6 M, 17 mL in $Et_2O$, 27 mmol) at 0° C. under an argon atmosphere. After 1 h at 0° C., saturated aqueous $NH_4Cl$ solution was added. The organic layer was washed (water and brine), dried ($Na_2SO_4$) and filtered. The filtrate was treated with lactone 3cd (185 mg, 0.431 mmol) and $TiCp_2Cl_2$ (4 mg). The solution was heated to 80° C. in the dark for 6 h under argon. Afterwards, the resulting mixture was allowed to cool to room temperature whereupon MeOH (0.5 mL), $NaHCO_3$ (20 mg) and water (5 µL) were added. The mixture was kept at 40° C. for another 12 h with stirring and then filtered through Celite. The filtrate was concentrated. Column chromatography [silica, hexanes/ethyl acetate (4:1)] afforded a yellow solid (140 mg, 76%): mp 123-125° C.; $^1$H NMR δ 0.84 (s, 6H), 1.23 (t, J=6.9 Hz, 3H), 2.00 (s, 2H), 2.33 (s, 3H), 3.90 (d, J=2.7 Hz, 1H), 4.23 (q, J=6.9 Hz, 2H), 4.36 (d, J=2.7 Hz, 1H), 7.13-7.43 (m, 9H), 7.48 (d, J=3.3 Hz, 1H), 8.10 (s, 1H); $^{13}$C NMR δ 14.5, 21.3, 27.0, 38.9, 43.8, 59.7, 81.4, 102.7, 114.4, 124.8, 126.6, 127.9, 128.6, 129.1, 129.4, 130.1, 134.9, 135.2, 136.2, 154.1, 164.9, 170.6; ESI-MS obsd 428.2216, calcd 428.2220 [(M+H)$^+$, M=$C_{28}H_{29}NO_3$].

7-Phenyl-8-(ethoxycarbonyl)-6-p-tolyl-1-methyl-2, 2-dimethyl-2,3-dihydrodipyrrin (5cd)

Following a general procedure,[6] a solution of 4ca (130 mg, 0.304 mmol) in DMF (10 mL) was treated with 1M HCl (0.5 mL). After 30 min, $NH_4OAc$ (700 mg, 9.13 mmol) and $Et_3N$ (1.2 mL, 9.2 mmol) were added, and the resulting mixture was stirred at 55° C. for 4 h. Then, the reaction was quenched by the addition of saturated aqueous $KH_2PO_4$ solution. Ethyl acetate (100 mL) was added, and the organic layer was washed (water), dried and concentrated. Column chromatography [silica, hexanes/ethyl acetate (5:1)] afforded a light yellow solid (88 mg, 68%): mp 117-119° C.; $^1$H NMR δ 0.79 (s, 6H), 1.23 (t, J=7.2 Hz, 3H), 1.86 (s, 2H), 1.96 (s, 3H), 2.33 (s, 3H), 4.20 (q, J=7.2 Hz, 2H), 7.10-7.50 (m, 10H), 8.11 (s, 1H); $^{13}$C NMR δ 14.5, 15.9, 21.4, 25.5, 44.6, 48.4, 59.7, 114.4, 117.8, 124.7, 124.8, 126.5, 127.9, 128.8, 130.0, 130.3, 131.3, 135.2, 136.6, 136.8, 154.9, 165.1, 189.4; ESI-MS obsd 427.2382, calcd 427.2380 [(M+H)$^+$, M=$C_{28}H_{30}N_2O_2$].

7-Phenyl-8-(ethoxycarbonyl)-6-p-tolyl-1-(1,1-dimethoxymethyl)-2,2-dimethyl-2,3-dihydrodipyrrin (6cd)

Following a general procedure,[304] a solution of 5cd (85 mg, 0.20 mmol) in 1,4-dioxane (10 mL) was treated with $SeO_2$ (66 mg, 0.60 mmol). The reaction mixture was stirred at room temperature for 30 min. Ethyl acetate and water were then added. The organic layer was washed (brine), dried and concentrated to dryness. The crude product was treated directly with $HC(OMe)_3$ (5 mL) and $TsOH \cdot H_2O$ (10 mg, 0.050 mmol). After 12 h with stirring at room temperature, the reaction mixture was quenched by the addition of saturated aqueous $NaHCO_3$ solution, and then extracted with ethyl acetate. The organic layer was dried ($Na_2SO_4$) and concentrated. Column chromatography [silica, hexanes/ethyl acetate (4:1)] afforded a brown oil (30 mg, 31%): $^1$H NMR δ 1.04 (t, J=7.2 Hz, 3H), 1.20 (s, 6H), 2.14 (s, 3H), 2.34 (s, 2H), 3.38 (s, 6H), 4.02 (q, J=7.2 Hz, 2H), 5.11 (s, 1H), 6.62-6.90 (m, 10H), 7.62 (d, J=3.3 Hz, 1H), 12.15 (s, 1H); $^{13}$C NMR δ 14.3, 21.2, 26.4, 46.8, 48.1, 50.5, 59.3, 113.2, 115.9, 124.5, 124.8, 125.0, 126.4, 128.4, 129.9, 130.0, 131.0, 134.6, 135.5, 136.3, 147.7, 165.0, 179.3; ESI-MS obsd 487.2591, calcd 487.2591 [(M+H)$^+$, M=$C_{30}H_{34}N_2O_4$].

Diethyl 8,8,18,18-tetramethyl-3,13-diphenyl-5,15-di-p-tolylbacteriochlorin-2,12-dicarboxylate (7cd-HBC)

Following a general procedure,[265] a solution of 6cd (25 mg, 0.051 mmol) in anhydrous $CH_2Cl_2$ (5 mL) was treated with 2,6-DTBP (234 µL, 1.0 mmol) followed by TMSOTf (50 µL, 0.25 mmol). The reaction mixture was stirred at room temperature for 15 h, and then diluted with $CH_2Cl_2$ and washed with saturated aqueous $NaHCO_3$. The organic layer was dried ($Na_2SO_4$) and concentrated. Column chromatography [silica, hexanes/ethyl acetate (4:1)] afforded a dark purple solid (7.0 mg, 32%): $^1$H NMR δ −0.90 (s, 2H), 1.41 (t, J=7.2 Hz, 6H), 1.78 (s, 12H), 2.36 (s, 6H), 3.77 (s, 4H), 4.15 (q, J=7.2 Hz, 4H), 7.03-7.27 (m, 10H), 7.45-7.76 (m, 10H), 9.50 (s, 2H); ESI-MS obsd 847.4191, calcd 847.4218 [(M+H)$^+$, M=$C_{56}H_{54}N_4O_4$]; $λ_{abs}$ 363, 538, 760 nm ($CH_2Cl_2$).

Ethyl (E)-5-(1-(4,4-dimethyl-5-oxodihydrofuran-2 (3H)-ylidene)ethyl)-4-phenyl-1H-pyrrole-3-carboxylate (3dd)

Following a general procedure,[6] a solution of 1d (665 mg, 4.75 mmol), 2d (810 mg, 2.38 mmol) and $BnNEt_3Cl$ (542 mg, 2.38 mmol) in dry DMF (16 mL) and Et$_3$N (4 mL) was added to a Schlenk flask and deaerated by three freeze-pump-thaw cycles. A sample of Pd(PPh$_3$)$_4$ (178 mg, 0.155 mmol) was then added, and the resulting mixture was further deaerated. The reaction mixture was kept at 100° C. for 24 h, and then CH$_2$Cl$_2$ and water were added. The organic layer was dried (Na$_2$SO$_4$) and concentrated. Column chromatography [silica, hexanes/ethyl acetate (2:1)] afforded a white solid (362 mg, 43%): mp 125-127° C.; $^1$H NMR δ 0.95 (s, 6H), 1.25 (t, J=7.2 Hz, 3H), 1.98 (s, 3H), 2.05 (s, 2H), 4.19 (q, J=7.2 Hz, 2H), 7.18-7.34 (m, 5H), 7.47 (s, 1H), 8.41 (s, 1H); $^{13}$C NMR δ 14.8, 16.8, 24.6, 40.0, 59.8, 103.7, 118.4, 124.8, 126.8, 128.0, 129.5, 130.3, 134.9, 146.7, 180.3; ESI-MS obsd 354.1701, calcd 354.1700 [(M+H)$^+$, M=C$_{21}$H$_{23}$NO$_4$].

Ethyl (E)-5-(1-(4,4-dimethyl-5-methylenedihydrofuran-2(3H)-ylidene)ethyl)-4-phenyl-1H-pyrrole-3-carboxylate (4dd)

Following a standard procedure,$^6$ a solution of TiCp$_2$Cl$_2$ (588 mg, 2.39 mmol) in toluene (9 mL) was treated dropwise with LiMe solution (1.6 M, 3.5 mL in Et$_2$O, 5.6 mmol) at 0° C. under an argon atmosphere. After 1 h at 0° C., saturated aqueous NH$_4$Cl solution was added. The organic layer was washed (water and brine), dried (Na$_2$SO$_4$) and filtered. The filtrate was treated with lactone 3dd (178 mg, 0.504 mmol) and TiCp$_2$Cl$_2$ (7 mg). The solution was heated to 80° C. in the dark for 6 h under argon. Afterwards, the resulting mixture was allowed to cool to room temperature whereupon MeOH (0.60 mL), NaHCO$_3$ (25 mg) and water (6 μL) were added. The mixture was kept at 40° C. for another 12 h with stirring and then filtered through Celite. The filtrate was concentrated. Column chromatography [silica, hexanes/ethyl acetate (5:1)] afforded a yellow solid (124 mg, 70%): mp 119-121° C.; $^1$H NMR δ 0.92 (s, 6H), 1.19 (t, J=7.2 Hz, 3H), 1.87 (s, 3H), 1.93 (s, 2H), 3.87 (d, J=2.1 Hz, 1H), 4.17 (q, J=7.2 Hz, 2H), 4.29 (d, J=2.1 Hz, 1H), 7.21-7.30 (m, 5H), 7.42 (d, J=3.0 Hz, 1H), 8.35 (s, 1H); $^{13}$C NMR δ 14.5, 16.2, 27.2, 39.9, 42.0, 59.7, 80.2, 98.1, 114.7, 122.8, 123.9, 126.4, 127.7, 130.4, 130.8, 135.2, 152.4, 165.1, 170.3; ESI-MS obsd 352.1911, calcd 352.1907 [(M+H)$^+$, M=C$_{22}$H$_{25}$NO$_3$].

7-Phenyl-8-(ethoxycarbonyl)-1,6-dimethyl-2,2-dimethyl-2,3-dihydrodipyrrin (5dd)

Following a general procedure,$^6$ a solution of 4dd (120 mg, 0.342 mmol) in DMF (10 mL) was treated with 1M HCl (0.5 mL). After 30 min, NH$_4$OAc (524 mg, 6.85 mmol) and Et$_3$N (1.0 mL, 7.2 mmol) were added, and the resulting mixture was stirred at 55° C. for 4 h. Then, the reaction was quenched by the addition of saturated aqueous KH$_2$PO$_4$ solution. Ethyl acetate (100 mL) was added, and the organic layer was washed (water), dried and concentrated. Column chromatography [silica, hexanes/ethyl acetate (4:1)] afforded a yellow solid (62 mg, 51%): mp 111-112° C.; $^1$H NMR δ 1.06 (t, J=7.2 Hz, 3H), 1.17 (s, 6H), 1.41 (s, 3H), 2.14 (s, 3H), 2.48 (s, 2H), 4.21 (q, J=7.2 Hz, 2H), 7.28-7.29 (m, 5H), 7.48 (d, J=3.3 Hz, 1H), 12.18 (bs, 1H); $^{13}$C NMR δ 14.3, 15.8, 18.1, 26.3, 43.8, 47.8, 59.2, 114.4, 115.6, 123.8, 123.9, 126.5, 127.2, 130.8, 131.1, 137.8, 148.0-165.3, 185.1; ESI-MS obsd 351.2073, calcd 351.2067 [(M+H)$^+$, M=C$_{22}$H$_{26}$N$_2$O$_2$].

7-Phenyl-8-(ethoxycarbonyl)-6-methyl-1-(1,1-dimethoxymethyl)-2,2-dimethyl-2,3-dihydrodipyrrin (6dd)

Following a general procedure,$^{304}$ a solution of 5dd (48 mg, 0.137 mmol) in 1,4-dioxane (10 mL) was treated with SeO$_2$ (44 mg, 0.396 mmol). The reaction mixture was stirred at room temperature for 30 min. Ethyl acetate and water were then added. The organic layer was washed (brine), dried and concentrated to dryness. The crude product was treated directly with HC(OMe)$_3$ (5 mL) and TsOH.H$_2$O (10 mg, 0.050 mmol). After 1 h with stirring at room temperature, the reaction mixture was quenched by the addition of saturated aqueous NaHCO$_3$ solution, and then extracted with ethyl acetate. The organic layer was dried (Na$_2$SO$_4$) and concentrated. Column chromatography [silica, hexanes/ethyl acetate (4:1)] afforded a brown oil (27 mg, 48%): $^1$H NMR δ 1.06 (t, J=7.2 Hz, 3H), 1.27 (s, 6H), 1.45 (s, 3H), 2.52 (s, 2H), 3.45 (s, 6H), 4.04 (q, J=7.2 Hz, 2H), 5.11 (s, 1H), 7.26-7.31 (m, 5H), 7.51 (d, J=3.3 Hz, 1H), 12.02 (bs, 1H); $^{13}$C NMR δ 14.3, 18.4, 26.6, 45.5, 47.5, 54.5, 59.2, 102.2, 115.8, 118.1, 124.4, 124.9, 126.6, 127.3, 130.5, 131.0, 137.6, 147.2, 165.2, 179.6; ESI-MS obsd 411.2283, calcd 411.2278 [(M+H)$^+$, M=C$_{24}$H$_{30}$N$_2$O$_4$].

Diethyl 5,8,8,15,18,18-hexmethyl-3,13-diphenylbacteriochlorin-2,12-dicarboxylate (7dd-HBC)

Following a general procedure,$^{265}$ a solution of 6dd (25 mg, 0.061 mmol) in anhydrous CH$_2$Cl$_2$ (9 mL) was treated with 2,6-DTBP (280 μL, 1.2 mmol) followed by TMSOTf (56 μL, 0.30 mmol). The reaction mixture was stirred at room temperature for 15 h, and then diluted with CH$_2$Cl$_2$ and washed with saturated aqueous NaHCO$_3$. The organic layer was dried (Na$_2$SO$_4$) and concentrated. Column chromatography [silica, hexanes/ethyl acetate (4:1)] afforded a dark purple solid (6.1 mg, 29%): $^1$H NMR δ −0.19 (s, 2H), 1.15 (t, J=6.9 Hz, 6H), 1.91 (s, 12H), 2.92 (s, 6H), 4.06 (s, 4H), 4.39 (q, J=6.9 Hz, 4H), 7.57-7.72 (m, 10H), 9.62 (s, 2H); $^{13}$C NMR δ 14.1, 21.0, 29.9, 31.6, 45.7, 51.0, 60.8, 96.7, 110.0, 123.3, 127.5, 128.0, 130.8, 132.9, 133.1, 137.7, 139.4, 161.9, 166.7, 170.3; ESI-MS obsd 694.3514, calcd 694.3514 [(M)$^+$, M=C$_{44}$H$_{46}$N$_4$O$_4$]; λ$_{abs}$ 365, 547, 755 nm (CH$_2$Cl$_2$).

Ethyl 5-[(4,4-dimethyl-5-methylenedihydrofuran-2 (3H)-ylidene)methyl]-1H-pyrrole-3-carboxylate (3ab)

Following a general procedure,$^6$ a solution of 1a (1.26 g, 10.1 mmol), 2a (1.32 g, 5.00 mmol) and BnNEt$_3$Cl (1.14 g, 5.00 mmol) in dry acetonitrile (30 mL) and Et$_3$N (6 mL) was added to a Schlenk flask and deaerated by three freeze-pump-thaw cycles. A sample of Pd(PPh$_3$)$_4$ (375 mg, 0.325 mmol) was then added, and the resulting mixture was further deaerated. The reaction mixture was kept at 80° C. for 24 h, and then CH$_2$Cl$_2$ and water were added. The organic layer was dried (Na$_2$SO$_4$) and concentrated. Column chromatography [silica, hexanes/ethyl acetate (3:1)] afforded a clear yellow solid (727 mg, 55%): mp 110-111° C.; $^1$H NMR δ 1.35-1.38 (m, 9H), 2.93 (d, J=2.4 Hz, 1H), 4.30 (q, J=7.2 Hz, 2H), 6.18 (dd, J=1.5, 2.4 Hz, 1H), 6.39 (s, 1H), 7.39 (dd, J=1.5, 1.5 Hz, 1H), 9.44 (s, 1H); $^{13}$C NMR δ 14.7, 25.5, 40.2, 40.7, 60.2, 97.9, 107.0, 117.7, 123.7, 127.8, 148.3, 165.5, 180.3; ESI-MS obsd 264.1227, calcd 264.1230 [(M+H)$^+$, M=C$_{14}$H$_{17}$NO$_4$].

Ethyl 5-[(4,4-dimethyl-5-methylenedihydrofuran-2 (3H)-ylidene)methyl]-1H-pyrrole-3-carboxylate (4ab)

Following a standard procedure,$^6$ a solution of TiCp$_2$Cl$_2$ (2.13 g, 8.68 mmol) in toluene (23 mL) was treated dropwise with LiMe solution (1.6 M, 12 mL in Et$_2$O, 19 mmol) at 0° C. under an argon atmosphere. After 1 h at 0° C., saturated aqueous NH$_4$Cl solution was added. The organic layer was washed (water and brine), dried (Na$_2$SO$_4$) and filtered. The filtrate was treated with lactone 3ab (480 mg, 1.83 mmol) and TiCp$_2$Cl$_2$ (27 mg). The solution was heated to 80° C. in the dark for 6 h under argon. Afterwards, the resulting mixture was allowed to cool to room temperature whereupon MeOH (2.2 mL), NaHCO$_3$ (90 mg) and water (22 µL) were added. The mixture was kept at 40° C. for another 12 h with stirring and then filtered through Celite. The filtrate was concentrated. Column chromatography [silica, hexanes/ethyl acetate (4:1)] afforded a yellow solid (231 mg, 48%): mp 99-101° C.; $^1$H NMR δ 1.25 (s, 6H), 1.34 (t, J=7.2 Hz, 3H), 2.68 (d, J=1.8 Hz, 2H), 4.00 (d, J=2.4 Hz, 1H), 4.29 (q, J=7.2 Hz, 2H), 4.37 (d, J=2.4 Hz, 1H), 5.85 (t, J=1.5 Hz, 1H), 6.31 (s, 1H), 7.31 (m, 1H), 8.85 (s, 1H); $^{13}$C NMR δ 14.7, 28.1, 40.3, 42.7, 60.1, 92.5, 105.6, 117.5, 122.8, 129.8, 154.9, 165.6, 169.7; ESI-MS obsd 162.1429, calcd 262.1438 [(M+H)$^+$, M=C$_{15}$H$_{19}$NO$_3$].

8-(Ethoxycarbonyl)-1-methyl-2,2-dimethyl-2,3-dihydrodipyrrin (5ab)

Following a general procedure,[6] a solution of 4ab (220 mg, 0.842 mmol) in DMF (20 mL) was treated with 1M HCl (0.5 mL). After 30 min, NH$_4$OAc (1.31 g, 17.1 mmol) and Et$_3$N (2.2 mL, 17 mmol) were added, and the resulting mixture was stirred at 55° C. for 6 h. Then, the reaction was quenched by the addition of saturated aqueous KH$_2$PO$_4$ solution. Ethyl acetate (100 mL) was added, and the organic layer was washed (water), dried and concentrated. Column chromatography [silica, hexanes/ethyl acetate (8:1)] afforded a yellow solid (87 mg, 40%): mp 110-112° C.; $^1$H NMR δ 1.16 (s, 6H), 1.33 (t, J=7.2 Hz, 3H), 2.13 (s, 2H), 2.55 (d, J=1.8 Hz, 2H), 4.27 (q, J=7.2 Hz, 2H), 5.79 (s, 1H), 6.41 (t, J=1.8 Hz, 1H), 7.40 (m, 1H), 11.2 (bs, 1H); $^{13}$C NMR δ 14.8, 15.8, 25.9, 44.1, 48.6, 59.7, 105.8, 108.2, 116.5, 124.2, 132.2, 150.4, 165.6, 187.5; ESI-MS obsd 261.1595, calcd 261.1598 [(M+H)$^+$, M=C$_{15}$H$_{20}$N$_2$O$_2$].

8-(Ethoxycarbonyl)-1-(1,1-dimethoxymethyl)-2,2-dimethyl-2,3-dihydrodipyrrin (6ab)

Following a general procedure,[304] a solution of 5ab (80 mg, 0.42 mmol) in 1,4-dioxane (10 mL) was treated with SeO$_2$ (139 mg, 1.25 mmol). The reaction mixture was stirred at room temperature for 30 min. Ethyl acetate and water were then added. The organic layer was washed (brine), dried and concentrated to dryness. The crude product was treated directly with HC(OMe)$_3$ (5 mL) and TsOH.H$_2$O (25 mg, 0.13 mmol). After 12 h with stirring at room temperature, the reaction mixture was quenched by the addition of saturated aqueous NaHCO$_3$ solution, and then extracted with ethyl acetate. The organic layer was dried (Na$_2$SO$_4$) and concentrated. Column chromatography [silica, hexanes/ethyl acetate (4:1)] afforded a yellow oil (41 mg, 30%): $^1$H NMR δ 1.27 (s, 6H), 1.33 (t, J=7.2 Hz, 3H), 2.59 (d, J=1.5 Hz, 2H), 3.44 (s, 6H), 4.27 (q, J=7.2 Hz, 2H), 5.95 (m, 1H), 6.47 (m, 1H), 7.42 (m, 1H), 10.99 (bs, 1H); $^{13}$C NMR δ 14.7, 26.1, 45.8, 48.4, 54.7, 59.8, 102.3, 108.9, 109.4, 116.6, 124.9, 131.8, 149.4, 165.4, 182.1; ESI-MS obsd 21.1797, calcd 321.1801 [(M+H)$^+$, M=C$_{17}$H$_{24}$N$_2$O$_4$].

Diethyl 8,8,18,18-tetramethyl-3,13-bacteriochlorin-2,12-dicarboxylate (7ab-HBC)

Following a general procedure,[265] a solution of 6ab (27 mg, 84 µmol) in anhydrous CH$_2$Cl$_2$ (5 mL) was treated with 2,6-DTBP (385 µL, 1.68 mmol) followed by TMSOTf (79 µL, 0.42 mmol). The reaction mixture was stirred at room temperature for 24 h, and then diluted with CH$_2$Cl$_2$ and washed with saturated aqueous NaHCO$_3$. The organic layer was dried (Na$_2$SO$_4$) and concentrated. Column chromatography [silica, hexanes/ethyl acetate (5:1)] afforded a dark green solid (2.3 mg, 6.0%): $^1$H NMR δ −1.46 (s, 2H), 1.70 (t, J=6.9 Hz, 6H), 1.98 (s, 12H), 4.38 (s, 4H), 4.75 (q, J=6.9 Hz, 4H), 8.78 (s, 2H), 9.17 (s, 2H), 9.71 (s, 2H); ESI-MS obsd 515.2658, calcd 515.2653 [(M+H)$^+$, M=C$_{30}$H$_{34}$N$_4$O$_4$]; $\lambda_{abs}$ 353, 383, 519, 758 nm (CH$_2$Cl$_2$).

Scheme 13. Synthesis of Meso-Napthyl bacteriochlorins

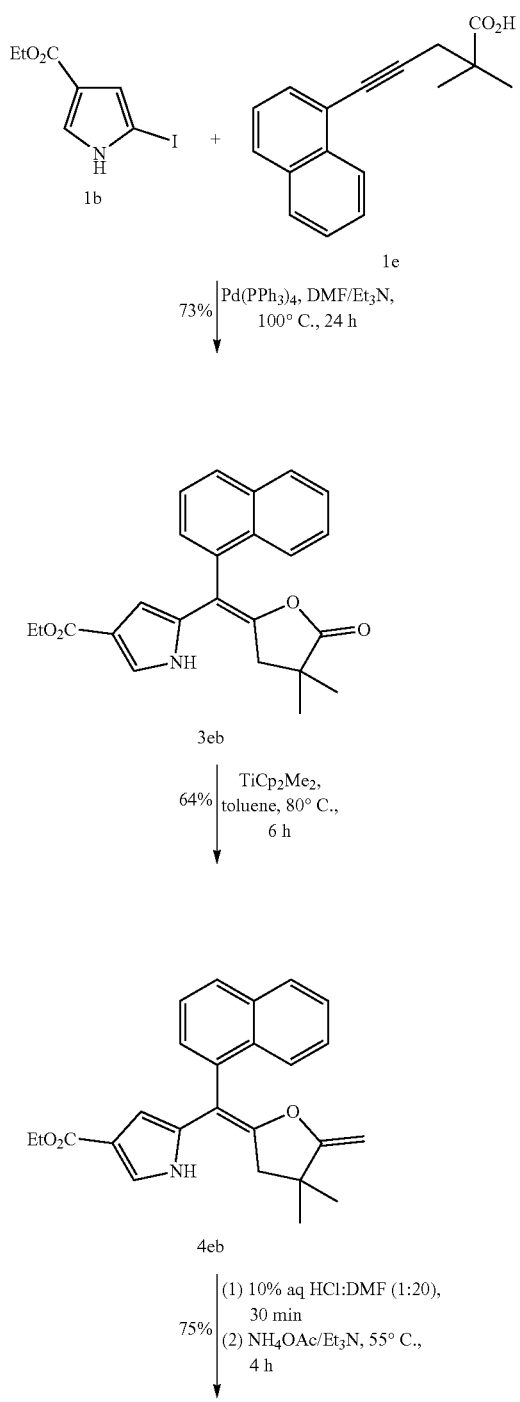

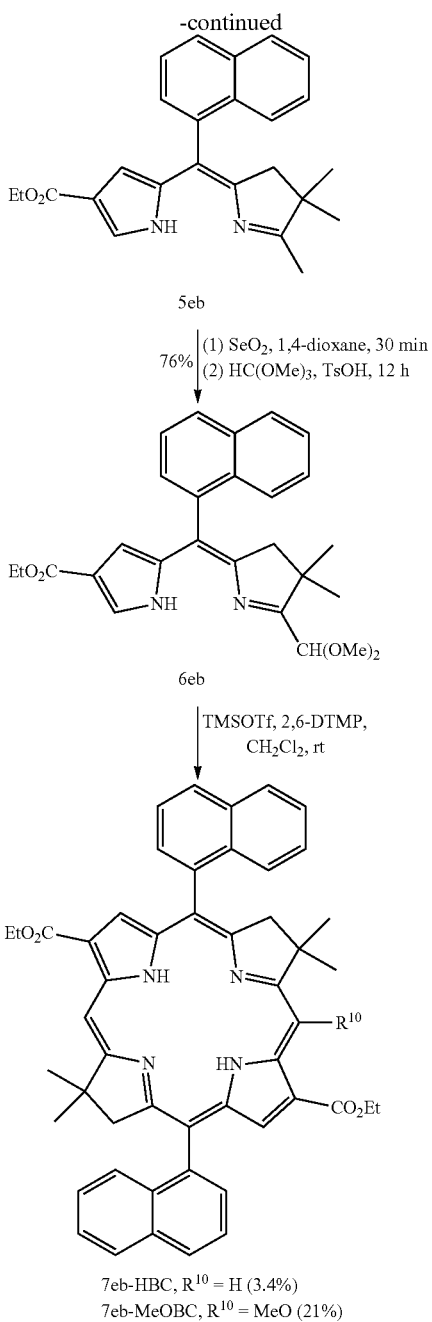

5eb

76% | (1) SeO₂, 1,4-dioxane, 30 min
(2) HC(OMe)₃, TsOH, 12 h

6eb

TMSOTf, 2,6-DTMP, CH₂Cl₂, rt

7eb-HBC, R¹⁰ = H (3.4%)
7eb-MeOBC, R¹⁰ = MeO (21%)

2,2-Dimethyl-5-(1-naphthyl)pent-4-ynoic acid (1e)

A solution of methyl 2,2-dimethylpent-4-ynoate (7.01 g, 50.1 mmol) in Et₃N was added to a Schlenk flask and treated with CuI (272 mg, 1.50 mmol), Pd(PPh₃)₄Cl₂ (355 mg, 0.500 mmol) and PPh₃ (525 mg, 2.00 mmol). The resulting mixture was deaerated by three freeze-pump-thaw cycles and then kept at 80° C. for 12 h. Upon cooling to room temperature, 200 mL CH₂Cl₂ was added, whereupon the reaction mixture was filtered through Celite. The filtrate was concentrated to dryness and sequentially treated with KOH (8.40 g, 150 mol), water (30 mL), MeOH (30 mL) and THF (90 mL) under argon. After 12 h, 6 M HCl was added until the reaction mixture exhibited pH=1. The organic layer was then extracted with CH₂Cl₂. The organic extract was dried (Na₂SO₄) and concentrated. Column chromatography [silica, hexanes/ethyl acetate (3:1)] afforded a white solid (7.64 g, 57%): mp 153-155° C.; ¹H NMR δ 1.47 (s, 6H), 2.88 (s, 6H), 7.46-7.84 (m, 6H), 8.33 (d, J=8.4 Hz, 1H); ¹³C NMR δ 24.8, 30.9, 42.8, 81.2, 91.5, 121.5, 125.4, 126.4, 126.5, 126.8, 128.4, 128.5, 130.5, 133.4, 133.7, 183.9; ESI-MS obsd 253.1319, calcd 253.1223 [(M+H)⁺, M=C₁₇H₁₆O₂].

4-Carboethoxy-(E)-2-[(4,4-dimethyl-5-oxodihydrofuran-2(3H)-ylidene)(1-naphthyl)methyl]pyrrole (3eb)

Following a general procedure,⁶ a solution of 1e (2.52 g, 7.87 mmol), 2b (1.33 g, 5.00 mmol) and BnNEt₃Cl (1.14 mg, 5.00 mmol) in dry acetonitrile (20 mL) and Et₃N (5 mL) was added to a Schlenk flask and deaerated by three freeze-pump-thaw cycles. A sample of Pd(PPh₃)₄ (375 mg, 0.325 mmol) was then added, and the resulting mixture was further deaerated. The reaction mixture was kept at 80° C. for 24 h, allowed to cool to room temperature, and then CH₂Cl₂ and water were added. The organic layer was dried (Na₂SO₄) and concentrated. Column chromatography [silica, hexanes/ethyl acetate (4:1)] afforded a yellow solid (1.42 g, 73%): mp 137-139° C.; ¹H NMR δ 1.31-1.41 (m, 9H), 3.25 (s, 2H), 4.26 (q, J=7.2 Hz, 2H), 6.64 (dd, J=2.7, 1.5 Hz, 1H), 7.15 (dd, J=2.7, 1.5 Hz, 1H), 7.39-7.89 (m, 8H); ¹³C NMR δ 14.7, 24.8, 25.5, 40.3, 41.9, 60.2, 107.4, 109.6, 110.0, 117.8, 123.3, 125.2, 125.9, 126.4, 126.9, 128.5, 128.8, 129.2, 130.1, 131.9, 132.1, 134.3, 145.6, 165.1, 179.6; ESI-MS obsd 390.1704, calcd 390.1700 [(M+H)⁺, M=C₂₄H₂₃NO₄].

4-Carboethoxy-(E)-2-[(4,4-dimethyl-5-methylenedihydrofuran-2(3H)-ylidene)(1-naphthyl)methyl]pyrrole (4eb)

Following a general procedure,⁶ a solution of TiCp₂Cl₂ (4.48 g, 18.1 mmol) in toluene (40 mL) at 0° C. under an argon atmosphere was treated dropwise with LiMe solution (1.6 M, 23 mL in THF/heptane/ethylbenzene, 36 mmol), then the resulting solution was stirred at 0° C. After 1 h, saturated aqueous NH₄Cl solution was added. The organic layer was washed (water and brine), dried (Na₂SO₄) and filtered. The filtrate was treated with lactone 3eb (1.41 g, 3.62 mmol) and TiCp₂Cl₂ (55 mg). The resulting solution was heated at 80° C. in the dark for 6 h. Afterwards, the resulting mixture was allowed to cool to room temperature whereupon MeOH (4.4 mL), NaHCO₃ (183 mg) and water (44 μL) were added. The resulting solution was kept at 40° C. for 12 h with stirring and then filtered through Celite. The filtrate was concentrated. Column chromatography [silica, hexanes/ethyl acetate (4:1)] afforded a white solid (903 mg, 64%): mp 134-136° C.; ¹H NMR δ 1.32-1.36 (m, 9H), 3.01 (s, 2H), 3.91 (d, J=2.2 Hz, 1H), 4.13 (d, J=2.2 Hz, 1H), 4.28 (q, J=7.2 Hz, 2H), 6.55 (dd, J=2.7, 1.5 Hz, 1H), 7.09 (dd, J=2.7, 1.5 Hz, 1H), 7.38-7.52 (m, 4H), 7.70 (s, 1H), 7.86 (d, J=1.5 Hz, 1H), 7.88 (d, J=1.5 Hz, 2H); ¹³C NMR δ 14.6, 27.9, 40.2, 43.8, 59.8, 81.3, 104.0, 106.0, 117.2, 122.3, 125.7, 125.8, 126.0, 128.3, 128.4, 128.7, 132.1, 132.2, 133.5, 134.1, 151.9, 164.2, 169.4; ESI-MS obsd 388.1908, calcd 388.1907 [(M+H)⁺, M=C₂₅H₂₅NO₃].

8-Ethoxycarbonyl-2,3-dihydro-1,2,2-trimethyl-5-(1-naphthyl)dipyrrin (5eb)

Following a general procedure,⁶ a solution of 4eb (899 mg, 2.32 mmol) in DMF (50 mL) was treated with 1 M HCl (2.5 mL). After 30 min, NH$_4$OAc (4.77 g, 46.4 mmol) and Et$_3$N (6.7 mL, 46 mmol) were added, and the mixture was stirred at 55° C. for 4 h. Then, the reaction was quenched by the addition of saturated aqueous KH$_2$PO$_4$ solution. Ethyl acetate (200 mL) was added, and the organic layer was washed (water), dried and concentrated. Column chromatography [silica, hexanes/ethyl acetate (5:1)] afforded a yellow solid (678 mg, 75%): mp 133-135° C.; $^1$H NMR δ 1.07 (s, 3H), 1.11 (s, 3H), 1.22 (t, J=7.2 Hz, 3H), 2.00-2.26 (m, 5H), 4.18 (q, J=7.2 Hz, 2H), 5.79 (t, J=1.8 Hz, 1H), 7.36-7.54 (m, 5H), 7.82-7.91 (m, 3H), 11.95 (s, 1H); $^{13}$C NMR δ 14.7, 16.0, 25.9, 26.0, 43.7, 48.3, 59.7, 109.6, 116.3, 118.1, 124.4, 125.7, 125.9, 126.0, 126.4, 127.8, 128.0, 128.6, 132.1, 134.1, 134.9, 136.4, 149.3, 165.5, 187.7; ESI-MS obsd 387.2081, calcd 387.2067 [(M+H)$^+$, M=C$_{25}$H$_{26}$N$_2$O$_2$].

8-Ethoxycarbonyl-2,3-dihydro-1-(1,1-dimethoxymethyl)-2,2-dimethyl-5-(1-naphthyl)dipyrrin (6eb)

Following a general procedure,$^{304}$ a solution of 5cb (668 mg, 1.73 mmol) in 1,4-dioxane (25 mL) was treated with SeO$_2$ (576 mg, 5.19 mmol). The reaction mixture was stirred at room temperature for 30 min. Ethyl acetate and water were then added, and the organic layer was washed (brine), dried and concentrated. The resulting crude solid was treated directly with HC(OMe)$_3$ (30 mL) and TsOH.H$_2$O (99 mg, 0.519 mmol). After 12 h, the reaction mixture was quenched by the addition of saturated aqueous NaHCO$_3$ solution followed by extraction with ethyl acetate. The organic layer was dried (Na$_2$SO$_4$) and concentrated. Column chromatography [silica, hexanes/ethyl acetate (2:1)] afforded a yellow oil (591 mg, 76%): $^1$H NMR δ 1.17-1.26 (m, 9H), 2.15 (Δδ$_{AB}$=0.175, J=17.1 Hz, 2H), 3.53 (s, 6H), 4.17 (q, J=7.2 Hz, 2H), 5.21 (s, 1H), 5.86 (t, J=1.8 Hz, 1H), 7.39-7.57 (m, 5H), 7.82-7.91 (m, 3H), 11.66 (s, 1H); $^{13}$C NMR δ 14.7, 26.1, 26.3, 45.3, 48.1, 54.7, 54.9, 59.7, 102.2, 110.7, 116.4, 121.4, 125.2, 125.6, 125.9, 126.1, 126.5, 127.5, 128.2, 128.6, 131.8, 134.1, 134.5, 136.0, 148.5, 165.4, 182.2; ESI-MS obsd 447.2290, calcd 447.2278 [(M+H)$^+$, M=C$_{27}$H$_{30}$N$_2$O$_4$].

2,12-Dicarboethoxy-8,8,18,18-tetramethyl-5,15-bis(1-naphthyl)bacteriochlorin (7eb-HBC)

Following a general procedure,$^{265}$ a solution of 6eb (587 mg, 1.32 mmol) in anhydrous CH$_2$Cl$_2$ (72 mL) was treated with 2,6-DTBP (5.02 g, 26.3 mmol) followed by TMSOTf (1.46 g, 6.58 mmol). The reaction mixture was stirred at room temperature for 18 h, diluted with CH$_2$Cl$_2$ and washed with saturated aqueous NaHCO$_3$. The organic layer was dried (Na$_2$SO$_4$) and concentrated. Column chromatography [silica, hexanes/ethyl acetate (10:1)] gave two bands (both purple). The first band [R$_f$=0.43, TLC, silica, hexanes/ethyl acetate (10:1)] was isolated and concentrated to afford the title compound as a dark purple solid (17 mg, 3.4%). The second band [R$_f$=0.12, TLC, silica, hexanes/ethyl acetate (10:1)] afforded bacteriochlorin 7eb-MeOBc as a dark purple solid (110 mg, 21%). Data for the title compound: $^1$H NMR δ −0.78 (s, 2H), 1.55 (t, J=7.2 Hz, 3H), 1.78 (d, J=3.0 Hz, 6H), 1.86 (d, J=2.7 Hz, 6H), 3.58-3.88 (m, 4H), 4.57-4.64 (m, 4H), 7.19-7.23 (m, 4H), 7.52-7.55 (m, 2H), 7.81-8.22 (m, 2H), 8.48 (d, J=1.2 Hz, 2H), 9.82 (s, 2H); $^{13}$C NMR δ 14.9, 31.0, 31.3, 31.4, 46.2, 50.6, 61.1, 98.3, 113.4, 122.6, 125.6, 126.1, 126.2, 126.8, 128.7, 130.6, 130.7, 133.9, 134.5, 135.1, 135.9, 139.2, 161.3, 165.8, 172.94, 127.97; MALDI-MS obsd 767.2 calcd 766.3514 (M$^+$); ESI-MS obsd 766.3512, calcd 766.3514 [(M)$^+$, M=C$_{50}$H$_{46}$N$_4$O$_4$]; λ$_{abs}$ 359, 383, 539, 759 nm (CH$_2$Cl$_2$). Data for 2,12-dicarboethoxy-10-methoxy-8,8,18,18-tetramethyl-5,15-bis(1-naphthyl)bacteriochlorin (7eb-MeOBC): $^1$H NMR δ −0.75 (s, 1H), −0.62 (s, 1H), 1.21-1.55 (m, 6H), 1.77-1.91 (m, 12H), 3.49-3.80 (m, 4H), 4.06 (s, 3H), 4.51-4.59 (m, 4H), 7.18-7.26 (m, 4H), 7.49-7.54 (m, 2H), 7.80-8.21 (m, 9H), 8.40 (t, J=2.1 Hz, 1H), 9.59 (s, 1H); $^{13}$C NMR δ 14.4, 14.8, 29.1, 29.3, 30.7, 30.9, 46.2, 47.1, 47.2, 50.2, 53.2, 61.0, 61.9, 68.1, 97.1, 112.8, 113.7, 121.6, 122.4, 125.2, 125.6, 126.1, 126.2, 126.6, 126.7, 127.0, 128.6, 128.7, 129.9, 130.5, 130.8, 132.4, 133.9, 134.3, 134.4, 135.4, 136.7, 138.0, 139.2, 139.5, 159.7, 160.4, 165.7, 166.2, 168.2, 173.4, 173.5; MALDI-MS obsd 797.2, calcd 796.3619 (M$^+$); ESI-MS obsd 796.3615, calcd 796.3619 [(M)$^+$, M=C$_{51}$H$_{48}$N$_4$O$_5$]; λ$_{abs}$ 364, 381, 547, 748 nm (CH$_2$Cl$_2$).

REFERENCES

1. *The Chlorophylls*; Vernon, L. P.; Seely, G. R. Academic Press: New York, USA, 1966.
2. Scheer, H. In *Chlorophylls and Bacteriochlorophylls: Biochemistry, Biophysics, Functions and Applications*; Grimm, B., Porra, R. J., Rüdiger, W., Scheer, H., Eds.; Springer: Dordrecht, The Netherlands, 2006; pp 1-26.
2. Chew, A. G. M.; Bryant, D. A. *Annu. Rev. Microbiol.* 2007, 61, 113-129.
3. Chen, Y.; Li, G.; Pandey, R. K. *Curr. Org. Chem.* 2004, 8, 1105-1134.
4. (a) Dorough, G. D.; Miller, J. R. *J. Am. Chem. Soc.* 1952, 74, 6106-6108. (b) Whitlock, H. W., Jr.; Hanauer, R.; Oester, M. Y.; Bower, B. K. *J. Am. Chem. Soc.* 1969, 91, 7485-7489.
5. (a) Minehan, T. G.; Kishi, Y. *Angew. Chem. Int. Ed.* 1999, 38, 923-925. (b) Minehan, T. G.; Cook-Blumberg, L.; Kishi, Y.; Prinsep, M. R.; Moore, R. E. *Angew. Chem. Int. Ed.* 1999, 38, 926-928.
6. (a) Jacobi, P. A.; Liu, H. *J. Org. Chem.* 1999, 64, 1778-1779. (b) Jacobi, P.; Lanz, S.; Ghosh, I. *Org. Lett.* 2001, 3, 831-834. (c) O'Neal, W.; Roberts, W.; Ghosh, I.; Wang, H.; Jacobi, P. *J. Org. Chem.* 2006, 71, 3472-3480.
7. Hodge, P.; Rickards, R. W. *J. Chem. Soc.,* 1965, 459-470.
8. Anderson, H. J.; Lee, S.-F. *Can. J. Chem.,* 1965, 43, 409-414.
9. Trost, B. M.; Dong, G. *J. Am. Chem. Soc.* 2006, 128, 6054-6055.
219. Fan, D.; Taniguchi, M.; Lindsey, J. S. *J. Org. Chem.* 2007, 72, 5350-5357.
184. Kim, H.-J.; Lindsey, J. S. *J. Org. Chem.* 2005, 70, 5475-5486.
304. Reddy, K. R.; Lubian, E.; Pavan, M. P.; Kim, H.-J.; Yang, E.; Holten, D.; Lindsey, J. S. *New J. Chem.* 2013, 37, 1157-1173.
265. Krayer, M.; Ptaszek, M.; Kim, H.-J.; Meneely, K. R.; Fan, D.; Secor, K.; Lindsey, J. S. *J. Org. Chem.* 2010, 75, 1016-1039.
332. Lindsey, J. S. *Chem. Rev.* 2015, 115, 6534-6620.
A1. Whitlock, H. W., Jr.; Hanauer, R.; Oester, M. Y.; Bower, B. K. *J. Am. Chem. Soc.* 1969, 91, 7485-7489.
A2. Bruckner, C.; Dolphin, D. *Tetrahedron Lett.* 1995, 36, 9425-9428.
120. Taniguchi, M.; Ra, D.; Mo, G.; Balasubramanian, T.; Lindsey, J. S. *J. Org. Chem.* 2001, 66, 7342-7354.

The foregoing is illustrative of the present invention, and is not to be construed as limiting thereof. The invention is defined by the following claims, with equivalents of the claims to be included therein.

That which is claimed is:
1. A method of making a compound of Formula I:

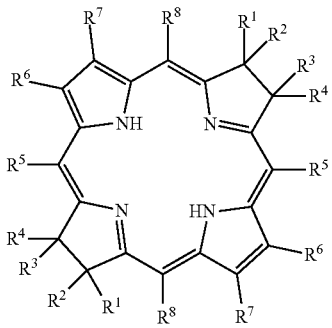

(I)

or a metal conjugate thereof, wherein:
  each $R^1$, $R^2$, $R^3$, $R^4$, $R^5$, $R^6$, $R^7$ and $R^8$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, a hydrophilic group, a linking group, a surface attachment group, and a targeting group, wherein the hydrophilic group is selected from the group consisting of a polyol, polyalkylene oxide group, ionic group, polar group, and any combination thereof, wherein the linking group is selected from the group consisting of aryl, alkyl, heteroaryl, heteroalkyl, a peptide, a polysaccharide, and any combination thereof, and wherein the targeting group is selected from the group consisting of an antibody, a ligand, one member of a ligand-receptor binding pair, a nucleic acid, a protein, a liposomal suspension, and any combination thereof;
  or $R^1$ and $R^2$ together are =O or spiroalkyl;
  or $R^3$ and $R^4$ together are =O or spiroalkyl;
  where $R^6$ and $R^7$, or $R^7$ and $R^8$, together represent a fused aromatic or heteroaromatic ring systems;
  said method comprising condensing a pair of compounds of Formula II:

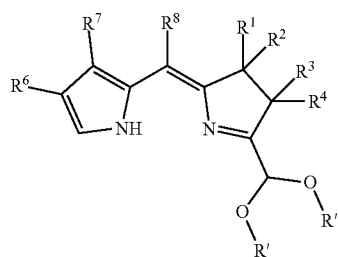

(II)

in an organic solvent in the presence of an acid,
  where each R' independently represents C1-C4 alkyl, or both R' together represent C2-C4 alkylene; to produce a compound of Formula I wherein $R^5$ is H or alkoxy,
  wherein condensing the pair of compounds of Formula II comprises performing two successive Pd-coupling reactions.

2. The method of claim 1, wherein said compound of Formula I has the structure of Formula IA or Formula IB:

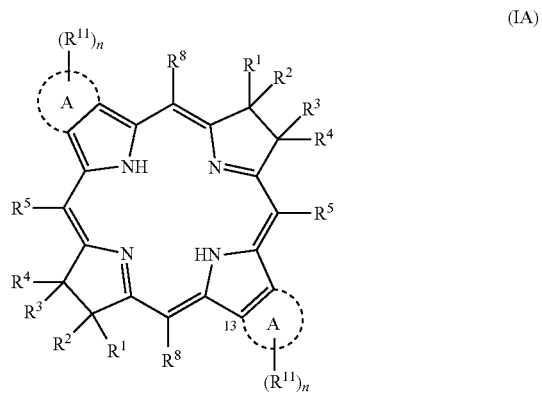

(IA)

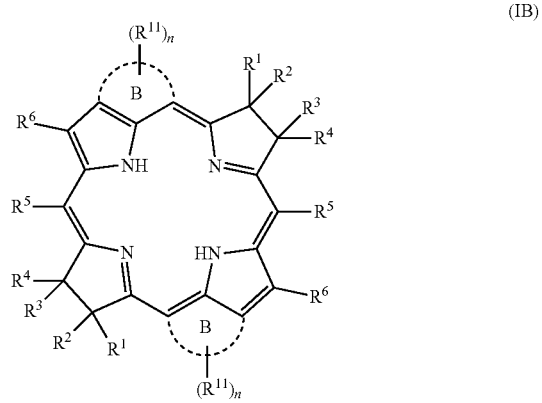

(IB)

or a metal conjugate thereof, wherein:
  rings A and B represent a fused aromatic or heteroaromatic ring system;
  n is from 1 or 2 to 4, 6 or 8; and
  each $R^1$, $R^2$, $R^3$, $R^4$, $R^5$, $R^6$, $R^8$ and $R^{11}$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups;

or $R^1$ and $R^2$ together are =O or spiroalkyl;

or $R^3$ and $R^4$ together are =O or spiroalkyl.

3. The method of claim 2, wherein said compound of Formula II has the structure:

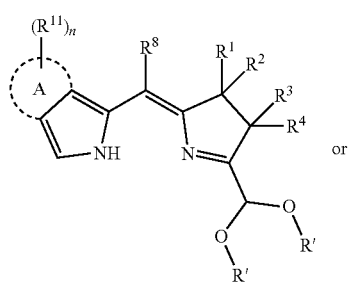

(IIA)

or

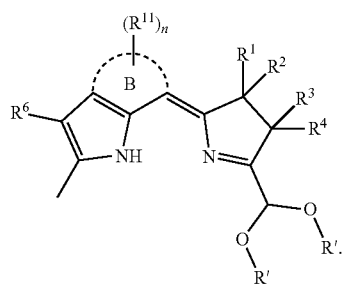

(IIB)

4. The method of claim 3, wherein said compound of Formula I has a structure selected from the group consisting of:

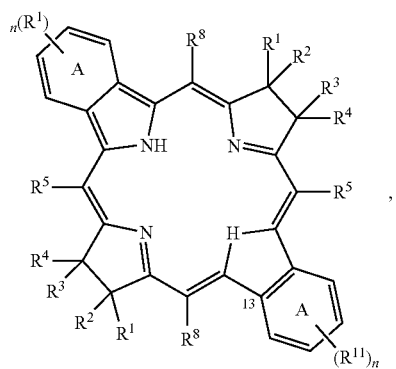

(IAi)

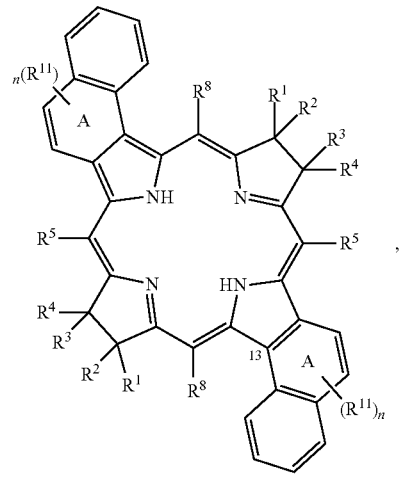

(IAii)

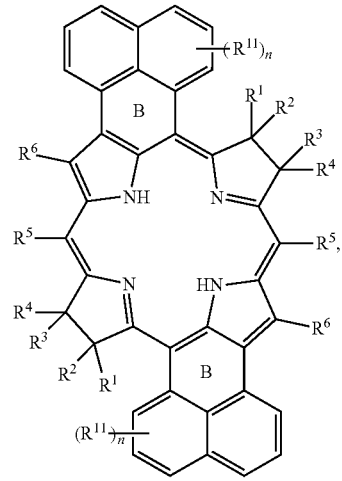

(IBi)

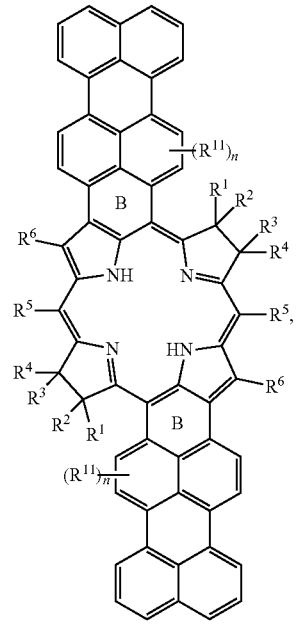

(IBii)

(IBiii)
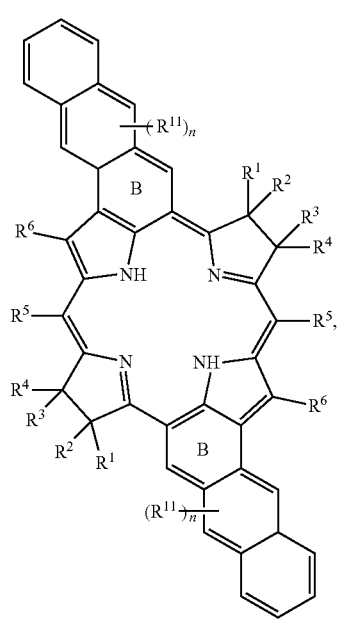
(IBv)
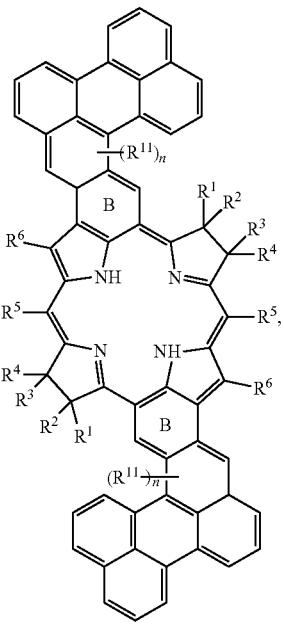
(IBiv)
(IBvi)
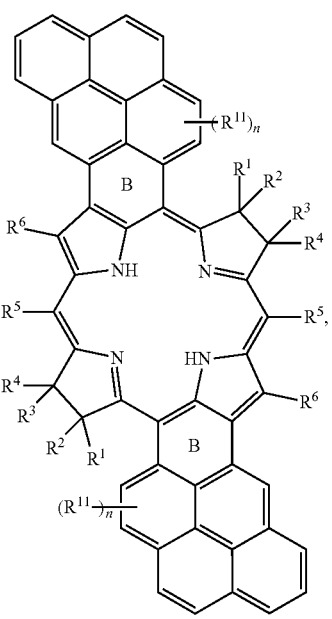

(IBvii)
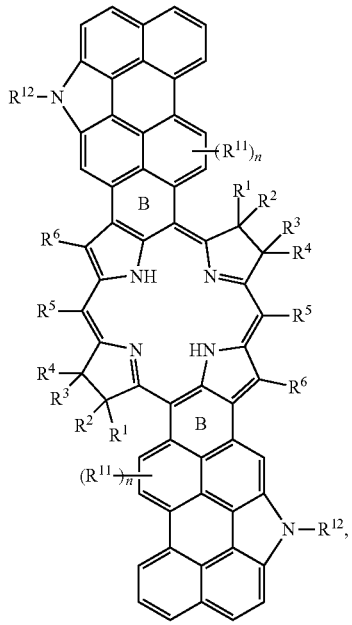

(IBviii)
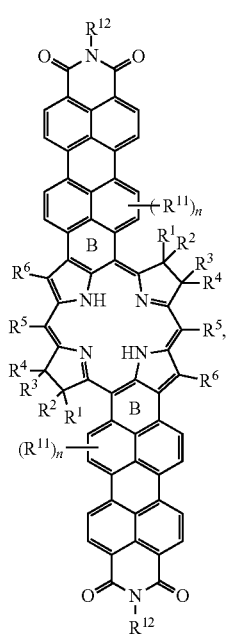

(IBix)
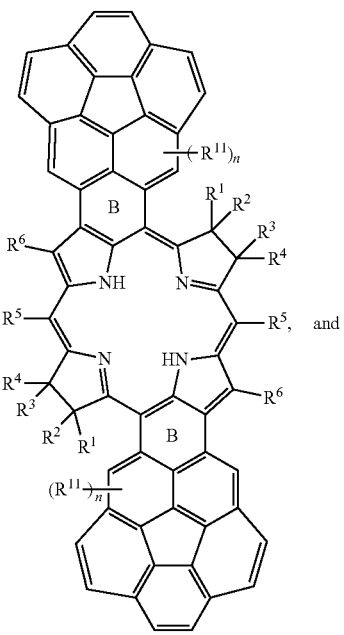

(IBx)
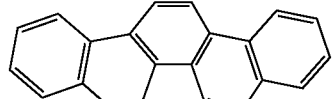

where:
n is from 1 or 2 to 4, 6 or 8;
each $R^{11}$, which may be substituted on any member ring of the corresponding ring system (A or B), is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups; and each $R^{12}$ of Formula IBvii or IBviii is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups.

5. The method of claim 1, wherein said compound is a conjugate with a metal selected from the group consisting of Pd, Pt, Mg, Zn, Al, Ga, In, Sn, Cu, Ni, and Au.

6. The method of claim 1, wherein said compound of Formula II has a structure selected from the group consisting of:

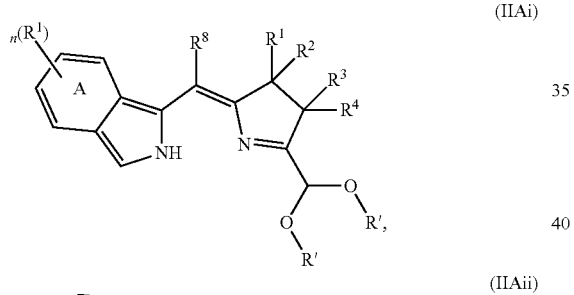
(IIAi)

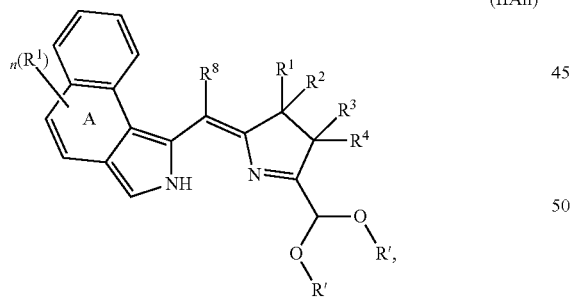
(IIAii)

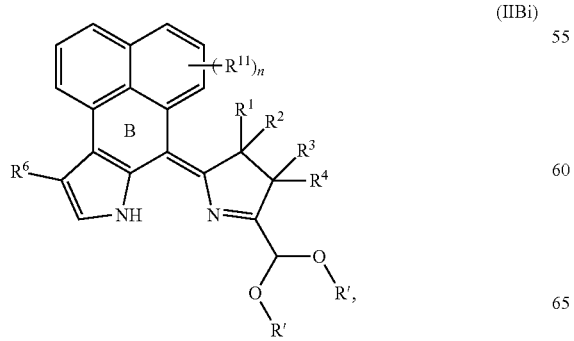
(IIBi)

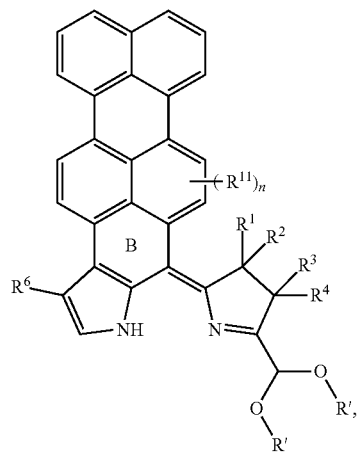
(IIBii)

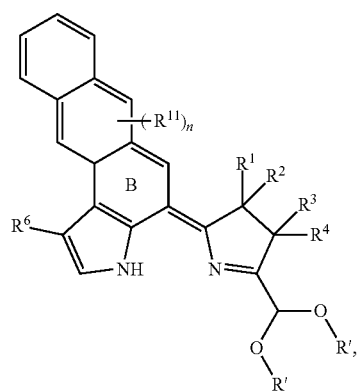
(IIBiii)

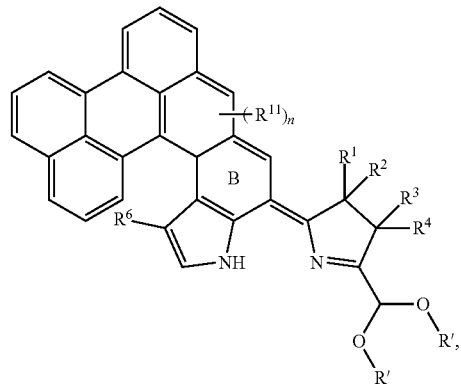
(IIBiv)

(IIBv)
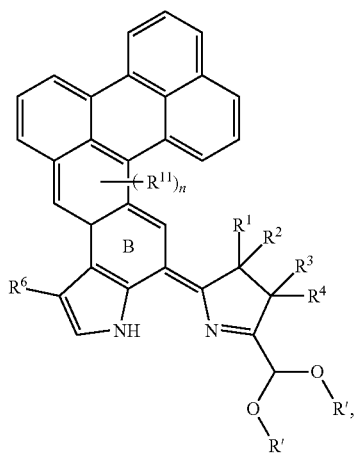
(IIBvi)
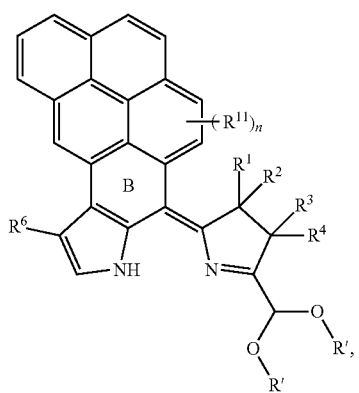
(IIBvii)
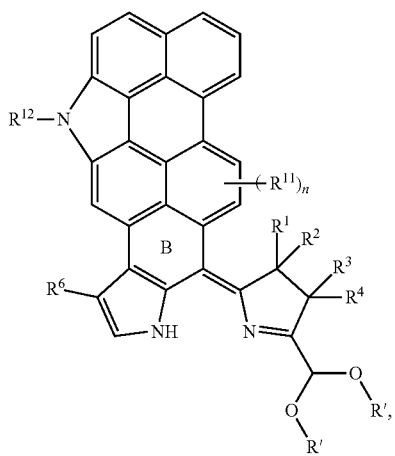
(IIBviii)
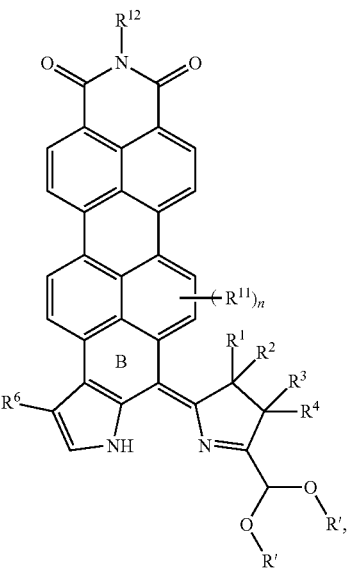
(IIBix)
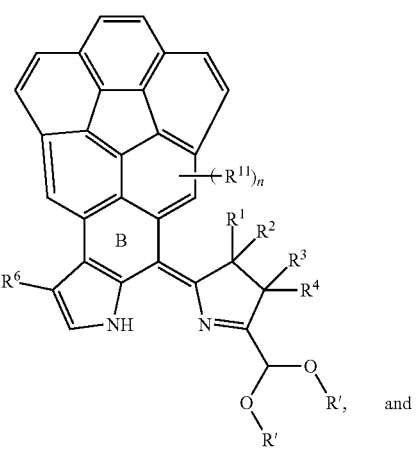
and
(IIBx)
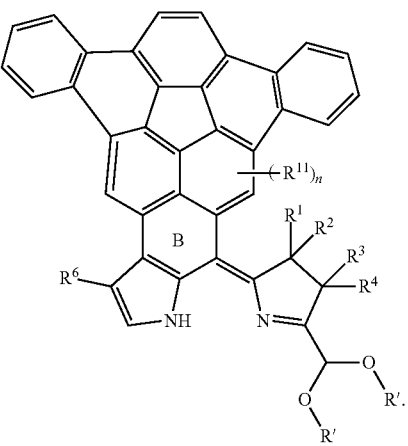
7. The method of claim 1, wherein:
at least one of $R^1$ through $R^{12}$ comprises a linking group, a hydrophilic group, and/or a targeting group.
8. The method of claim 1, wherein:
each $R^1$ comprises a hydrophilic group, and each $R^2$, $R^3$, and/or $R^4$ comprises a linking group or targeting group; or each R² comprises a hydrophilic group, and each R¹, R³, and/or R⁴ comprises a linking group or targeting group; or each R³ comprises a hydrophilic group, and each R¹, R², and/or R⁴ comprises a linking group or targeting group; or each R⁴ comprises a hydrophilic group, and each R¹, R², and/or R³ comprises a linking group or targeting group.

9. The method of claim 1, wherein the two successive Pd-coupling reactions comprise reacting a 3,13-dibromo-8,8,18,18-tetramethylbacteriochlorin with about two equivalents of an arene bearing adjacent halo and dihydroxyboryl or dialkoxyboryl groups, and performing a ring closure to provide a beta-meso-annulated bacteriochlorin.

10. The method of claim 1, further comprising performing a Suzuki coupling reaction.

11. A compound of Formula IA or Formula IB:

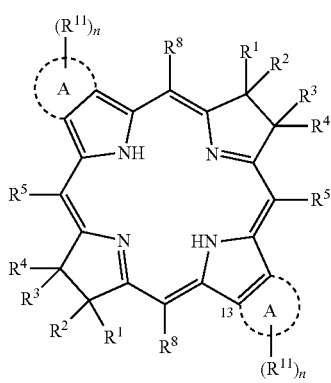

(IA)

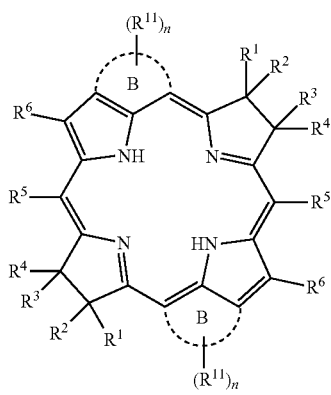

(IB)

or a metal conjugate thereof, wherein:
  rings A and B represent a fused aromatic or heteroaromatic ring system;
  n is from 1 or 2 to 4, 6, or 8; and
  each R², R³, R⁴, R⁵, R⁶, R⁸ and R¹¹ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, a hydrophilic group, a linking group, a surface attachment group, and a targeting group, wherein the hydrophilic group is selected from the group consisting of a polyol, polyalkylene oxide group, ionic group, polar group, and any combination thereof, wherein the linking group is selected from the group consisting of aryl, alkyl, heteroaryl, heteroalkyl, a peptide, a polysaccharide, and any combination thereof, and wherein the targeting group is selected from the group consisting of an antibody, a ligand, one member of a ligand-receptor binding pair, a nucleic acid, a protein, a peptide, a liposomal suspension, and any combination thereof;

or R¹ and R² together are =O or spiroalkyl;
or R³ and R⁴ together are =O or spiroalkyl, and
wherein:
  each R¹ comprises a hydrophilic group, and each R², R³, and/or R⁴ comprises a linking group or targeting group; or
  each R² comprises a hydrophilic group, and each R¹, R³, and/or R⁴ comprises a linking group or targeting group; or
  each R³ comprises a hydrophilic group, and each R¹, R², and/or R⁴ comprises a linking group or targeting group; or
  each R⁴ comprises a hydrophilic group, and each R¹, R², and/or R³ comprises a linking group or targeting group.

12. The compound of claim 11 selected from the group consisting of:

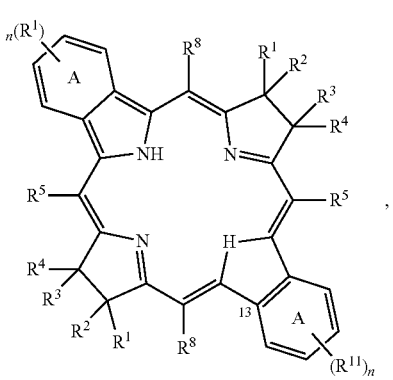

(IAi)

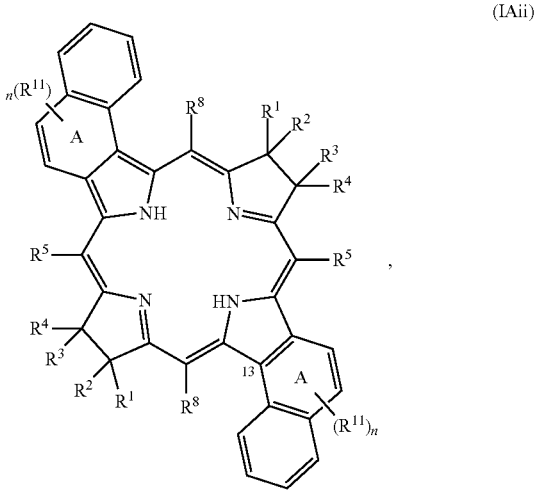

(IAii)

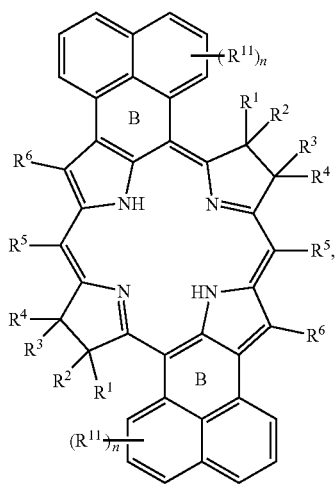
(IBi)
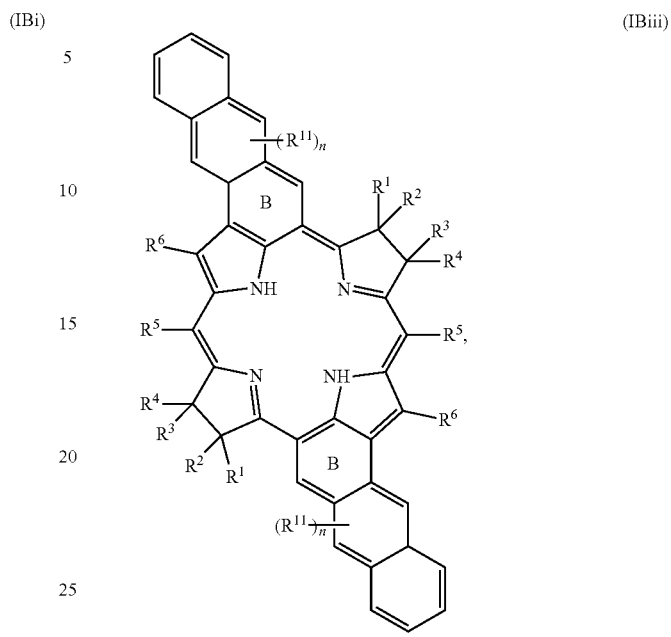
(IBiii)
(IBii)
(IBiv)

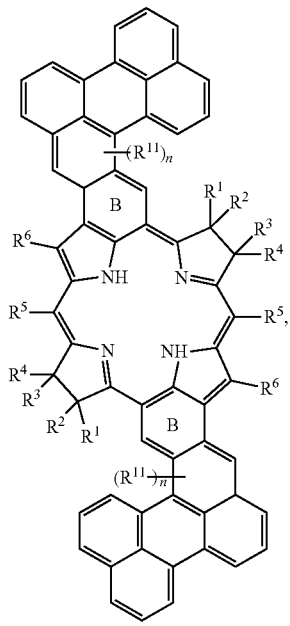 (IBv)
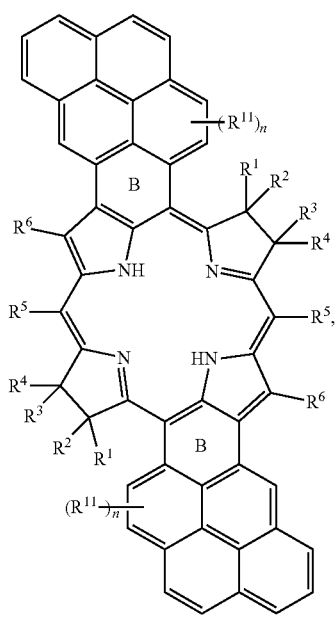 (IBvi)
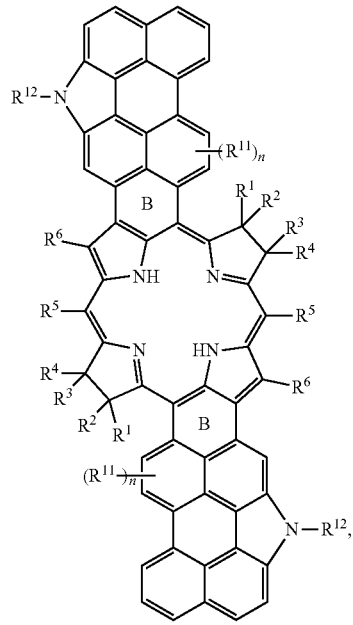 (IBvii)
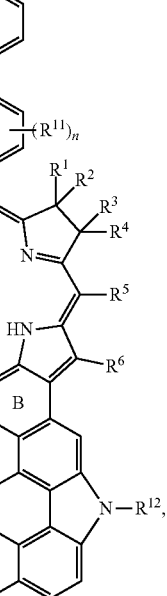 (IBviii)

-continued

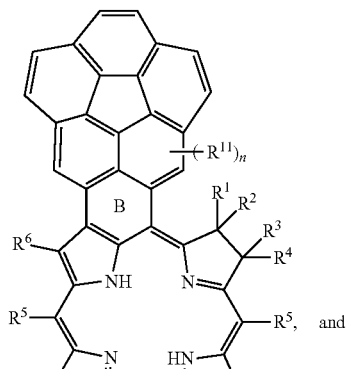

(IBix)

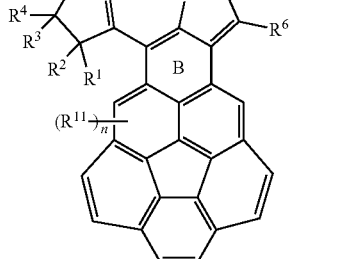

(IBx)

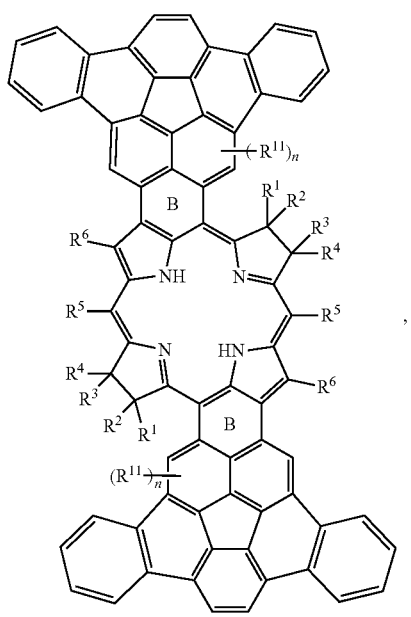

where:

n is from 1 or 2 to 4, 6 or 8;

each $R^{11}$, which may be substituted on any member ring of the corresponding ring system (A or B), is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups; and each $R^{12}$ of Formula IBvii or IBviii is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, hydrophilic groups, linking groups, surface attachment groups, and targeting groups.

13. The compound of claim 11, wherein said compound is a conjugate with a metal selected from the group consisting of Pd, Pt, Mg, Zn, Al, Ga, In, Sn, Cu, Ni, and Au.

14. A method for treating a target in a subject in need thereof, comprising: (i) administering to said subject the compound of claim 11 or a pharmaceutically acceptable conjugate thereof that preferentially associates with the target, and (ii) irradiating the target with light of a wavelength and intensity sufficient to treat said target.

15. A photodynamic therapy method for treating hyperproliferative tissue in a subject in need thereof, comprising: (i) administering to said subject a compound of claim 11 or a pharmaceutically acceptable conjugate thereof that preferentially associates with the hyperproliferative tissue, and (ii) irradiating the target with light of a wavelength and intensity sufficient to activate the compound, and thereby treat said hyperproliferative tissue.

16. A method for detecting the presence of a hyperproliferative tissue in a subject, comprising: (i) administering to the subject a compound of claim 11 or a pharmaceutically acceptable conjugate thereof that preferentially associates with the hyperproliferative tissue; and then (ii) visualizing the compound within the patient.

17. A method of detecting cells or particles by flow cytometry, comprising utilizing a compound of claim 11 as a detectable compound, wherein said cells or particles are labelled with the detectable compound.

18. A method of making a compound of Formula I:

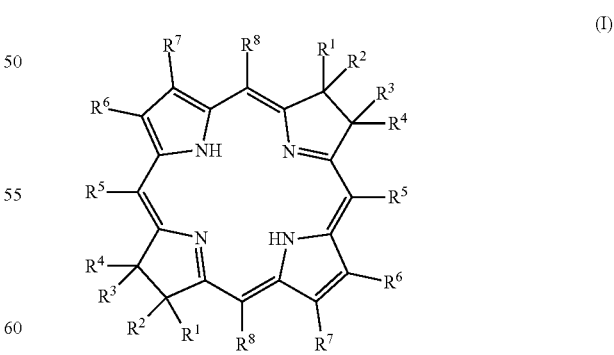

(I)

or a metal conjugate thereof, wherein:

each $R^1$, $R^2$, $R^3$, $R^4$, $R^5$, $R^6$, $R^7$ and $R^8$ is independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, aryloxy, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, a hydrophilic group, a linking group, a surface attachment group, and a targeting group, wherein the hydrophilic group is selected from the group consisting of a polyol, polyalkylene oxide group, ionic group, polar group, and any combination thereof, wherein the linking group is selected from the group consisting of aryl, alkyl, heteroaryl, heteroalkyl, a peptide, a polysaccharide, and any combination thereof, and wherein the targeting group is selected from the group consisting of an antibody, a ligand, one member of a ligand-receptor binding pair, a nucleic acid, a protein, a peptide, a liposomal suspension, and any combination thereof;

or $R^1$ and $R^2$ together are =O or spiroalkyl;

or $R^3$ and $R^4$ together are =O or spiroalkyl;

where $R^6$ and $R^7$, or $R^7$ and $R^8$, together represent a fused aromatic or heteroaromatic ring systems;

said method comprising condensing a pair of compounds of Formula II:

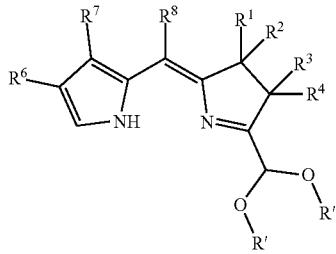

(II)

in an organic solvent in the presence of an acid, where each R' independently represents C1-C4 alkyl, or both R' together represent C2-C4 alkylene; to produce a compound of Formula I wherein $R^5$ is H or alkoxy, wherein said compound of Formula II has a structure selected from the group consisting of:

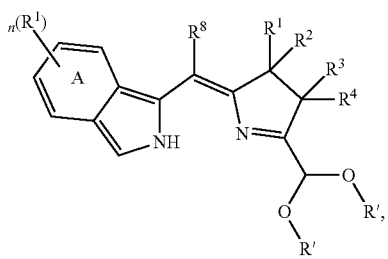

(IIAi)

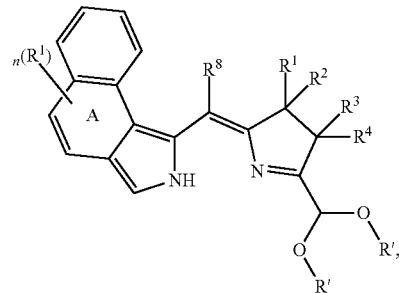

(IIAii)

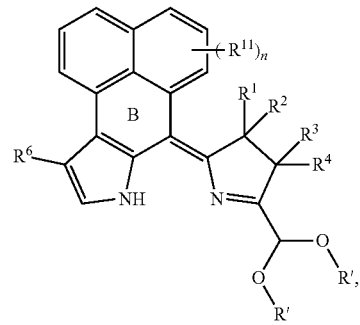

(IIBi)

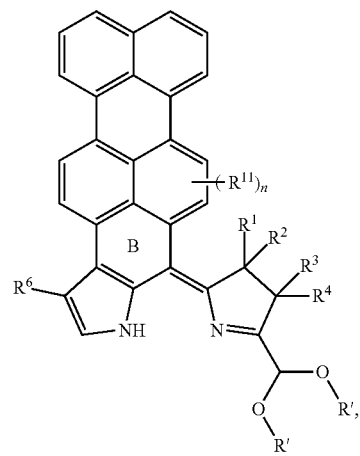

(IIBii)

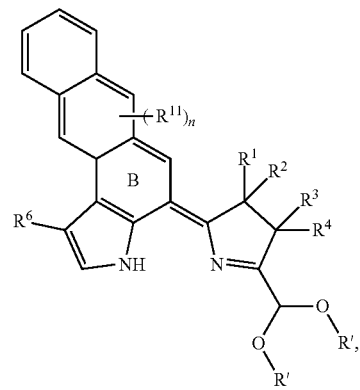

(IIBiii)

-continued
(IIBiv)
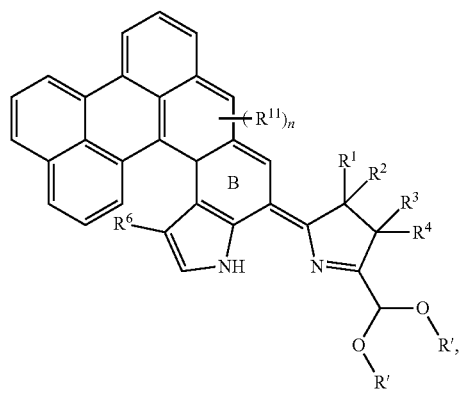
(IIBv)
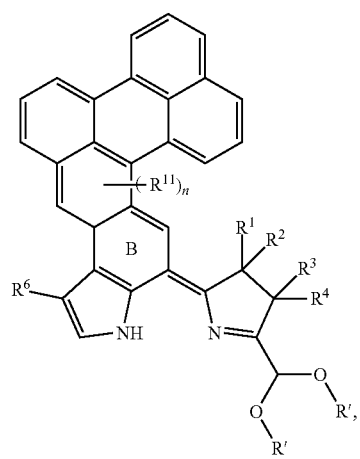
(IIBvi)
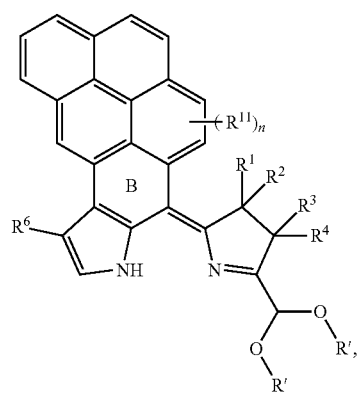
(IIBvii)
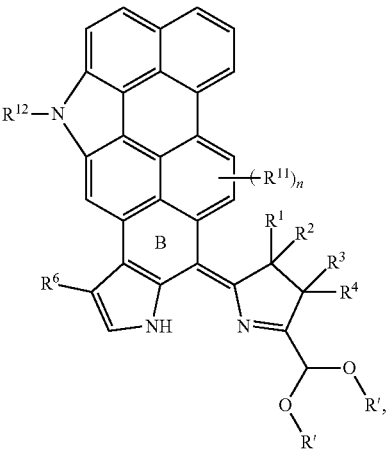
(IIBviii)
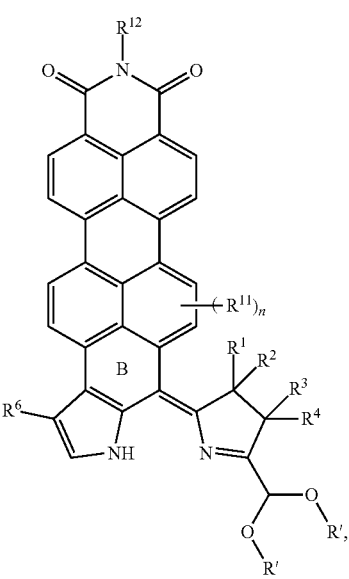
(IIBix)
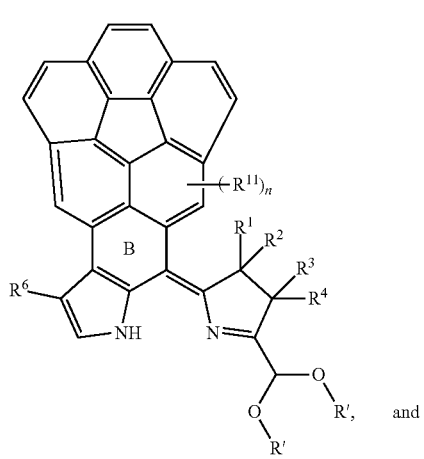
and -continued
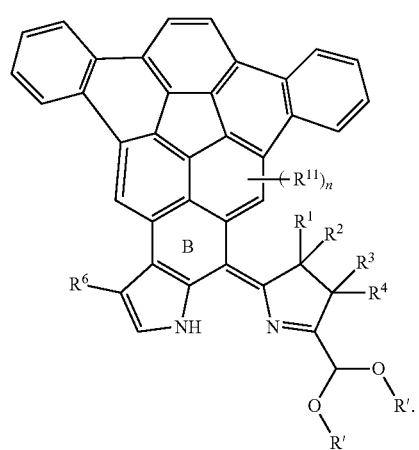
(IIBx)
* * * * *

UNITED STATES PATENT AND TRADEMARK OFFICE
CERTIFICATE OF CORRECTION

PATENT NO. : 10,919,904 B2
APPLICATION NO. : 16/323607
DATED : February 16, 2021
INVENTOR(S) : Liu et al.

It is certified that error appears in the above-identified patent and that said Letters Patent is hereby corrected as shown below:

In the Specification

Column 22, Line 50: Please correct "(IBix)" to read -- (IIBix) --

Column 23, Line 2: Please correct "(IBx)" to read -- (IIBx) --

Column 49, Line 45: Please correct "(1) $CH_2NO_2$" to read -- (1) $CH_3NO_2$ --

Column 56, Line 15: Please correct "BC-$R^5$" to read -- BC-$R^{10}$ --

Column 59, Lines 22-26: Please correct " 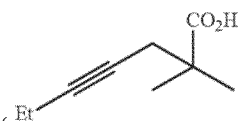 " to read -- 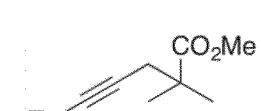 --

Column 60, Lines 3-6: Please correct " 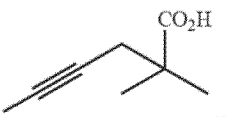 " to read -- 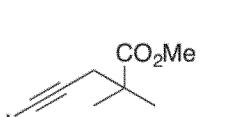 --

Column 62, Line 67: Please correct "described,'" to read -- described,[7] --

Column 63, Line 36: Please correct "$BF_3.Et_2O$" to read -- $BF_3 \cdot Et_2O$ --

Column 71, Line 16: Please correct "$TsOH.H_2O$" to read -- $TsOH \cdot H_2O$ --

Column 73, Line 35: Please correct "$TsOH.H_2O$" to read -- $TsOH \cdot H_2O$ --

Column 75, Line 38: Please correct "$TsOH.H_2O$" to read -- $TsOH \cdot H_2O$ --

Signed and Sealed this
Twenty-sixth Day of October, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,919,904 B2

Column 78, Line 2: Please correct "TsOH.H₂O" to read -- TsOH·H₂O --

Column 82, Line 44: Please correct "TsOH.H₂O" to read -- TsOH·H₂O --

Column 84, Line 27: Please correct "TsOH.H₂O" to read -- TsOH·H₂O --

Column 86, Line 5: Please correct "TsOH.H₂O" to read -- TsOH·H₂O --

Column 87, Line 49: Please correct "TsOH.H₂O" to read -- TsOH·H₂O --

Column 91, Line 27: Please correct "TsOH.H₂O" to read -- TsOH·H₂O --